United States Patent
Stern et al.

(10) Patent No.: US 6,228,837 B1
(45) Date of Patent: May 8, 2001

(54) ENDOTHELIAL MONOCYTE ACTIVATING POLYPEPTIDE II: A MEDIATOR WHICH ACTIVATES HOST RESPONSE

(75) Inventors: David M. Stern, Great Neck, NY (US); Matthias Clauss, Bad Nauheim (DE); Janet Kao; Mark Kayton, both of New York, NY (US); Steven K. Libutti, Fort Lee, NJ (US)

(73) Assignee: The Trustees of Columbia University in the City of New York, New York, NY (US)

(*) Notice: Subject to any disclaimer, the term of this patent is extended or adjusted under 35 U.S.C. 154(b) by 0 days.

(21) Appl. No.: 08/360,821

(22) PCT Filed: Sep. 29, 1994

(86) PCT No.: PCT/US94/11085

§ 371 Date: Oct. 8, 1996

§ 102(e) Date: Oct. 8, 1996

(87) PCT Pub. No.: WO95/09180

PCT Pub. Date: Apr. 6, 1995

Related U.S. Application Data

(63) Continuation-in-part of application No. 08/129,456, filed on Sep. 29, 1993, now Pat. No. 5,641,867.

(51) Int. Cl.$^7$ .................................................. A61K 38/00
(52) U.S. Cl. ........................................... 514/12; 530/324
(58) Field of Search ................................. 530/324, 350, 530/300; 514/12

(56) References Cited

U.S. PATENT DOCUMENTS

| | | |
|---|---|---|
| 4,456,550 | 6/1984 | Dvorak et al. . |
| 4,481,137 | 11/1984 | Ohnishi et al. . |
| 4,650,674 | 3/1987 | Aggarwal et al. . |
| 4,785,077 | 11/1988 | Kornbluth et al. . |
| 4,863,727 | 9/1989 | Zimmerman et al. . |
| 4,900,724 | 2/1990 | Kato et al. . |
| 4,980,160 | 12/1990 | Goldberg et al. . |

OTHER PUBLICATIONS

Gura et al, Science vol. 278 p. 1041, Nov. 1997.*
DuBois, Appella et al., *Cancer Research* (Nov. 1980) 40:4204–4208.
DuBois, Law, and Appella, *Proc. Natl. Acad. Sci.–USA* (Dec. 1982) 79:7669–7673.
Goding, et al. *Journal of Immunological Method* (1980) 39285–39308.
Goodman, et al., *Basic Clinical Immunology* Fudenberg et al. (Eds.) Lange Medical Publication, Los Altos, California (1976) 32–40.
Jornvall, et al., *Proc. Natl. Acad. Sci.–USA* (Jan. 1982) 79(2):287–291.
Kao, et al., *J. Biol. Chem.* (Oct. 5, 1992) 267(28):20239–20247.
Martin, et al., *Cancer Research* (Apr. 1986) 46:2189–2192.
Nawroth, et al., *J. Exp. Med.* (Aug. 1988) 168:637–647.
Noguchi, et al., *Biochemical and Biophysical Research Communications* (Apr. 14, 1989) 160(1):222–227.
Robins, et al., *Immunology in Plant Sciences* (1986) Linskens, et al. (Eds.) Springer–Verlag, New York, 86–141; and.
Suffness, et al., *J. Natural Products* (1982) 45:1–14.

* cited by examiner

*Primary Examiner*—Sheela Huff
(74) *Attorney, Agent, or Firm*—John P. White; Cooper & Dunham LLP

(57) ABSTRACT

This invention provides a purified endothelial monocyte activating polypeptide (EMAP II). It further provides a method of obtaining purified endothelial monocyte activating polypeptide (EMAP II), a method of making antibodies to it and a method of detecting it. This invention also provides an effector cell activating protein which contains an amino acid sequence homologous to RIGRIVT and a method of detecting same. This invention also provides a method of treating a tumor in a subject by administering an effective dose of endothelial monocyte activating polypeptide (EMAP II).

31 Claims, 44 Drawing Sheets

FIGURE 4-1

```
            1
            GAGGCTGCTCAAGAGCTGCGGTTGGGTCACCGCTTCATGTTTCTCTGC
                                                                      99
     CGATTCTGGGGAAAG ATG GCA ACG AAT GAT GCT GTT CTG AAG AGG CTG GAG
        murine     1   M   A   T   N   D   A   V   L   K   R   L   E  12
        human      1   .   .   N   .   .   .   .   .   .   .   .   .  12
    100
    CAG AAG GGT GCA GAG GCG GAT CAG ATC ATC GAA TAT CTC AAG CAG CAG GTT
13   Q   K   G   A   E   A   D   Q   I   I   E   Y   L   K   Q   Q   V
13   .   .   .   .   .   .   .   .   .   .   .   .   .   .   .   .   -
                                                                    198
    GCT CTT CTT AAG GAG AAA GCA ATT TTG CAG GCA ACA ATG AGA GAA GAA
     A   L   L   K   E   K   A   I   L   Q   A   T   M   R   E   E   45
     S   .   .   .   .   .   .   .   .   .   .   .   L   .   .   .   45
    199
    AAG AAA CTT CGA GTT GAA AAT GCT AAA CTG AAA AAA GAA ATA GAA GAG CTA
46   K   K   L   R   V   E   N   A   K   L   K   K   E   I   E   E   L
46   .   .   .   .   .   .   .   .   .   .   .   .   .   .   .   .   .
                                                                    297
    AAG CAA GAG CTG ATT CTG GCA GAA ATT CAT AAC GGA GTG GAG CAA GTG
     K   Q   E   L   I   L   A   E   I   H   N   G   V   E   Q   V   78
     .   .   .   .   .   Q   .   .   .   Q   .   .   .   K   .   I   78
    298
    CGT GTT CGA TTG AGT ACT CCA CTG CAG ACG AAC TGT ACT GCT TCT GAA AGT
79   R   V   R   L   S   T   P   L   Q   T   N   C   T   A   S   E   S
79   P   F   P   S   G   .   .   .   .   H   A   .   S   M   V   .   N
                                                                    396
    GTG GTG CAG TCT CCA TCA GTA GCA ACC ACC GCC TCT CCT GCT ACA AAA
     V   V   Q   S   P   S   V   A   T   T   A   S   P   A   T   K   111
     .   I   .   .   T   A   .   -   .   .   V   .   S   G   .   .   110
    397
    GAG CAG ATC AAA GCG GGA GAA GAA AAG AAG GTG AAA GAG AAG ACT GAA AAG
112  E   Q   I   K   A   G   E   E   K   K   V   K   E   K   T   E   K
111  .   .   .   .   .  GGT  .   D   .   .   .   A   .   .   .   I   .   .
                                                                        ↓
    AAA GGA GAG AAA AAG GAG AAG CAG CAG TCG GCA GCA GCA AGT ACT GAC
     K   G   E   K   K   E   K   Q   Q   S   A   A   A   S   T   D   144
     .   .   .   .   .  .K   .   .   .   .   I   .   G   .   A   .   146
    496
    TCC AAG CCT ATC GAC GCA TCG CGT CTG GAT CTT CGA ATT GGT TGT ATT GTT
145  S   K   P   I   D   A   S   R   L   D   L   R   I   G   C   I   V
147  .   .   .   .   .   V   .   .   .   .   .   .   .   .   .   .   I
                                                                    594
    ACT GCC AAG AAG CAC CCT GAT GCA GAT TCA CTG TAT GTG GAG GAA GTA
     T   A   K   K   H   P   D   A   D   S   L   Y   V   E   E   V   177
     .   .   R   .   .   .   .   .   .   .   .   .   .   .   .   .   179
```

FIGURE 4-2

```
    595
    GAT GTG GGA GAA GCA GCC CCG CGC ACG GTC GTC AGC GGG CTG GTG AAT CAT
178  D   V   G   E   A   A   P   R   T   V   V   S   G   L   V   N   H
180  .   .   .   .   I   .   .   .   .   .   .   .   .   .   .   .   .

693
    GTT CCT CTA GAA CAG ATG CAA AAT CGT ATG GTG GTT TTA CTC TGT AAT
     V   P   L   E   Q   M   Q   N   R   M   V   V   L   L   C   N   210
     .   .   .   .   .   .   .   .   .   .   I   .   .   .   .   .   212

694
    CTG AAG CCT GCA AAG ATG CGG GGA GTT CTG TCT CAA GCC ATG GTG ATG TGT
211  L   K   P   A   K   M   R   G   V   L   S   Q   A   M   V   M   C
213  .   .   .   .   .   .   .   .   .   .   .   .   .   .   .   .   .

792
    GCC AGT TCA CCA GAG AAA GTG GAG ATT CTG GCC CCT CCC AAC GGG TCC
     A   S   S   P   E   K   V   E   I   L   A   P   P   N   G   S   243
     .   .   .   .   .   .   I   .   .   .   .   .   .   .   .   .   245

793
    GTT CCT GGG GAC AGA ATT ACT TTT GAT GCT TTT CCT GGA GAG CCT GAC AAG
244  V   P   G   D   R   I   T   F   D   A   F   P   G   E   P   D   K
246  .   .   .   .   .   .   .   .   .   .   .   .   .   .   .   .   .

891
    GAG CTA AAC CCT AAG AAG AAG ATC TGG GAG CAG ATC CAG CCT GAC CTG
     E   L   N   P   K   K   K   I   W   E   Q   I   Q   P   D   L   276
     .   .   .   .   .   .   .   .   .   .   .   .   .   .   .   .   278

892
    CAC ACC AAT GCT GAG TGT GTG GCC ACA TAC AAA GGA GCT CCC TTT GAG GTG
277  H   T   N   A   E   C   V   A   T   Y   K   G   A   P   F   E   V
279  .   .   .   D   .   .   .   .   .   .   .   .   V   .   .   .   .

990
    AAG GGG AAG GGA GTT TGC AGA GCC CAA ACC ATG GCC AAT AGT GGA ATT
     K   G   K   G   V   C   R   A   Q   T   M   A   N   S   G   I   309
     .   .   .   .   .   .   .   .   .   .   .   S   .   .   .   .   311

991
    AAA TAA GTGCTCTGTAACTGAAAGACATTGGCGAAAACTTAATAACAATAAAGAGAAGTGTGTTT
310  K  stop
312  .   .
                                        1086
          ATCACTTACATATAAAAAAAAAAAAAAAAAAA
```

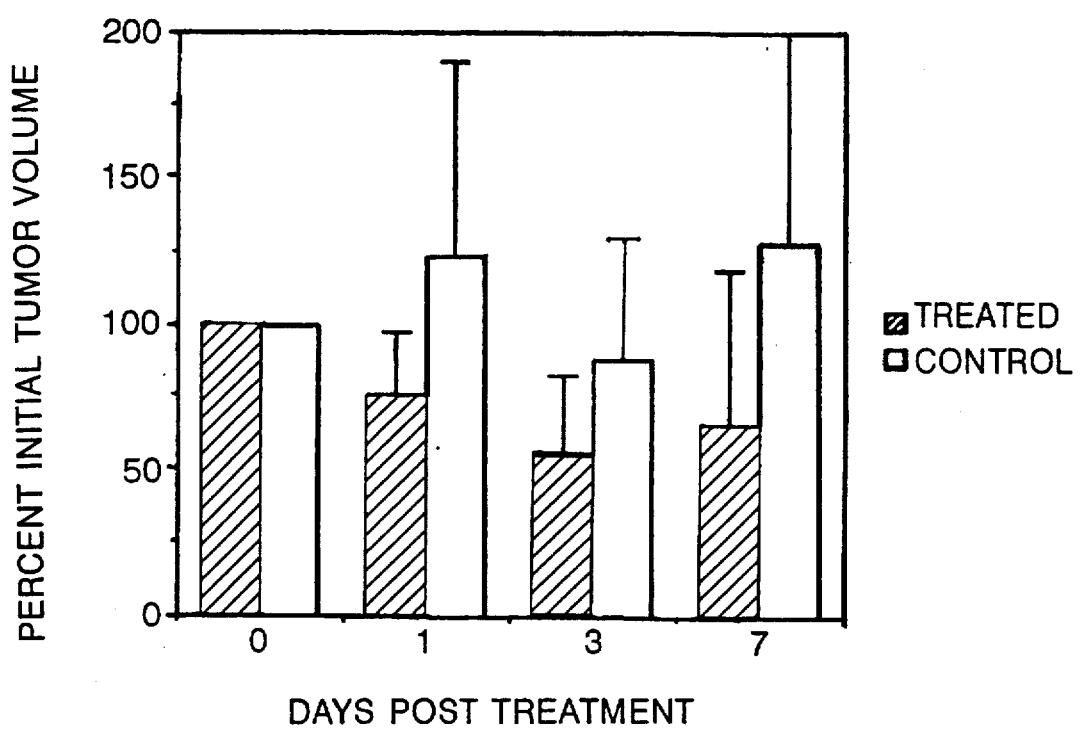

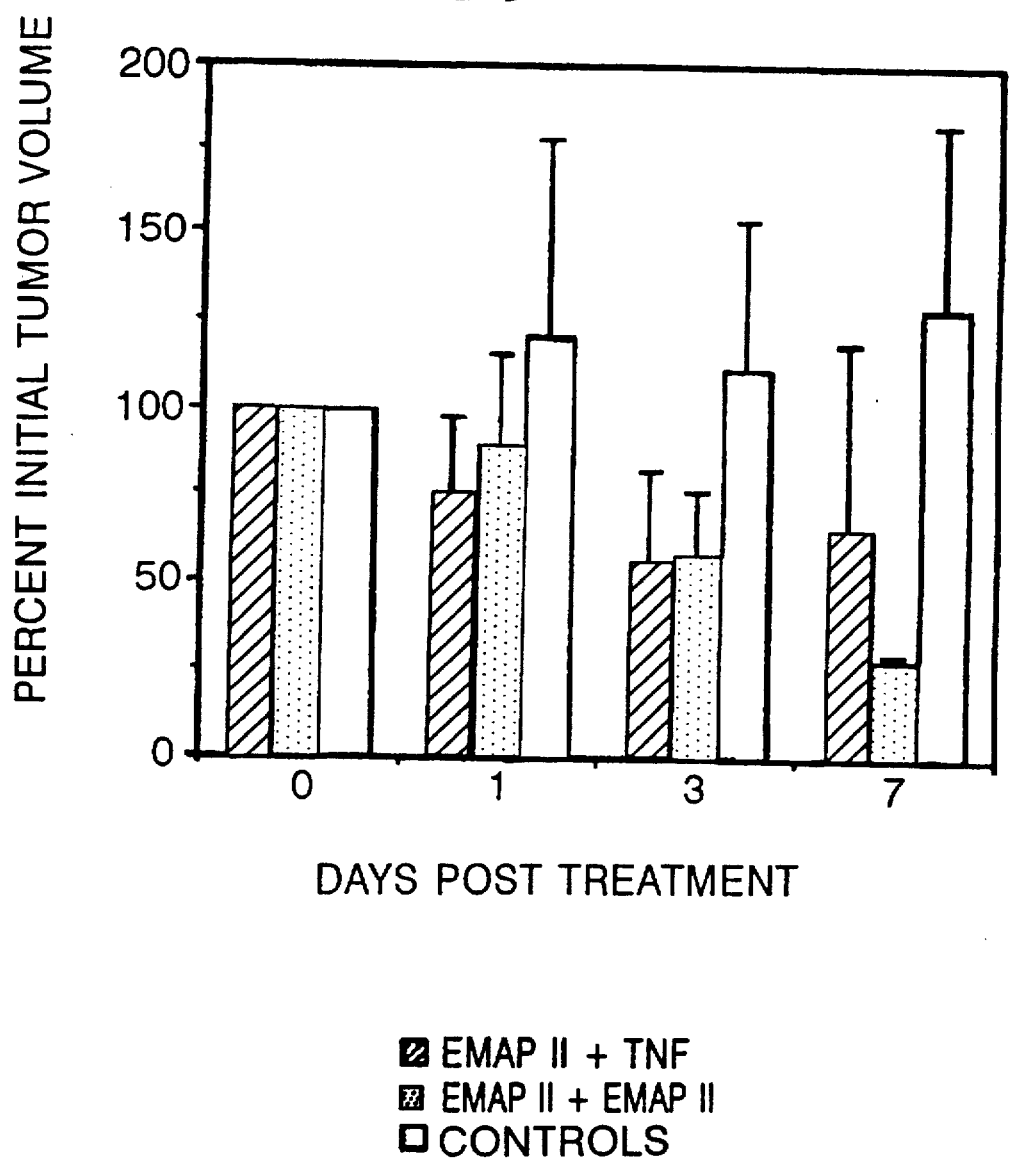

FIGURE 13

```
EMAP-II  147. K P I D V S R L D I R I G C I I T A K K.
vWAg-II  471. V Q L P L L K G D L R L Q R T V T A S V.
IL-8      23. A V L P R S A K E L R C Q C I R T Y S K.
IL-1β    117. A P V R S L N C T L R D S Q Q K S L V M.
```

ENDOTHELIAL MONOCYTE ACTIVATING POLYPEPTIDE II: A MEDIATOR WHICH ACTIVATES HOST RESPONSE

This application is a continuation-in-part of U.S. application Ser. No. 08/129,456, filed Sep. 29, 1993, now U.S. Pat. No. 5,641,867, the contents of which are hereby incorporated by reference.

The invention disclosed herein was made with Government support under NIH-PHS Grants Nos. HL02641, HL21006, HL42507, HL42833, and HL34625 from the Department of Health and Human Services. Accordingly, the U.S. Government has certain rights in this invention.

Throughout this application, various references are referred to within parenthesis. Disclosures of these publications in their entireties are hereby incorporated by reference into this application to more fully describe the state of the art to which this invention pertains. Full bibliographic citation for these references may be found at the end each series of experiments.

BACKGROUND OF THE INVENTION

Tumor vasculature is uniquely subject to the influence of products derived from the neoplastic cells. This may underlie the altered reactivity of vessels in certain tumors to catecholamines (1), tumor necrosis factor (TNF), flavone acetic acid (2), as well as other agents. To identify tumor-derived mediators which alter vascular function, the experiments described herein focussed on murine methylcholanthrene A (meth A)-induced fibrosarcomas. In vivo, this tumor is sensitive to TNF, and infusion of the cytokine at low concentrations results in vascular compromise localized to the neoplastic lesions with early thrombosis/hemorrhage in the vessels and increased vascular permeability, and rater regression of the tumor (3–7). In contrast, cultured meth A tumor cells are relatively insensitive to TNF (3,8). This suggests that tumor-derived mediators, potentially acting at the level of the endothelium, a central regulator of vascular tone, permeability and thrombogenicity, could be important in host-tumor interactions.

These considerations have led to the study of supernatants of meth A fibrosarcoma cells in order to identify soluble factors which alter endothelial functions. Recently, the purification of an apparently unique polypeptide, $M_r \approx 40,000$, which alters endothelial and monocyte properties (Endothelial cell and Monocyte Activating Polypeptide, EMAP I) was reported (9–10). Reported here are the purification, N-terminal sequence, and characterization of another novel polypeptide from the same meth A fibrosarcoma supernatants, which alters endothelial and monocyte functions, induces the migration of monocytes and granulocytes, and induces an inflammatory response in the mouse footpad model. Because of these properties, this second polypeptide derived from meth A cells is termed endothelial-monocyte activating polypeptide II (EMAP II).

A prominent characteristic of immunogenic tumors is the presence of an inflammatory infiltrate surrounding the neoplastic lesion (103). One potentially important mechanism through which tumors modulate the host response is through the production of cytokines activating host effector cells, including mononuclear phagocytes (MPs), polymorphonuclear leukocytes (PMNs), and endothelial cells (ECs) (4–7). Using the murine methylcholanthrene A-induced fibrosarcomas (meth A) as a model system, three polypeptides with cytokine-like activities were identified (5–7). One of these is the murine homologue of vascular permeability factor/vascular endothelial growth factor (VPF/VEGF) (6) which modulates properties of ECs, including growth and induction of the procoagulant cofactor tissue factor, and MPs, including cell migration and tissue factor expression (8–13). In addition, two distinct polypeptides from meth A-conditioned medium termed endothelial-monocyte activating polypeptides I and II were isolated (5,7). EMAP II, a novel ≈20 kDa polypeptide which has recently been cloned and is not a member of previously described cytokine/chemokine families, has multiple effects on ECs, Mps, and PMNs in vitro, and induces an acute inflammatory response upon subcutaneous injection into mice (7).

Protein sequence data from the N-terminal region of EMAP II (residues #10–20) indicated a close relationship to von Willebrand factor antigen II (residues #480–490; 14–15), a molecule released by platelets and ECs along with von Willebrand factor (16–17). Pilot studies with purified von Willebrand antigen II showed that it had cytokine-like properties resembling EMAP II (18), leading to speculation that the region of strong sequence homology between the two molecules might mediate effects on target cells. Consistent with the possibility that the N-terminal position of EMAP II might be involved in its interaction with target cells is an homology to residues #31–37 of Interleukin (IL) 8, which includes the Glu-Leu-Arg motif associated with receptor binding and neutrophil activation by IL-8 (19–21). This study reports the synthesis of a series of peptides based on the N-terminal sequence of EMAP II (residues #6–20), and used these to perform experiments on cultured MPs and PMNs, and to inject into mouse footpads. The results support the hypothesis that this region of the molecule contributes to the functional activity of EMAP II. The N-terminal EMAP II-derived peptides interact with specific, potentially novel cellular binding sites, and may define a new ligand-receptor interaction important in tumor vasculature and inflammation.

SUMMARY OF THE INVENTION

This invention provides a purified endothelial monocyte activating polypeptide II (EMAP II).

This invention further provides a method of obtaining purified endothelial monocyte activating polypeptide II (EMAP II).

This invention provides a method of obtaining antibodies to purified endothelial monocyte activating polypeptide II (EMAP II).

This invention provides a method of detecting the presence of purified endothelial monocyte activating polypeptide II (EMAP II) in a sample.

This invention also provides an effector cell activating protein comprising a polypeptide having an amino acid sequence wherein at least four amino acid residues are the same as RIGRIVT and are in the same relative positions.

This invention further provides a method of detecting the presence in a sample of effector cell activating protein.

This invention provides a method of treating a tumor in a subject comprising administering an effective dose of endothelial monocyte activating polypeptide II (EMAP II).

DESCRIPTION OF THE FIGURES

FIGS. ((1-1)–(1-2)): Effect of EMAP II on migration and division of bovine aortic endothelial cells in an in vitro wound model. Confluent monolayers of BAE were stimulated to migrate and divide by removal of a ring fence creating a 5 mm diameter wound, at the time of wounding monolayers were exposed to EMAP II or control medium for 24 hours. Following incubation monolayers were washed, fixed in 3.5% paraformaldehyde in phosphate buffered saline containing 0.1% Nonidet P-40 and nuclei were stained with Hoechst 33258. Control monolayers migrating into the wound margin display normal interphase nuclei (upper panel) compared with those exposed to EMAP, in which there are many condensed, pyknotic (apoptotic) nuclei (lower panel). Wound margin is to the left.

FIGS. ((2-1)–(2-2)): Infusion of EMAP II in murine inflammatory model. Mice were given intravenous injections of vehicle alone or vehicle containing EMAP via the tail vein and sacrificed by humane methods at 4 hours post infusion. Tissues were fixed in 10% formalin, processed routine methods and sections stained with hematoxylin and eosin. Lung from mice injected with vehicle alone are unremarkable (upper panel) while those from mice exposed to EMAP display evidence of inflammation, mild edema, and cellular infiltrate (lower panel).

FIGS. (4-1)–(4-2): Murine and Human EMAP II cDNA and EMAP II Sequence Derived Therefrom (SEQ ID NOS. 34, 35 and 36).

Figure 5:
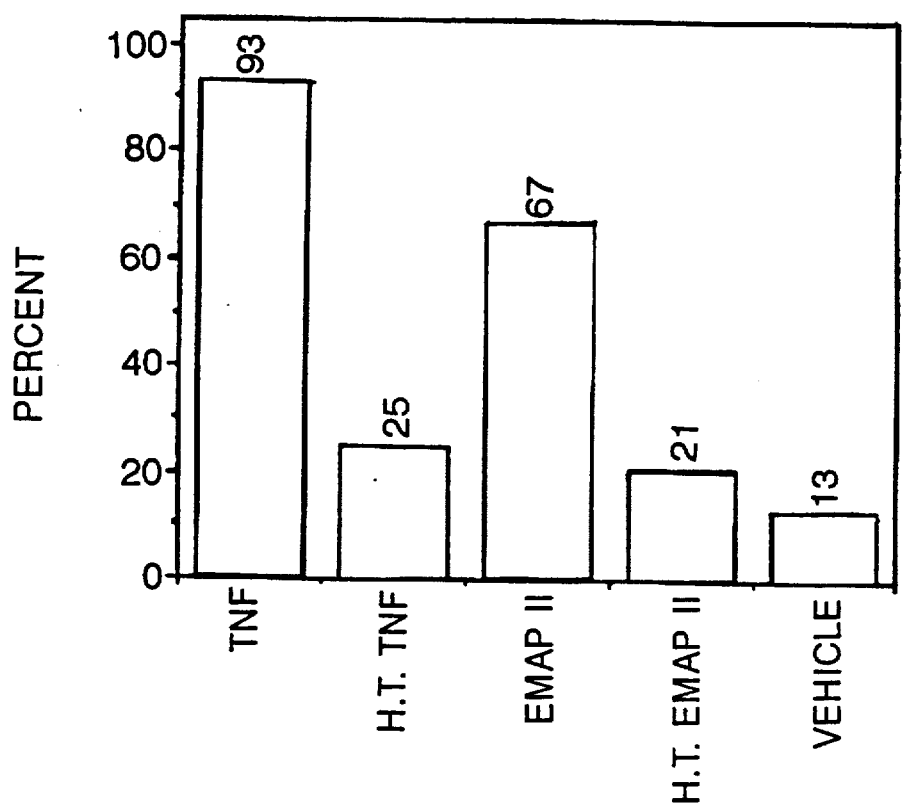

FIG. 5: Percentage of Meth A Tumors Demonstrating Gross Hemorrhage Six Hours After Single Injection FIG. 6: Percentage of Mouse Mammary Carcinoma Demonstrating Gross Hemorrhage Six Hours After Single Injection FIG. 7: Percentage of Mouse Mammary Carcinoma Demonstrating Gross Hemorrhage Six Hours After EMAP II+TNF Treatment FIGS. 8(A–E): (A) Tumor Regression After EMAP II+TNF Treatment: Treated vs. All Controls; (B) Tumor Regression After EMAP II+TNF Treatment: Treated vs. H.T. EMAP II+TNF; (C) Tumor Regression After EMAP II+TNF Treatment: Treated vs. EMAP II+H.T. TNF; (D) Tumor Regression After EMAP II+TNF Treatment: Treated vs. H.T. EMAP II+H.T. TNF; (E) Tumor Regression After EMAP II+TNF Treatment: Treated vs. Vehicle+TNF FIG. 9: Tumor Regression After EMAP II+EMAP II Treatment vs. Tumor Regression After EMAP II+TNF Treatment FIG. 10: Clonogenic Assay FIG. 11: Northern analysis of Meth A cell RNA for EMAP II. The size of the message was determined by comparison to the migration of markers. 5 ug of poly(A)+RNA was loaded.

Figure 12:
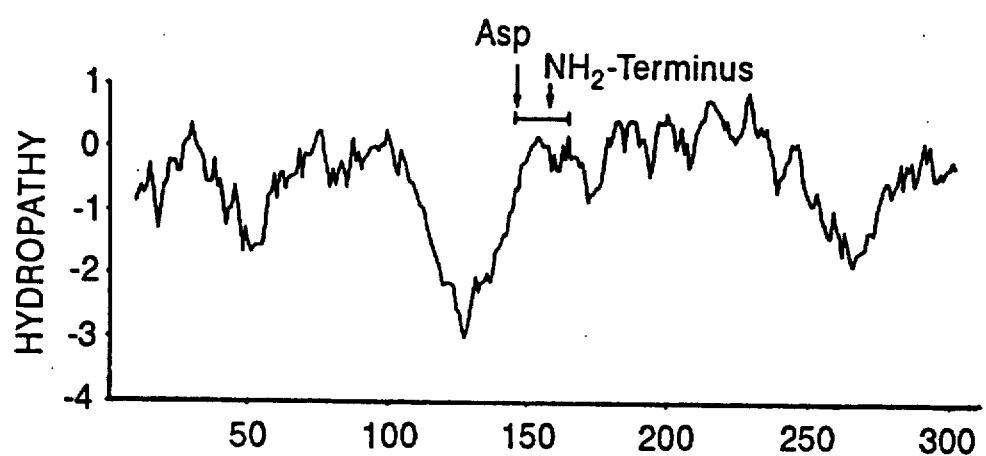

FIG. 12: Hydrophilicity ploy of murixe EMAP II. The hydropathy profile was generated by the method of Kyte and Doolittle (74). The NH2-terminal sequence obtained from EMAP II purified from the supernatant of Meth A cells is indicated ($NH_2$ terminus), and the Asp at the putative cleavage site for post-translational processing is shown. No evidence of a hydrophobic signal peptide is observed. Hydropathy is plotted versus deduced amino acid residue number.

FIG. 13: Comparison of EMAP II deduced amino acid sequence with the indicated residues from von Willebrand antigen II (vWAg II; 59, 60), IL-8 (54, 55), and IL-1B (48). All sequences are human, and numbering is based on the precursor form of each. Identical residues in two or more sequences are boxed.

Figure 14A:
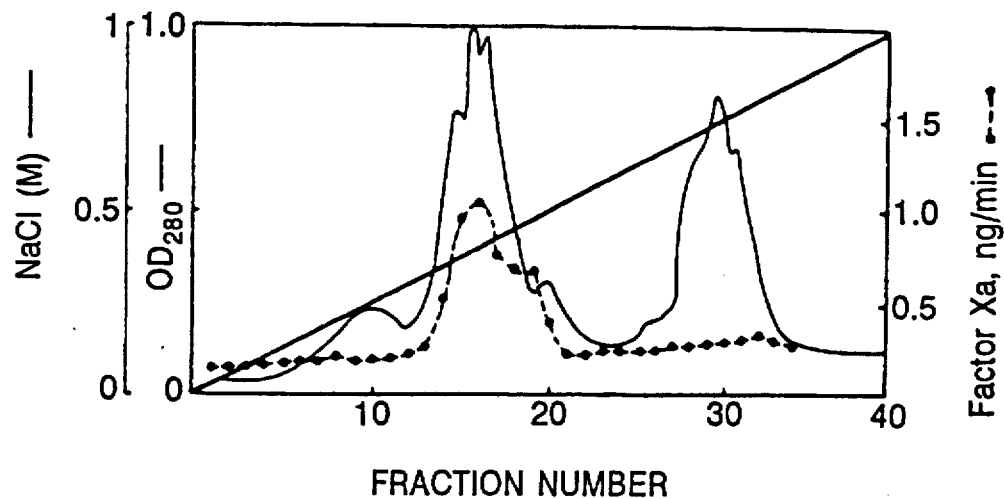

FIG. 14A: PPLC Mono Q chromatography of E. coli extracts from cultures transformed to overexpress EMAP II. Following sonication of the E. coli pellet in Tris-buffered saline, supernatants (≈35 mg of protein in each case) were applied to FPLC Mono Q (HR 5/5), the column was eluted with an ascending salt gradient, and fractions were monitored for absorbance at 280 nm and induction of tissue factor activity (each sample was diluted 1:100 for the latter) in ECs as described in the text.

Figure 14B:
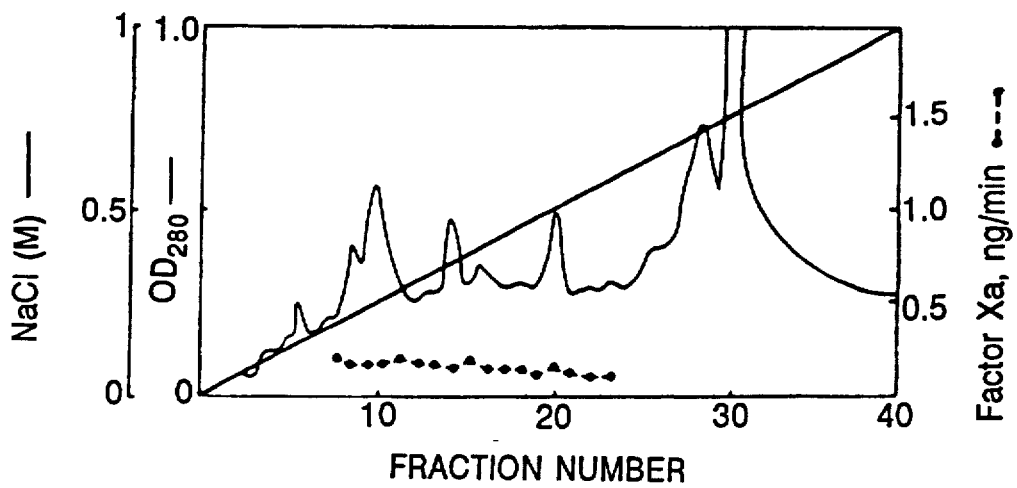

FIG. 14B: FPLC Mono Q chromatography of E. coli extracts from mock-transformed (i.e. vector alone) control cultures. See description of FIG. 14A.

Figure 15A:
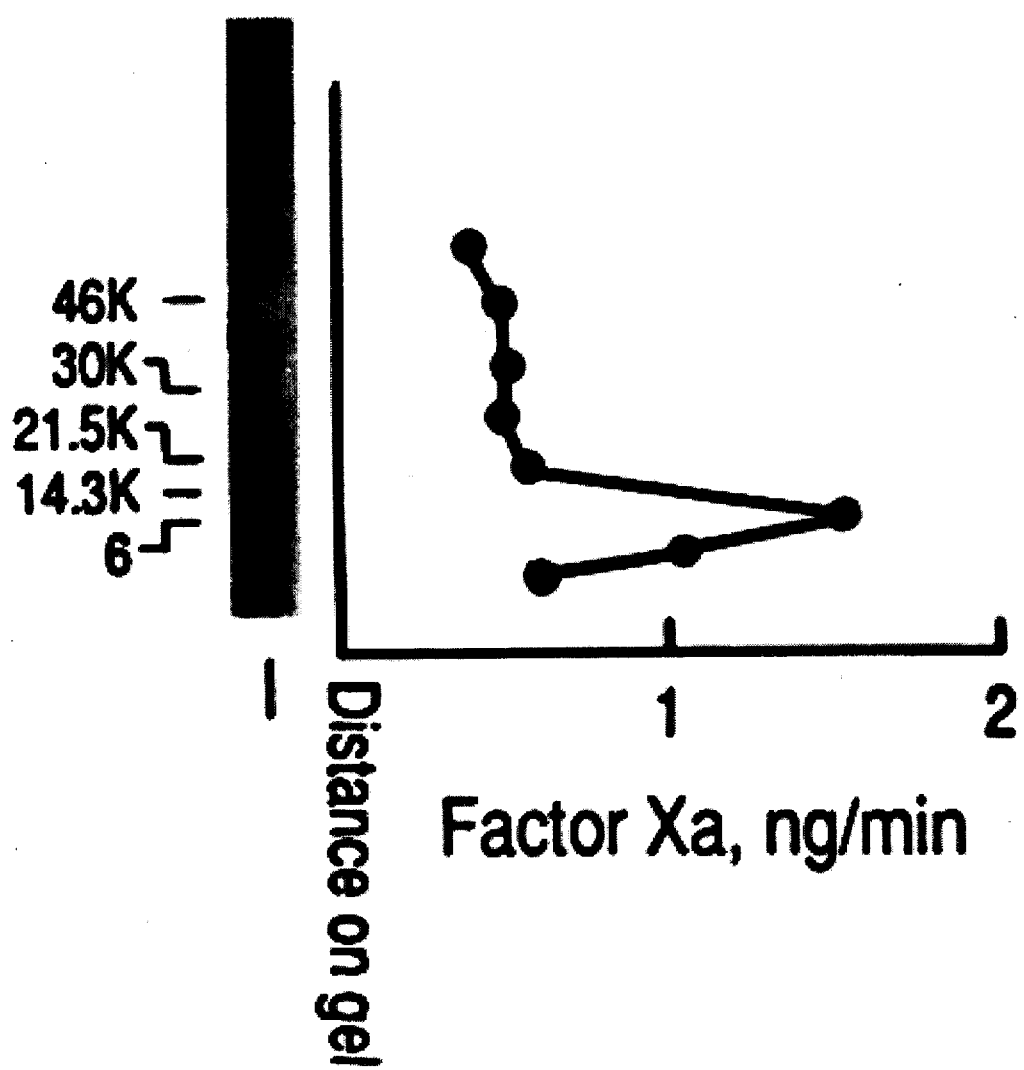

FIG. 15A: SDS-PAGE of EMAP II. The pool of fractions with maximum activity eluting from FPLC Mono Q were subjected to nonreduced SDS-PAGE (12%; 10 ug/lane), and protein in the gel was visualized by Coomassie Blue staining (lane I) or the gel was sliced into 1-mm pieces, material was eluted from each slice, incubated with cultured ECs, and induction of tissue factor activity was determined using the Factor VIIa-dependent Factor Xa formation assay (right portion of panel A). Factor Xa formation data is aligned with the corresponding portion of the gel from which the slice was obtained in lane I.

Figure 15B:
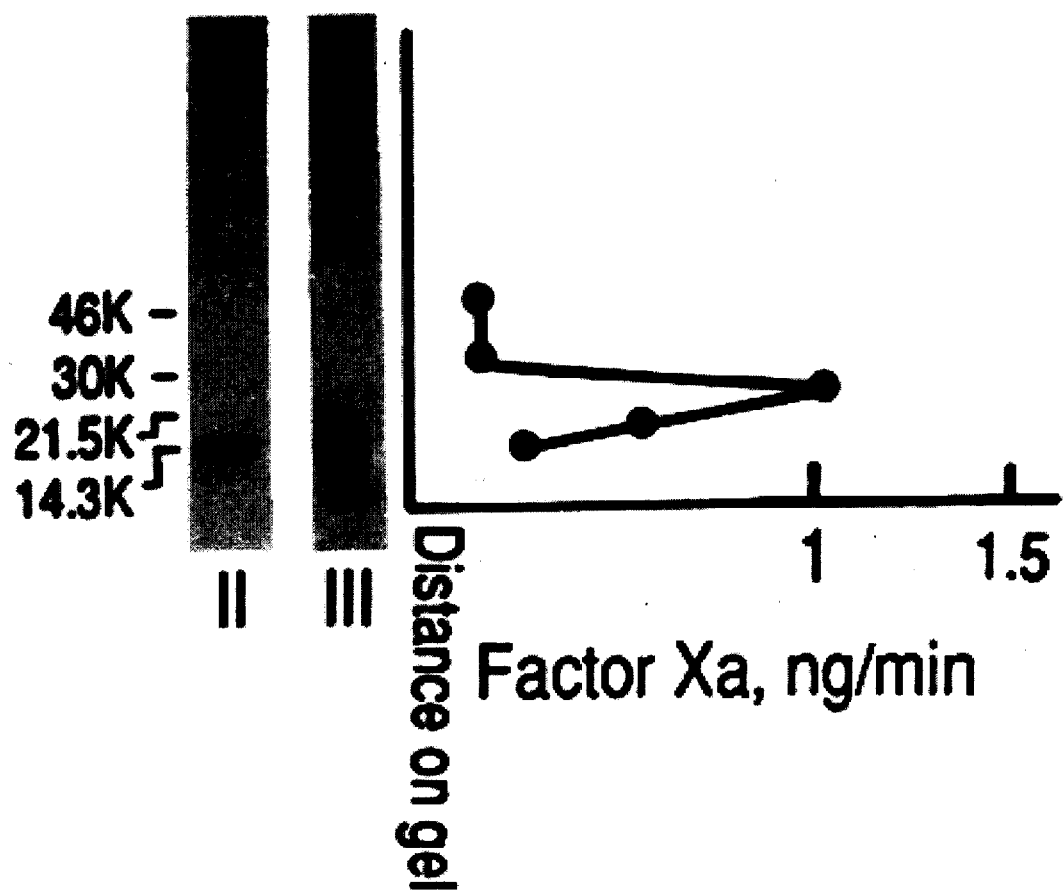

FIG. 15B: SDS-PAGE of EMAP II. Mono Q-derived, gel-eluted protein from slices of the gel which induced tissue factor in ECs (see FIG. 15A, above), was subjected again to reduced (II) or nonreduced (III and far right panel) SDS-PAGE (12.5%; e ug/lane). Protein in the gel was either visualized by silver staining (II and III), or gel-eluted material was incubated with ECs, and induction of tissue factor activity, using the Factor Xa formation assay, was studied (far right panel). Gel slices are aligned with the corresponding portion of the stained gel in lane III.

Figure 15C:
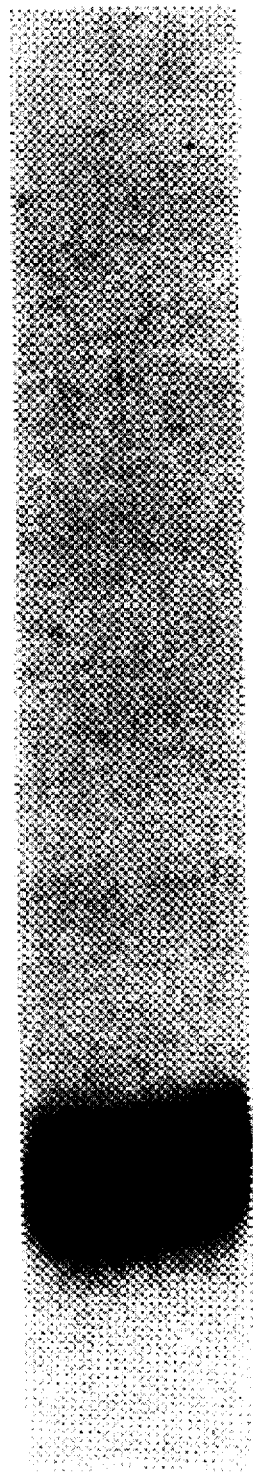

FIG. 15C: Immunoblotting of EMAP II. EMAP II purified by FPLC Mono Q and SDS-PAGE/gel elution was subjected to nonreduced SDS-PAGE (12%; 10 ug/lane), electrophoretic transfer to nitrocellulose, and immuoreactive protein in the gel was visualized using rabbit anti-mature EMAP II amino-terminal peptide IgG (2 ug/ml) followed by peroxidase-conjugated goat anti-rabbit IgG (50 ng/ml; Sigma). Molecular mass markers depict the migration of simultaneously run standard proteins: ovalbumin (46 kDa), carbonic anhydrase (30 kDa), trypsin inhibitor (21.5 kDa), and lysozyme (14.3 kDa) (Amersham Corp.).

Figure 16A:
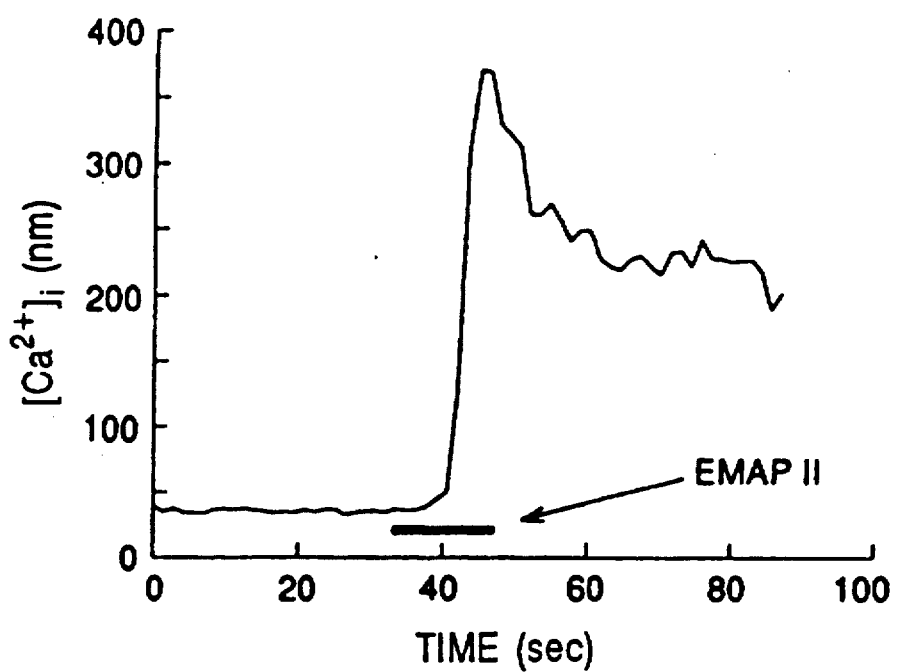

FIG. 16A: Effects of EMAP II on ECs: elevation of [Ca2+]. Confluent EC monolayers grown on glass coverslips were incubated at 37° C. with EMAP II (250 pM), and $[Ca^{2+}]_i$ was determined by fura-2AM fluorescence, as described.

Figure 16C:
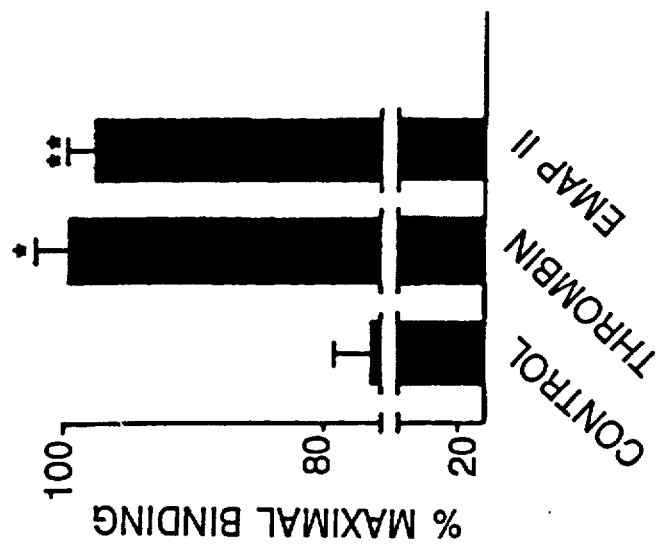
Figure 16B:
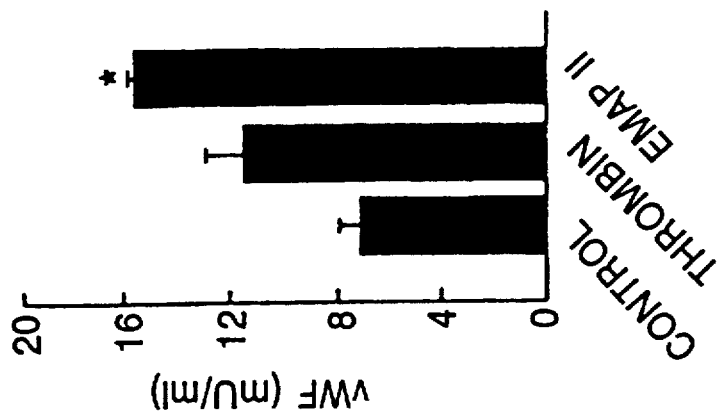

FIG. 16B: Effects of EMAP II on ECB: release of vWF. Confluent EC monolayers ($10^4$ cells/well) in M199 supplemented with heat-treated human serum (1%) were incubated at 37° C. with medium alone (control), thrombin (2 units/ml), or EMAP II (200 pM). After 15 min, supernatant was withdrawn and assayed for vWF by ELISA. The mean±S.E. of triplicate determinations is shown. * denotes p<0.01.

FIG. 16C: Effects of DIAP II on ECS: expression of P-selectin on the EC surface (C). Confluent EC monolayers ($10^4$ cells/well) in M199 were incubated at 37° C. with EMAP II as above, heat-treated EMAP II, or thrombin (2 units/ml). A radioligand binding assay was then performed by adding $^{125}$I-murine monoclonal anti-human P-selectin IgG (100 ng/ml) alone or in the presence of excess unlabeled anti-human P-selectin IgG, as described in the text. Data shown were normalized by arbitrarily assigning the value of 1 (i.e 100%) to $^{125}$I-antibody binding observed in the presence of thrombin (the maximal response), and represent mean±S.E. of triplicate determinations. * denotes p<0.001 and ** denotes p<0.005 versus control.

Figure 17A:
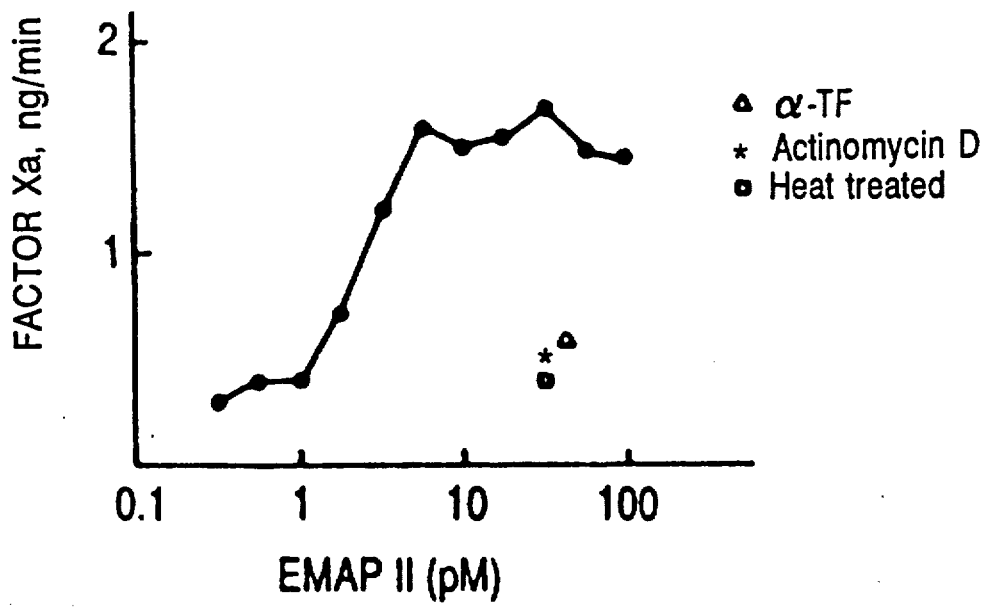

FIG. 17A: Effects of EMAP II on ECs: induction of EC tissue factor. Confluent ECs ($10^4$ cells/well) were incubated with the indicated concentration of EMAP II for 6 h at 37° C., then tissue factor activity was measured by determining Factor VIIa-dependent Factor Xa formation as described in the text. As indicated: actinomycin D (5 ug/ml) was added simultaneously with EMAP II (star): heat-treated EMAP II was adden place of active EMAP II (square): or anti-tissue factor IgG (anti-TF: 1 ug/ml) was added during the tissue factor assay (triangle). Data are reported as Factor Xa formed/min in the assay (ng/min). Note that addition of the same amount of nonimmune IgG had no effect on Factor Xa formation in the tissue factor assay. The mean of duplicate determinations is shown, and the experiment was repeated four times.

Figure 17B:
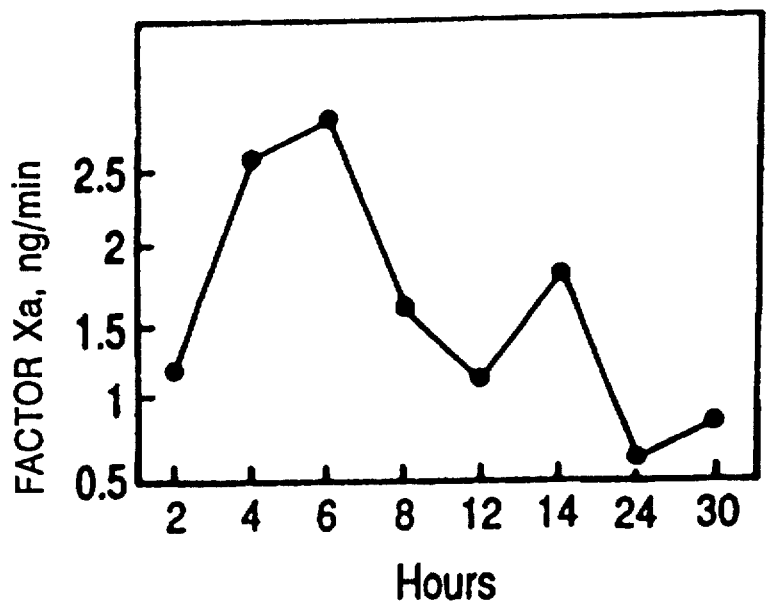

FIG. 17B: Effects of EMAP II on ECS: induction of EC tissue factor. EC monolayers (as in FIG. 17A) were incubated with II (100 pM) for the indicated times, and then the tissue factor assay was performed as described above.

Figure 17C:
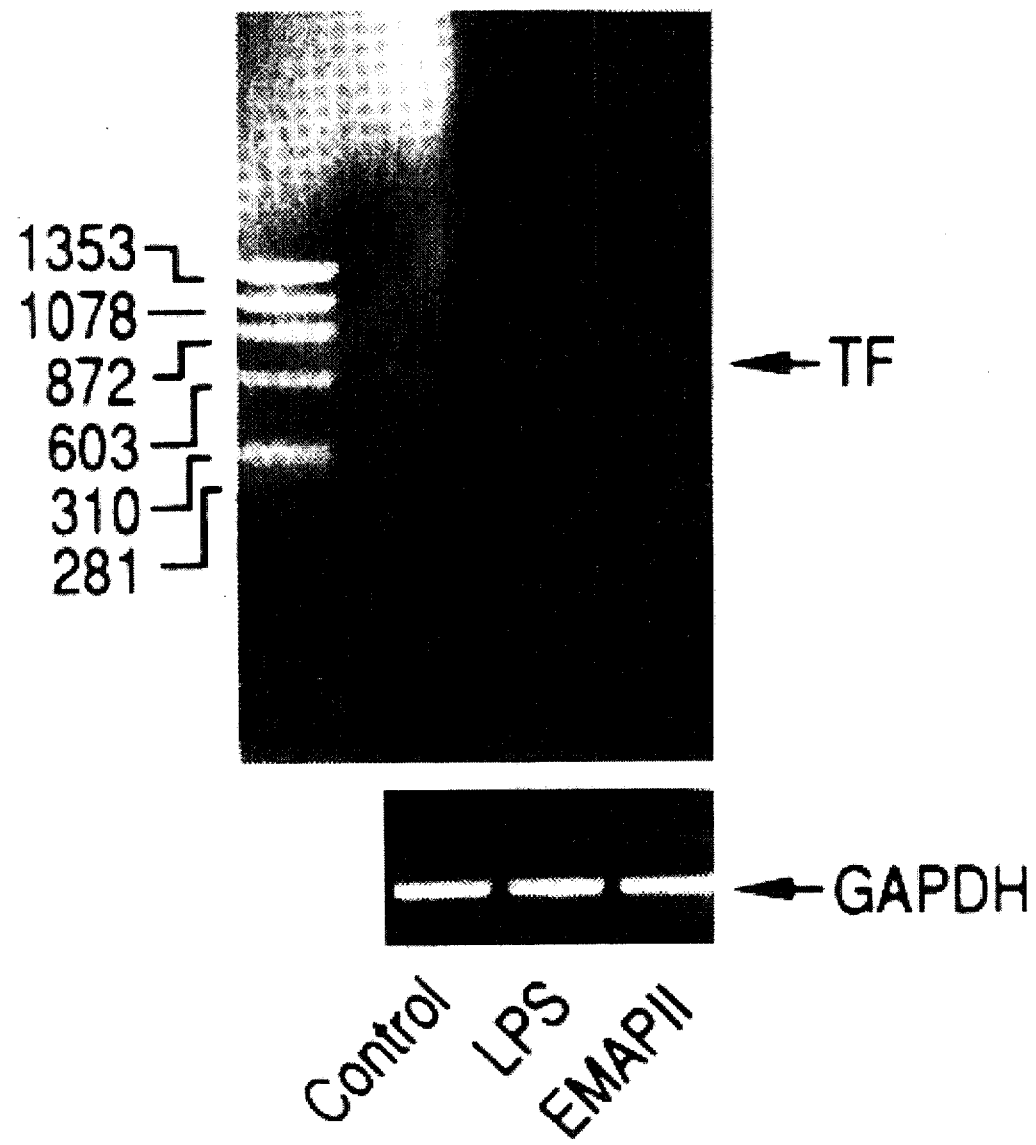

FIG. 17C: Effects of EMAP II on ECs: induction of EC tissue factor. ECs were incubated with medium alone (control), LPS (100 ng/ml), or EMAP II (100 pM) for 1 h and RNA was processed for amplification by PCR using primers for tissue factor (TF) or GAPDH. PCR was performed for 35 and 20 cycles, respectively. Migration of markers in base pairs (X174) is shown on the far left lane.

Figure 17D:
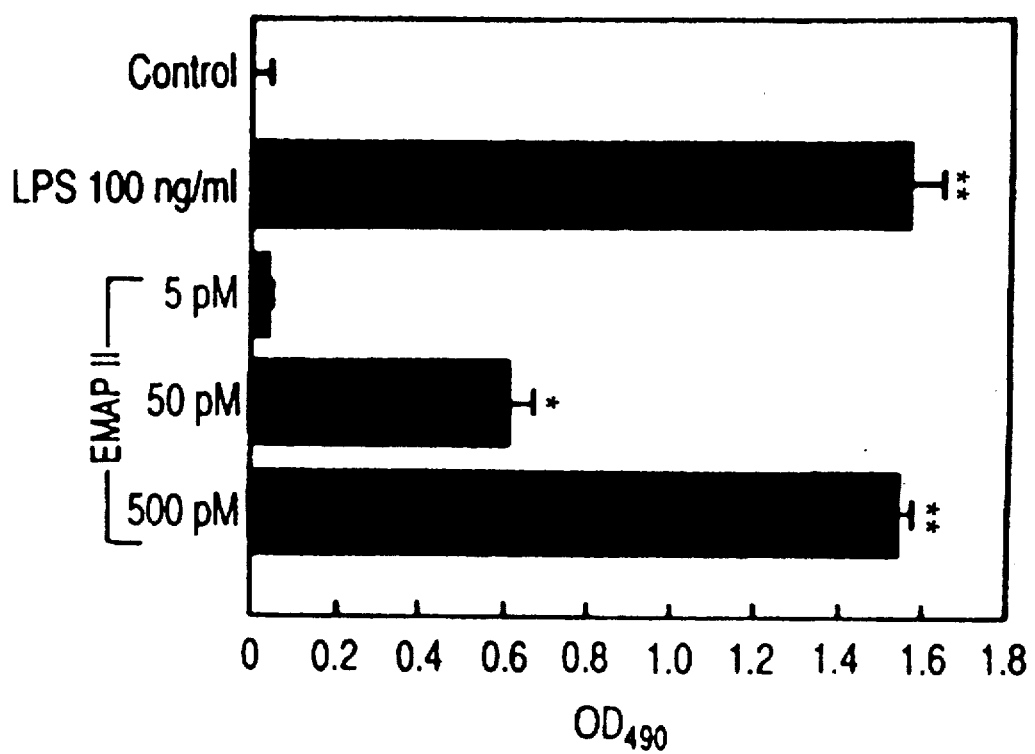

FIG. 17D: Effects of EMAP II on ECs: induction of E-selectin expression. Confluent ECs ($10^4$ cells/well) were incubated with either medium alone (control), LPS (100 ng/ml), or EMAP II (at the indicated concentration) for 4 h at 37° C. Cells were then fixed with glutaraldehyde (0.05%), blocked with albumin (3%), and exposed to mouse anti-human E-selectin IgG followed by peroxidase-conjugated goat anti-mouse IgG as described. Data are reported as absorbance at 490 nm (mean±S.E. of triplicate determinations). * denoted p<0.05 and ** denotes p<0.01.

Figure 17E:
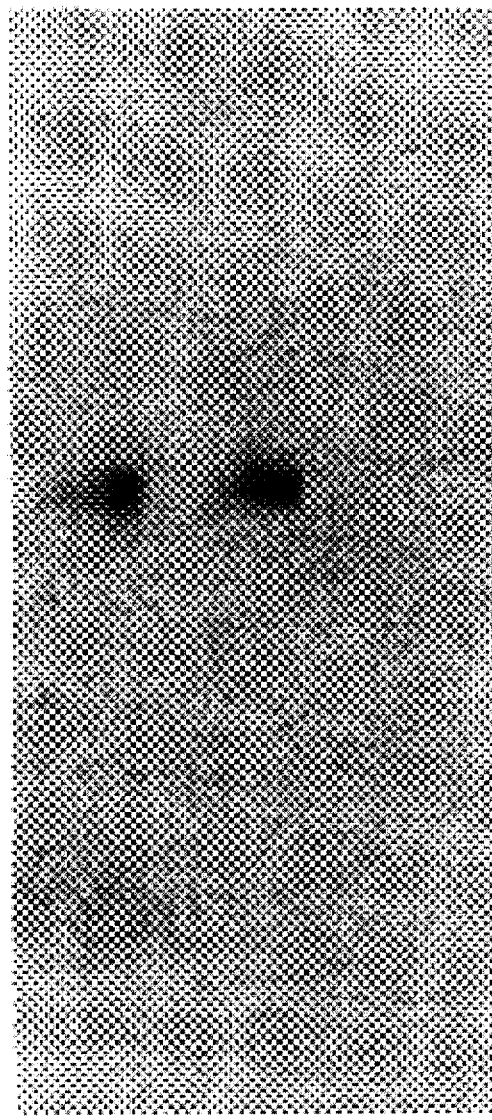

FIG. 17E: Effects of EMAP II on ECs: induction of E-selectin expression. E confluent ECs ($10^5$ cells/well) were exposed to medium alone (control), LPS (100 ng), or EMAP II (100 pM) for 4 h and were then prepared for nonreduced SDS-PAGE (4–15%). 100 ug of protein was loaded in each lane. Following electrophoresis, proteins were transferred to nitrocellulose and visualized using murine monoclonal anti-human E-selectin IgG and peroxidase-conjugated goat-anti-mouse IgG. The migration of one simultaneously electrophoresed standard protein (phosphorylase b, 97.4 kDa) is shown by the position of the arrow on the far right. Other standard proteins run included bovine serum albumin (69 kDa), ovalbumin (46 kDa), carbonic anhydrase (30 kDa), trypsin inhibitor (21.5 kDa), and lysozyme (14.3 kDa).

Figure 18A:
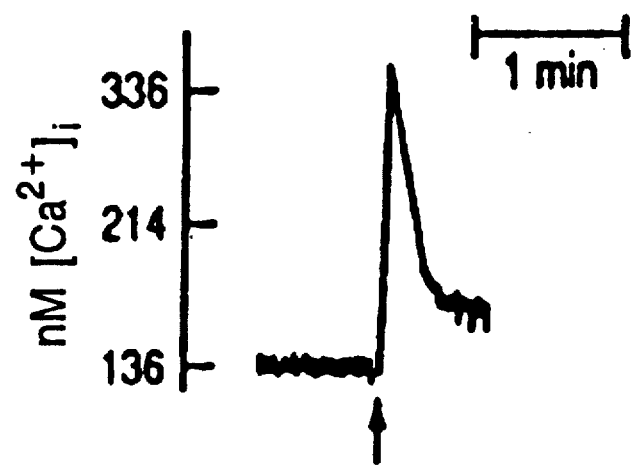

FIG. 18A: Effect of EMAP II on human PMNS: elevation of cytosolic calcium. EMAP II or heat-treated EMAP II was added to the fura-2-loaded cells ($2 \times 10^7$), and [$Ca^{2+}$], was measured as described in the text. This tracing is representative of four experiments.

Figure 18C:
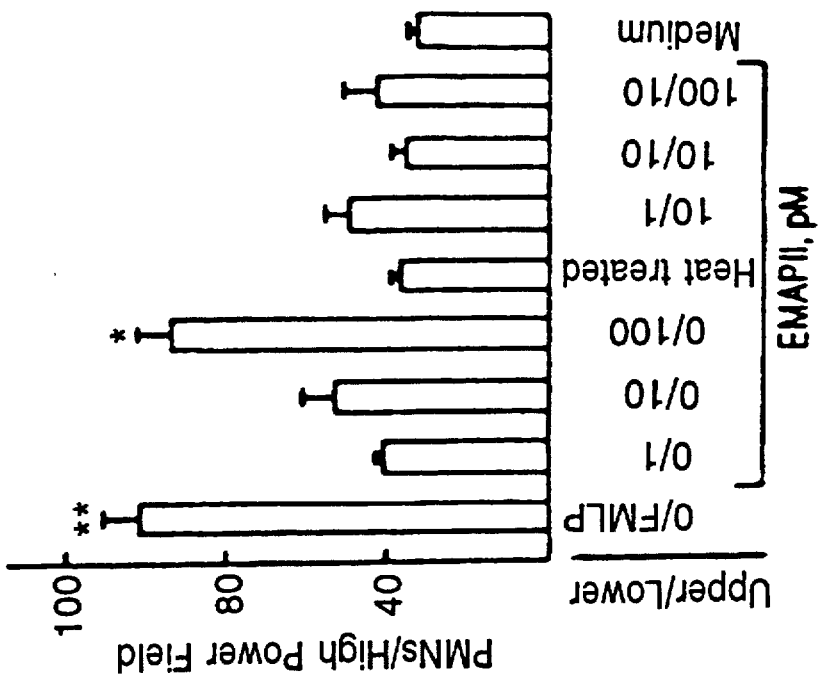
Figure 18B:
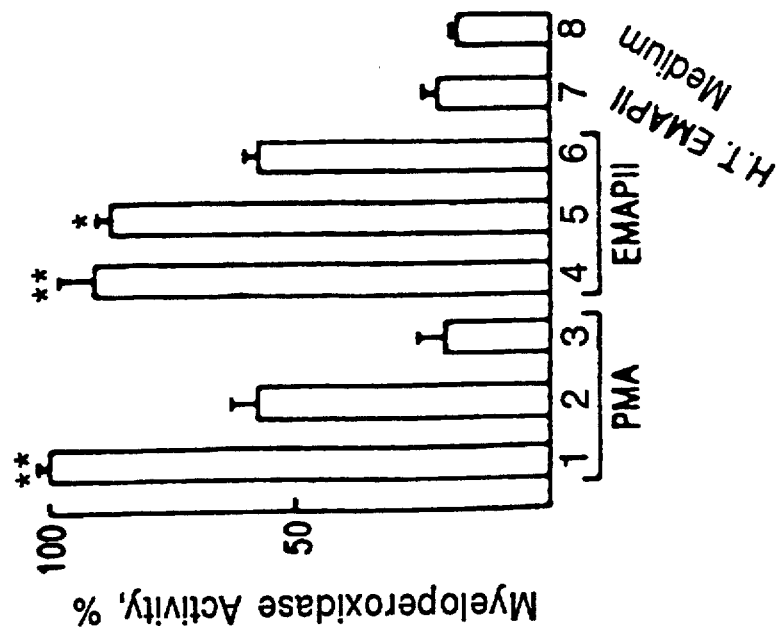

FIG. 18B: Effect of EMAP II on human PMNs: peroxidase generation. PMNs ($3 \times 10^6$ cells/ml) were incubated with either phorbol ester (1, 10 uM; 2, 5 uM; 3, 2.5 uM), EMAP II (4, 150 pM; 5, 50 pM; 6, 25 pM), heat-treated EMAP II (H.T EMAP II; 7 50 pM) or medium alone (8) for 60 min at 37° C., and peroxidase generation was measured based on reduction of TMB. Peroxidase generation by PMNs exposed to phorbol ester at 10 uM was arbitrarily defined as 100%. Data represent the mean±S.E. of triplicate determinations, and * denotes p<0.002 and ** p<0.001.

FIG. 18C: Effect of EMAP II on human PMNs: chemotaxis. PMNs ($10^4$ cells) were added to the upper compartment of chemotaxis chambers, and the indicated stimulus was added to the upper or lower compartment (upper/lower). Where indicated, fMLP ($10^6$) or heat-treated assays were performed, and mean±S.E. is shown. * denotes p<0.005 and ** denotes p<0.001 compared with wells containing medium alone.

Figure 19A:
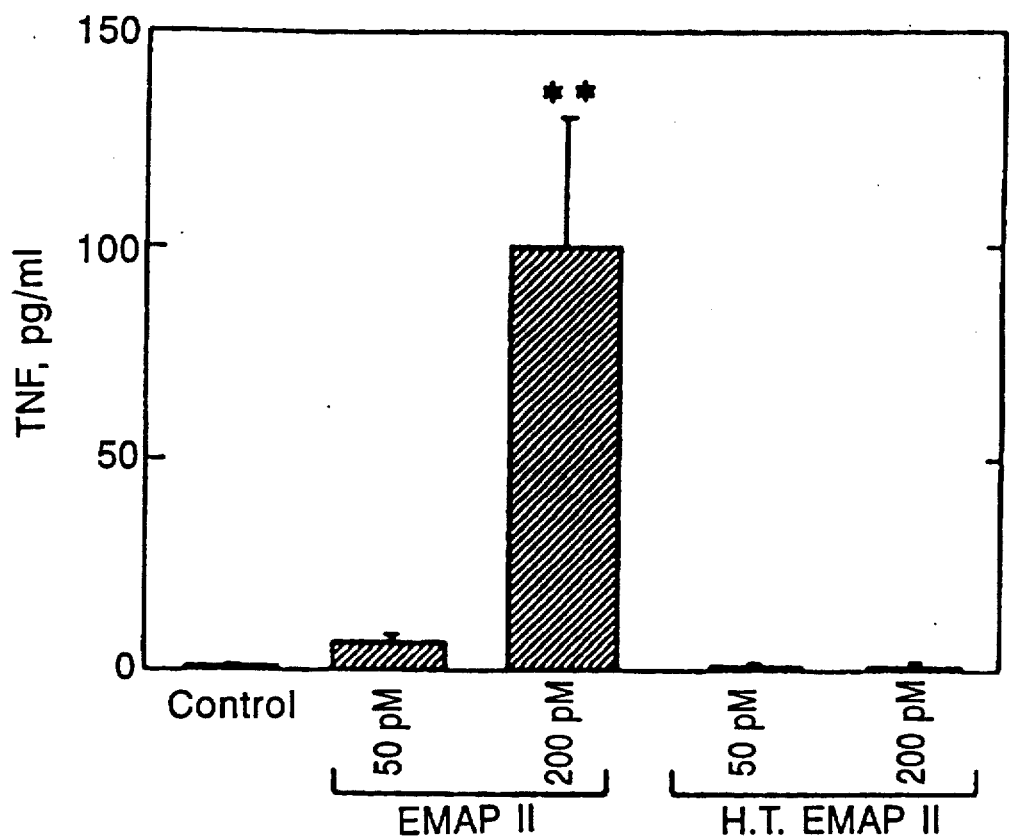

FIG. 19A: Effect of EMAP II on MPs: expression of TNF. MPs ($10^5$ cells/well) were incubated with EMAP II at the indicated concentration, and elaboration of TNFα antigen into the culture medium was monitored by ELISA after 6 h.

Figure 19B:
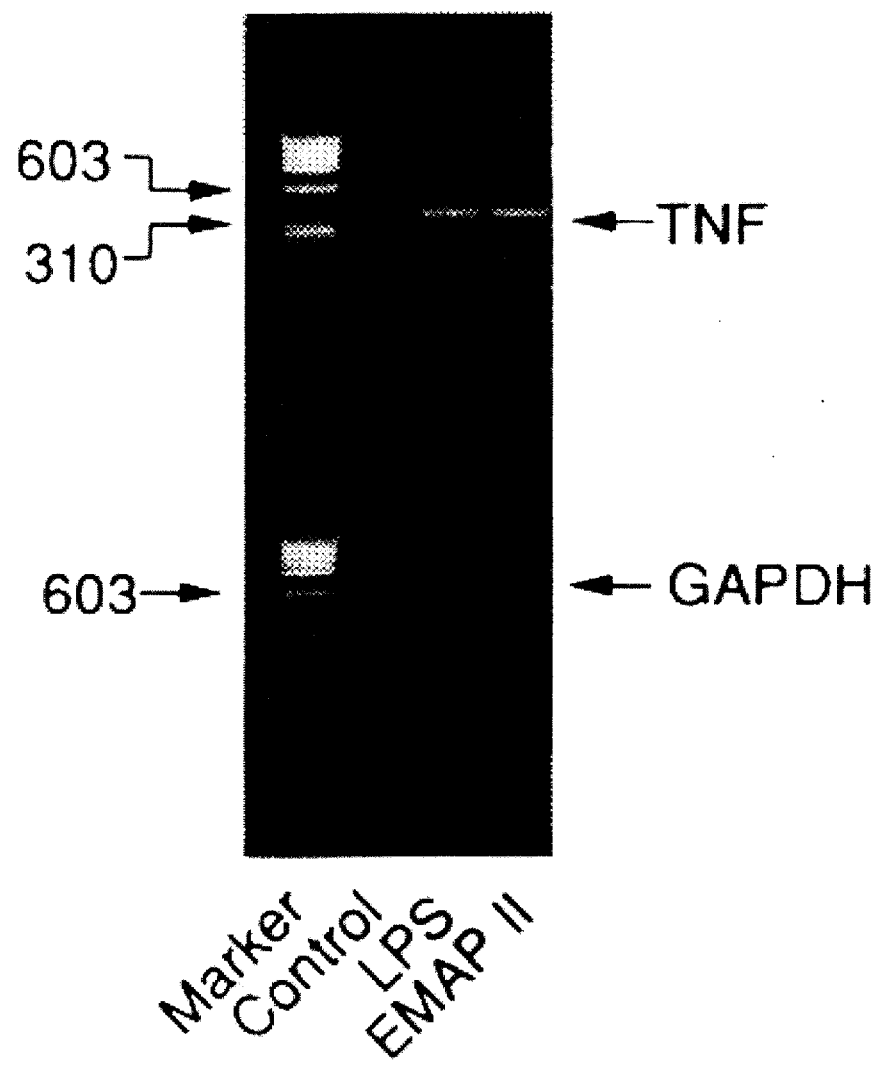

FIG. 19B: Effect of EMAP II on MPs: expression of TNF. MPs ($5 \times 10^5$) were incubated with medium alone (control), LPS (100 ng), EMAP II (150 pM), or heat-treated EMAP II (H.T. EMAP II; 150 pM), and RNA was processed for amplification by PCR using primers for TNF or GAPDH. PCR was performed for 30 and 20 cycles for TNF and GAPDH, respectively. Migration of markers (X174) base pairs is shown on the far left lane.

Figure 19C:
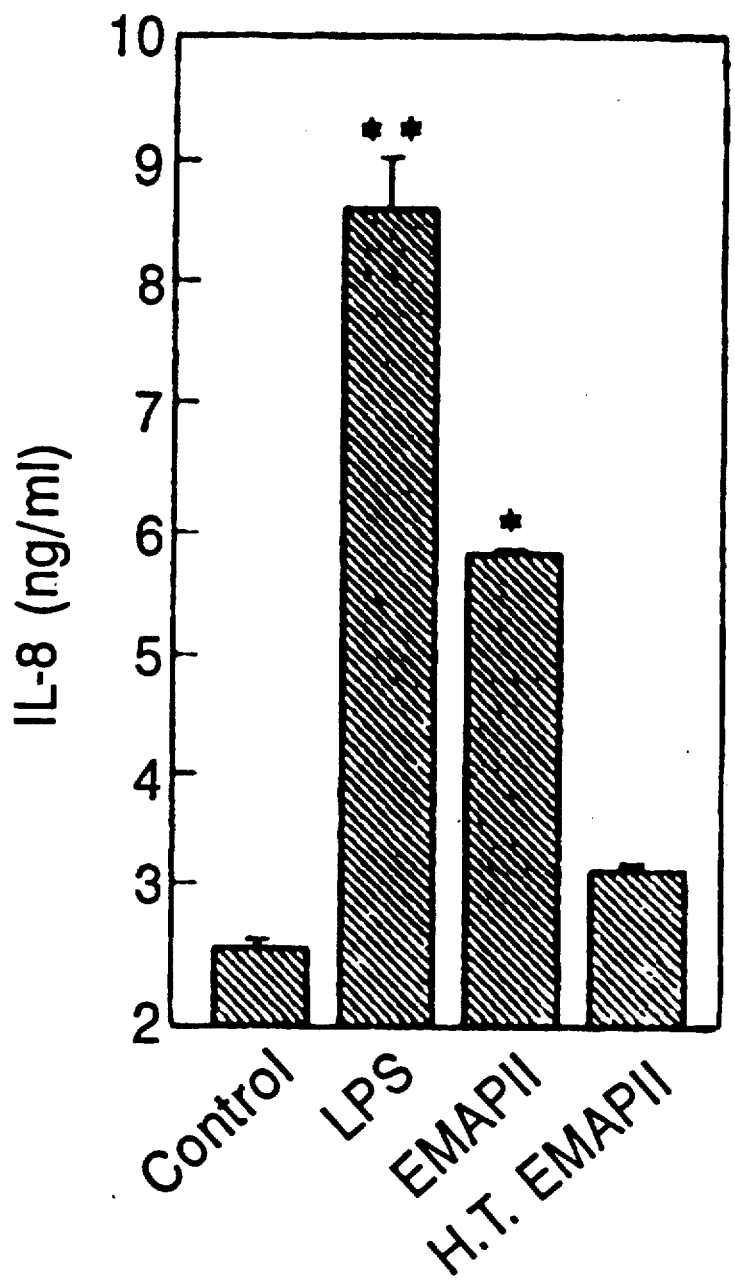

FIG. 19C: Effect of EMAP II on MPs: expression of IL-8. MPs (105 cells/well) were incubated with medium alone (control), EMAP II (150 pM), LPS (100 ng), or heat-treated EMAP II (H.T. EMAP II: 150 pM) for 8 h. Supernatants were analyzed by ELISA for IL-8 antigen. The mean±S.E. of triplicate determinations is shown, and * denotes p<0.004 and ** denotes p<0.001 versus control.

Figure 19D:
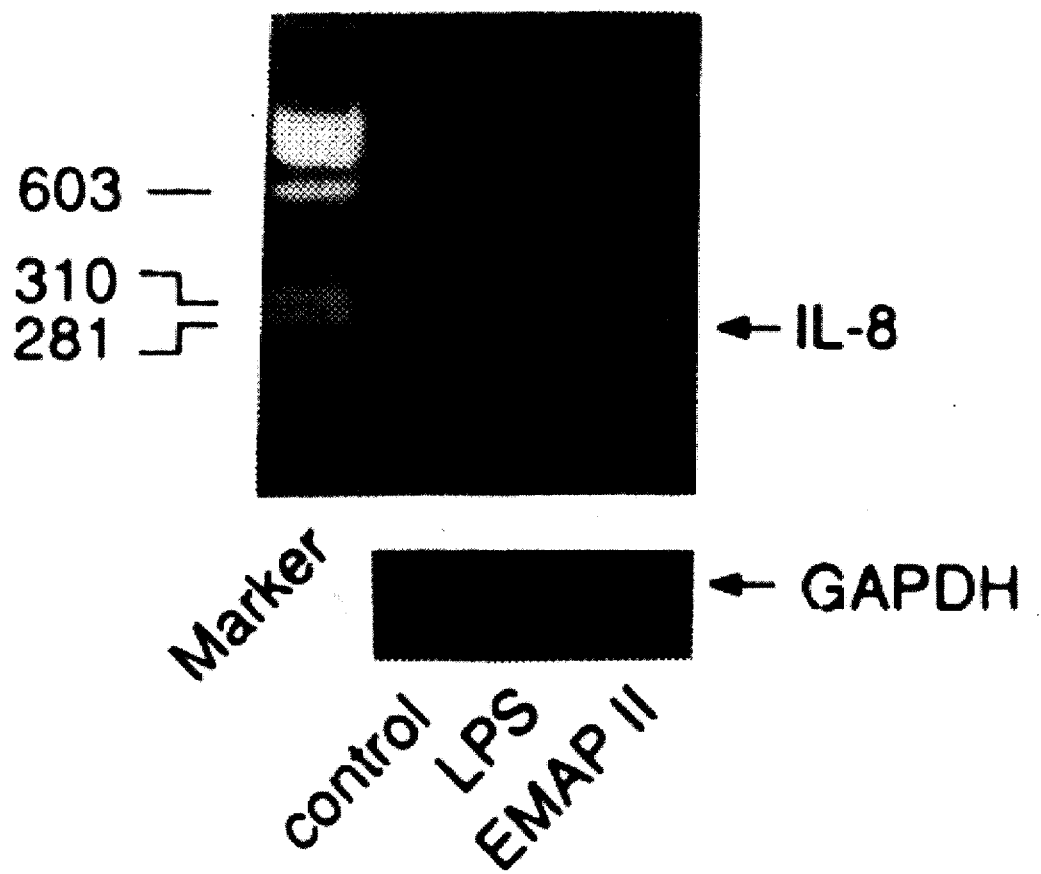

FIG. 19D: Effect of EMAP II on MPs: IL-8. MPs ($10^5$ cells/well) were incubated with medium alone, LPS (100 ng) or EMAP II (150 pM) for 2 h, and RNA was processed for amplification by PCR using primers for IL-8 or GAPDH. PCR was performed with thermocyte settings described in the text. Migration of markers in base pairs is shown on the far left lane.

Figure 19F:
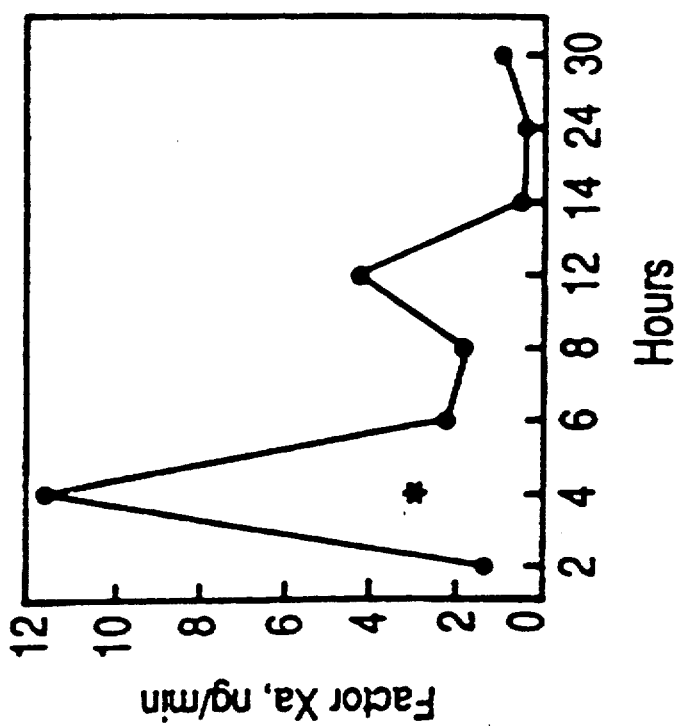
Figure 19E:
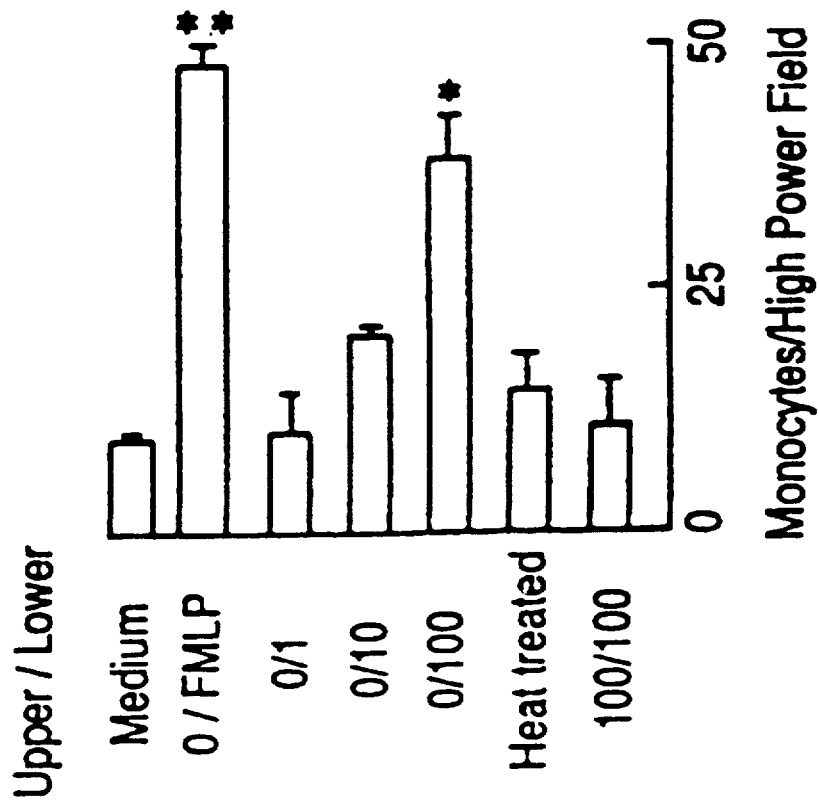

FIG. 19E: Effect of EMAP II on MPs: chemotaxis. Mps ($10^3$ cells/well) were added to the upper compartment of chemotaxis chambers and the indicated stimulus (concentration in pm) was added to the upper or lower compartment (upper/lower). fMLP ($10^6$) or heat-treated EMAP II (100 pM) were added only to the lower compartment. Cell migration assays were performed, and mean±S.E. is shown. * denotes p<0.05 and ** denotes p<0.002 compared with wells containing medium alone.

FIG. 19F: Effect of EMAP II on MPs: expression of tissue factor. MPs ($5 \times 10^4$ cells/well) were incubated with EMAP II (100 pM) for the indicated times at 37° C., and then the tissue factor assay was performed and Factor Xa formation (mean±S.E. of triplicates) is shown. * denotes MPs incubated with EMAP II (100 pM) for 2 h which were assayed for tissue factor activity in the presence of anti-tissue factor IgG (1 ug/ml).

Figure 19G:
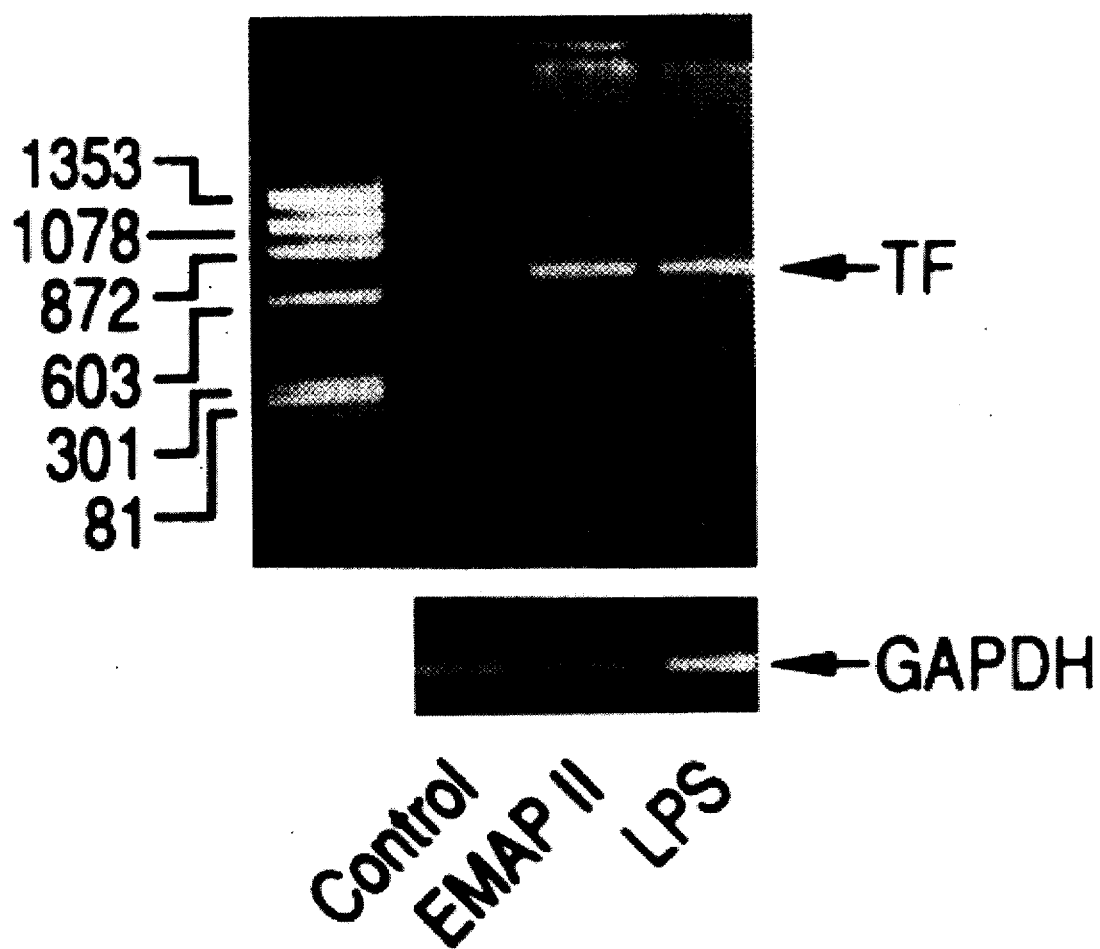

FIG. 19G: Effect of EMAP II MPs: expression of tissue factor. MPs ($5 \times 10^5$) were incubated with medium alone (control), EMAP II (150 pM), or LPS (100 ng) for 1 h, and RNA was processed for amplification by PCR using primers for tissue factor (TF) or GAPDH. PCR was performed for 40 and 25 cycles, respectively. Migration of markers in base pairs is shown on the far left lane.

Figure 19H:
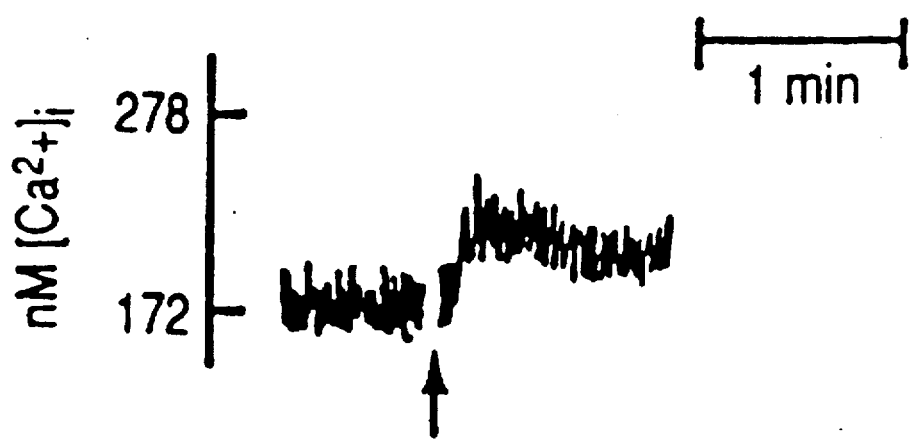

FIG. 19H: Effect of EMAP II on MPs: ionized cytosolic calcium. EMAP II (200 pM) was added to fura-2-loaded cells ($2 \times 10^7$ ml), and [$Ca^{2+}$], was measured as described in the text. Each tracing is representative of four experiments.

Figure 20A:
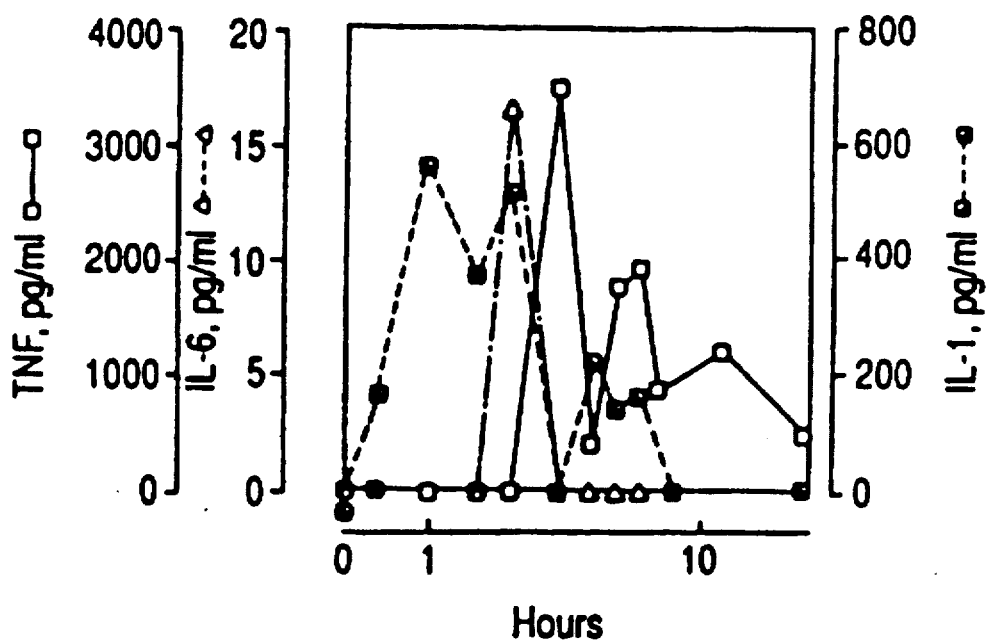

FIG. 20A: Systemic infusion of EMAP II into C3H/HeJ mice: cytokine induction. Mice were infused via the tail vein with EMAP II (10 ug), and at the indicated times mice were sacrificed and anticoagulated blood samples were obtained. Plasma samples were assayed for IL-1a (half-filled box), IL-6 (open triangle), or TNFα (open box). The mean of duplicate determinations is shown, and this experiment is representative of four.

Figure 20B:
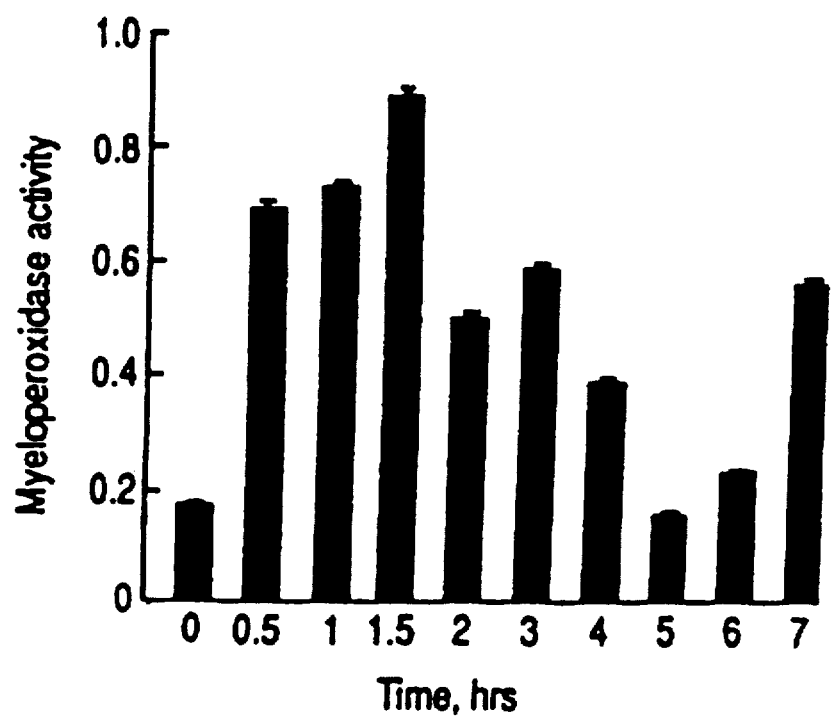

FIG. 20B: Systemic infusion of EMAP II into C3H/HeJ mice: pulmonary leukostasis. Mice were infused with EMAP II (5 ug/animal) or saline, and at the indicated times lung tissue was harvested and myeloperoxidase activity was determined as described in the text. The mean+S.E. of triplicate determinations is shown, and the experiment was repeated three times.

Figure 20C:

FIG. 20C: Systemic infusion of EMAP II into C3H/HeJ mice: pathologic lung changes. Mice were infused with saline alone and then 4 h later were sacrificed; lung tissue was harvested, fixed, and stained with hematoxylin/eosin. ×300 magnification.

Figure 20D:

FIG. 20D: Systemic infusion of EMAP II into C3E/HeJ micespathologic lung changes. Mice were infused with EMAP II (10 ug) in saline, and then 4 h later were sacrificed; lung tissue was harvested, fixed, and stained with hematoxylin/eosin. ×300 magnification.

Figure 21A:
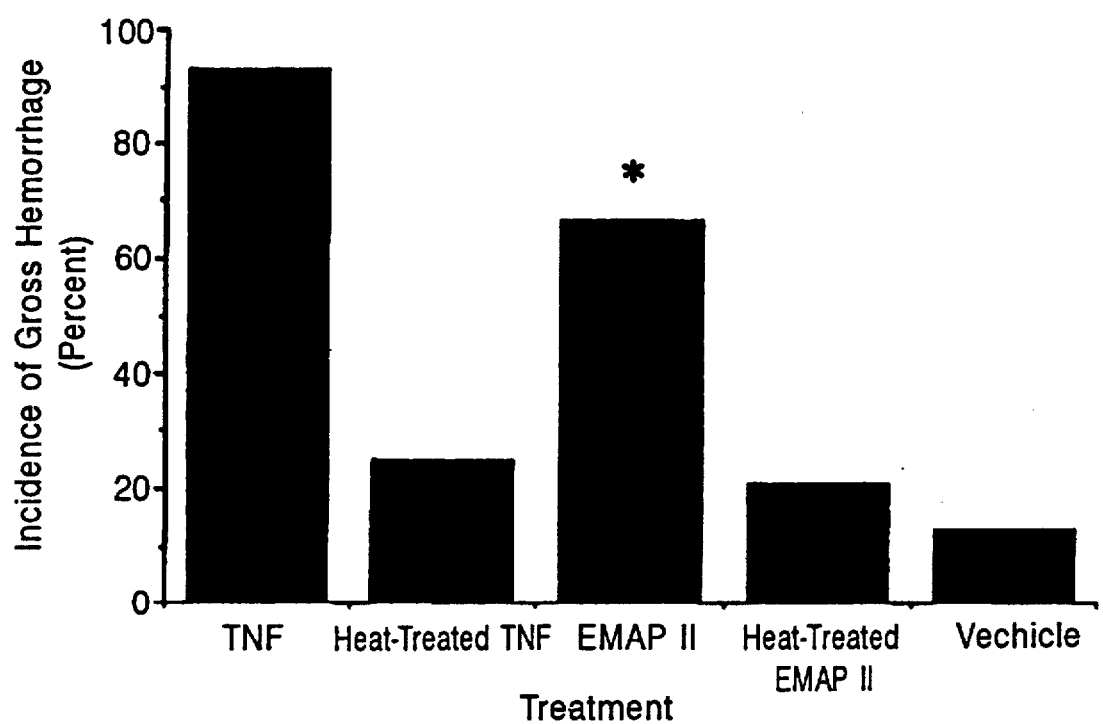

FIG. 21A: Intratumor injection of EMAP II into Meth A sarcomas: induction of hemorrhagic changes. Meth A tumors (7 days post-inoculation of Meth A cells) were administered by a single intratumor injection (0.1 ml) of either TNF (5 ug/tumor; n=15), heat-treated TNF (5 ug/tumor; n=12), EMAP II (10 ug/tumor; n=14), or vehicle alone (phosphate-buffered saline/bovine serum albumin (0.1%); n=8; all cytokines were dissolved in this vehicle). A, 6 h after the injection, mice were sacrificed, and tumors dissected and graded for the presence or absence of hemorrhage.

Figure 21B:
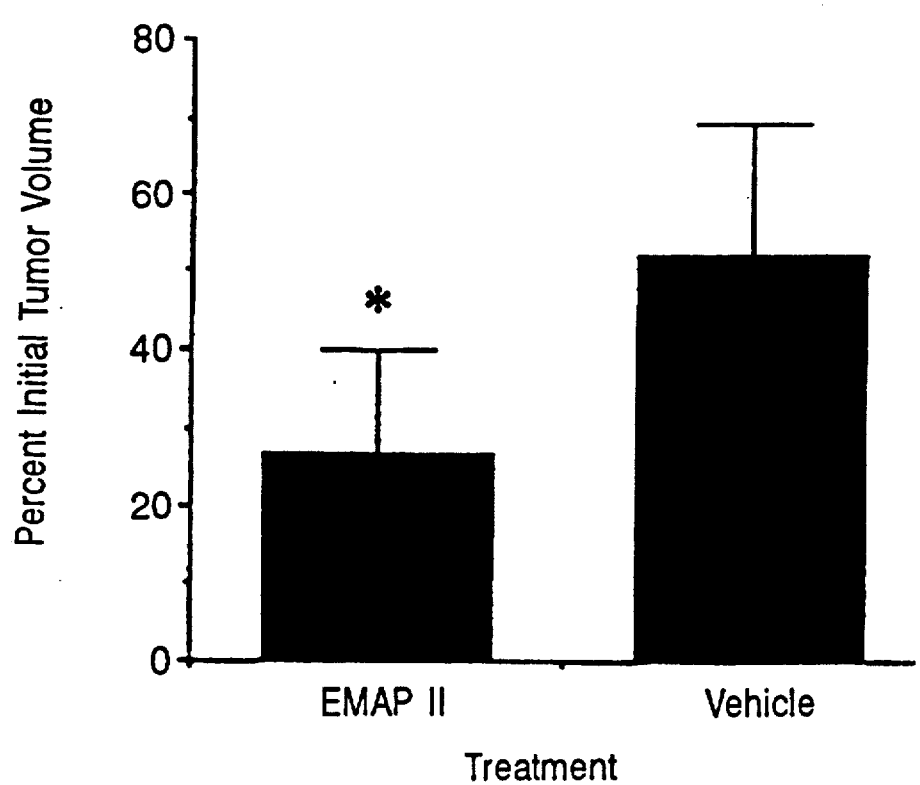

FIG. 21B: Intratumor injection of EMAP II into Meth A sarcomas: decrease in tumor volume (B). Changes in tumor volume following treatment of Meth A tumors with either EMAP II (10 ug; n=5) or vehicle alone (n=6) determined as described in the text on the second day following treatment. The results, reported as percent initial tumor volume, are given as means±S.D., and * denoted p<0.05 (Student's t test). Note that control Meth A tumors are beginning to spontaneously regress, as described previously (4), although the degree of regression is less than that observed with tumors treated with EMAP II.

Figure 22A:
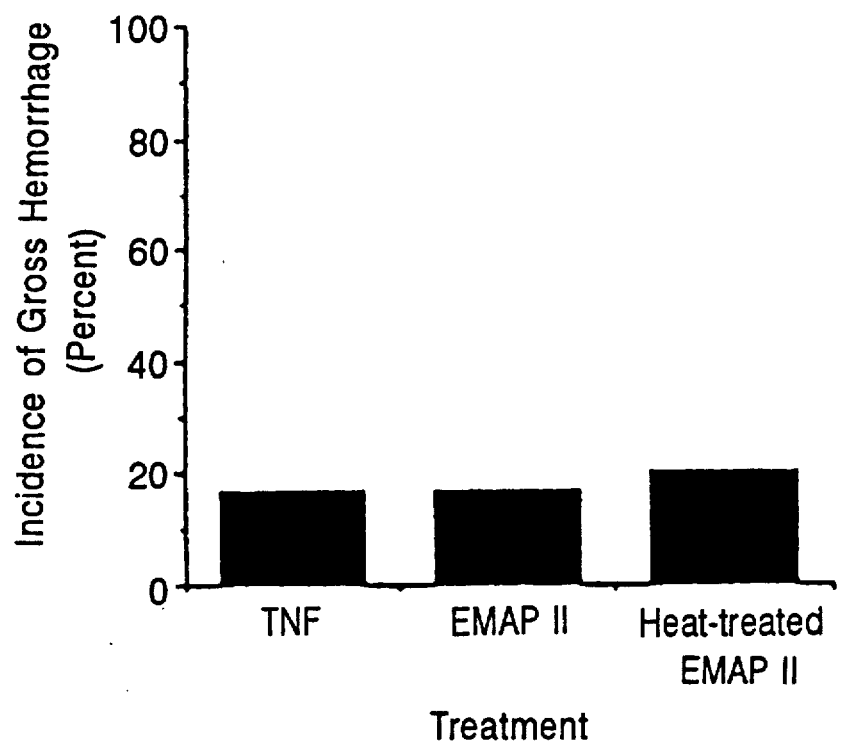

FIG. 22A: Effects of combined cytokine treatments on murine mammary carcinomas: induction of hemorrhage. Mammary carcinomas (6 days post-inoculation of mice with tumor cells) received a single intratumor injection (0.1 ml) of either TNF (5 ug/tumor; n=6), EMAP II (10 ug/tumor; n=6), or heat-treated EMAP II (10 ug/tumor; n=5). After 6 h, tumors were excised for visual assessment of the presence/absence of hemorrhage. There is no statistically significant difference between the groups.

Figure 22B:
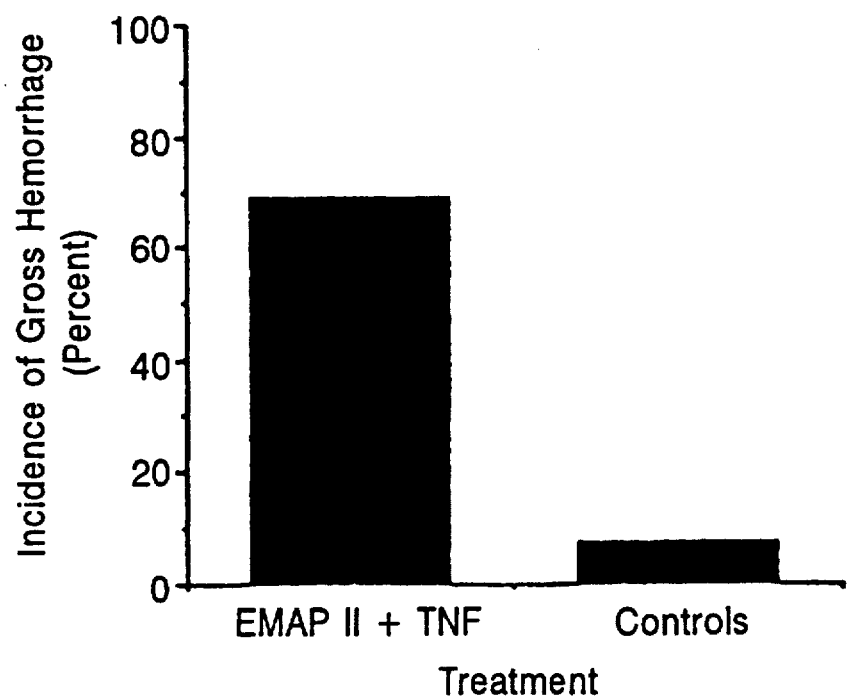

FIG. 22B: Effects of combined cytokine treatments on murine mammary carcinomas: induction of hemorrhage. Mammary carcinomas (as in FIG. 22A above) received an intratumor injection of either EMAP II (10 ug/tumor) or heat-treated EMAP II (10 ug/tumor) followed ~15 h later by a tail vein injection of either TNF (5 ug/animal) or heat-treated TNF (5 ug/animal). Mice were sacrificed 6 h after the tail vein injection, and tumors were scored for the presence/ absence of gross hemorrhage. Only the group receiving active EMAP II followed by active TNF had an appreciable incidence of hemorrhage (69.2%; n=13), while groups receiving paired injections including one or both heat-inactived cytokines showed only low base line hemorrhage (7.7%; n=13; p<0.005 by x2 analysis).

Figure 22C:

FIG. 22C: Effects of combined cytokine treatments on murine mammary carcinomas: pathologic changes in the tumor bed. Mammary carcinomas (prepared as above) received an injection of vehicle (control) followed by tail vein injection if TNF (5 ug/animal). Twelve h after TNF injection, tumors were excised, fixed, and stained as described. Magnification: ×300.

Figure 22D:
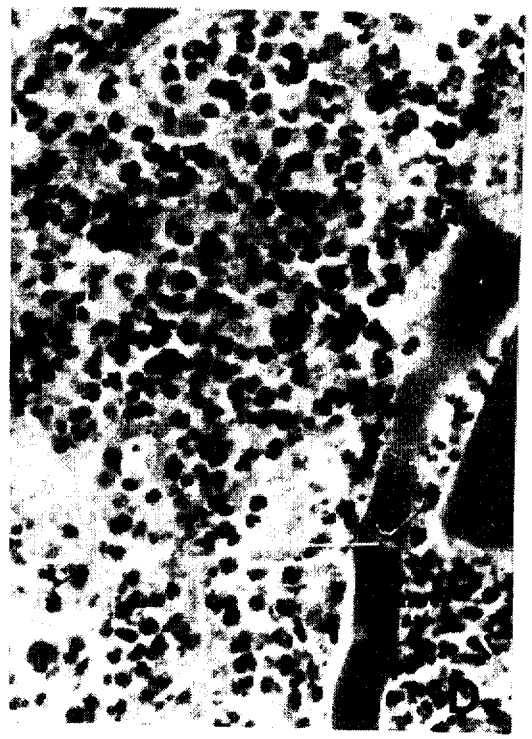

FIG. 22D: Effects of combined cytokine treatments on murine mammary carcinomas: pathologic changes in the tumor bed. Mammary carcinomas (prepared as above) received an injection of EMAP II (10 ug/tumor; D), followed by tail vein injection if TNF (5 ug/animal). Twelve h after TNF injection, tumors were excised, fixed, and stained as described. Magnification: ×300.

Figure 22E:
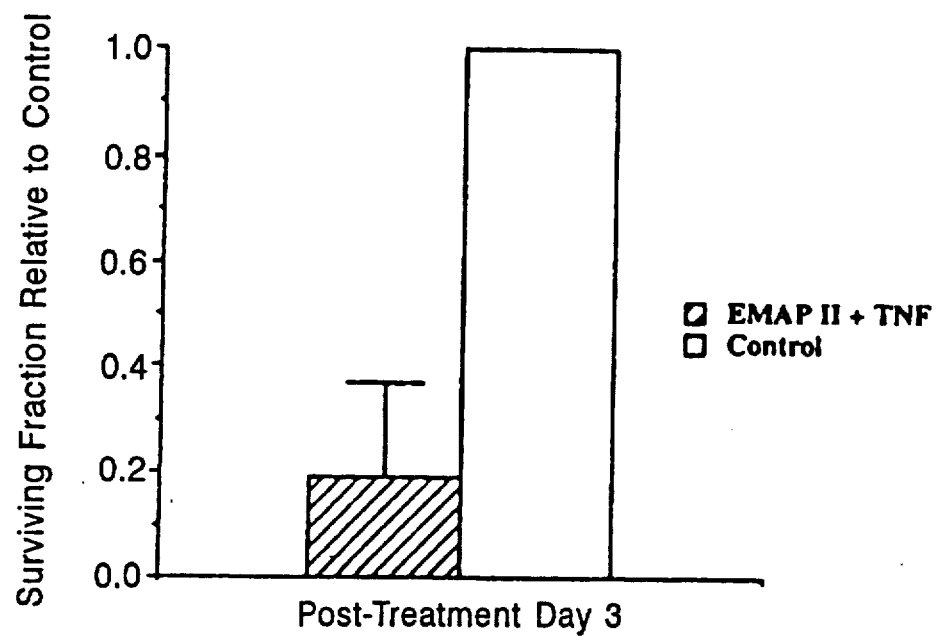

FIG. 22E: Effects of combined cytokine treatments on murine mammary carcinomas: reduction in clonogenic survival of tumor cells. Mammary carcinomas (prepared as above) received local EMAP II (10 ug/tumor; n=6) or heat-treated EMAP II as control (10 ug/tumor; n=6), followed approximately 15 h later by a tail vein injection of TNf (5 ug) in all animals. Tumors were excised 72 h later, processed to obtain diluted cell suspensions, counted, and incubated for 4 days in culture medium as described. After this incubation period, the number of dividing colonies was counted by a blinded observer and the surviving clonogenic fraction calculated.

Figure 22F:
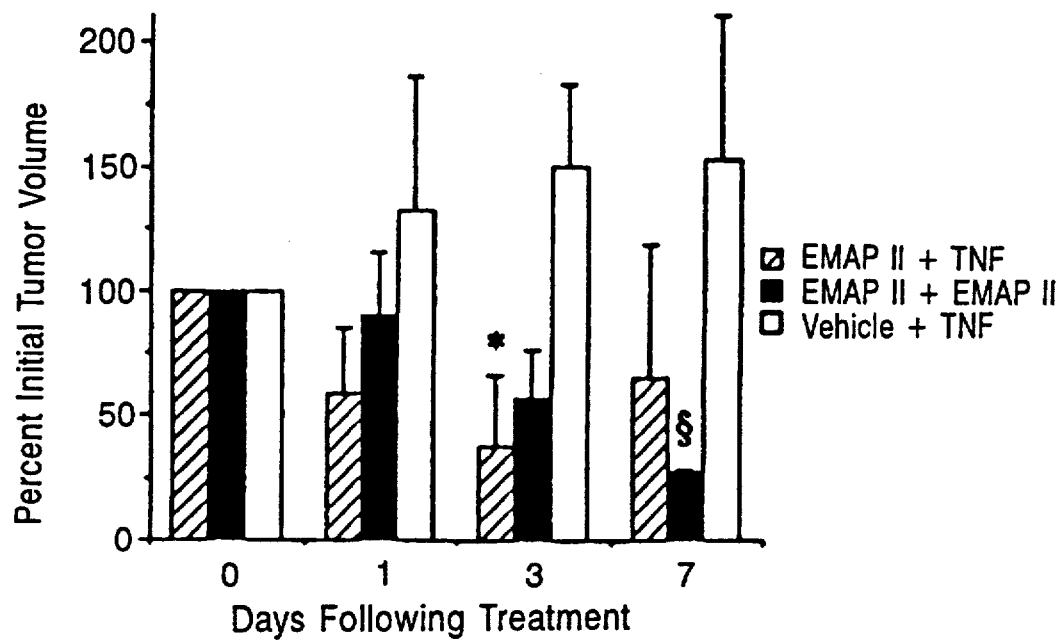

FIG. 22F: Effects of combined cytokine treatments on murine mammary carcinomas: and reduction in tumnr volume. Mammary carcinomas (grown as above) were injected locally with either EMAP II (10 ug/tumor) or vehicle alone, followed ~15 h later by tail vein infusion of TNF (5 ug/animal) or EMAP II (20 ug/animal). Tumor volume was evaluated on days 0 (the day of the tail vein injection), 1, 3, and 7, and data are reported as percent initial tumor volume (calculated for each tumor and displayed as mean+S.E. for each treatment group). tumors receiving local EMAP II+systemic TNF (n=13) had regressed by day 3, with respect to the control group (which received local vehicle+ systemic TNF; n=4; * denotes p<0.007), whereas tumors receiving local EMAP II+systemic EMAP II (n=2) reached a statistically significant difference in tumor volume on the seventh day after treatment (§ denotes p<0.021 versus control). Statistical comparisons were made by ANOVA with post-hoc Student's t tests.

DETAILED DESCRIPTION OF THE INVENTION

The following standard abbreviations are used throughout this application to refer to nucleosides and nucleotides:

C = cytosine
A = adenosine
T = thymidine
G = guanosine

The following standard single letter code abbreviations are used throughout this application to refer to amino acids: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp; and Y, Tyr.

The following abbreviations are also used throughout this application:

TNF=tumor necrosis factor; vWF=von Willebrand Factor; PCR=polymerase chain reaction; EC=endothelial cell; EMAP=endothelial-monocyte activating polypeptide; VPF/VEGF=vascular permeability factor/vascular endothelial growth factor; GAPDH=glyceraldehyde phosphate dehydrogenase; fMLP=formyl-methionyl-leucinyl-phenylalanine; PMN=polymorphonuclear leukocyte; MP or mononuclear=mononuclear phagocyte; IL=interleukin; IL-1=interleukin 1; Meth A=methylcholanthrene A-induced murine fibrosarcoma; TMB=3,3',5,5'-tetramethylbenzidine; DSS= disuccinimidyl suberate; $[Ca^{2+}]_i$=cytosolic free calcium concentration.

Throughout this application, various references are referred to within parenthesis. Disclosures of these publications in their entireties are hereby incorporated by reference into this application to more fully describe the state of the art to which this invention pertains. Full bibliographic citation for these references may be found at the end of this application, preceding the sequence listing and the claims.

This invention provides a purified endothelial monocyte activating polypeptide II (EMAP II).

This invention further provides an endothelial monocyte activating polypeptide II (EMAP II) having an apparent molecular weight of about 20,000 Daltons. More particularly, the EMAP II has an apparent molecular weight between about 18,000 Daltons and about 22,000 Daltons.

In a specific embodiment of this invention the endothelial monocyte activating polypeptide (EMAP II) is murine endothelial monocyte activating polypeptide (EMAP II).

In an embodiment of this invention endothelial monocyte activating polypeptide II (EMAP II) comprises the sequence Gly-Lys-Pro-Ile-Asp-Ala-Ser-Arg-Leu-Asp-Leu-Arg-Ile-Gly-Xaa-Ile-Val-Thr-Ala-Lys (SEQ ID NO. 1). In a specific embodiment, Gly-Lys-Pro-Ile-Asp-Ala-Ser-Arg-Leu-Asp-Leu-Arg-Ile-Gly-Xaa-Ile-Val-Thr-Ala-Lys (SEQ ID NO. 1) is the sequence of the N-terminal twenty amino acid residues.

This invention provides an antibody capable of binding to endothelial monocyte activating polypeptide II. This antibody may be a polyclonal antibody. Alternatively, it may be a monoclonal antibody.

This invention further provides a method of obtaining purified endothelial monocyte activating polypeptide II comprising, a) obtaining conditioned medium containing Meth A cells; b) purifying the medium from Meth A cells; c) applying the purified medium to a cation exchange resin; d) step-eluting from the cation exchange resin and pooling fractions with $OD_{280}>0.05$; e) applying the pooled fractions to an FPLC column; and f) eluting with an ascending salt gradient, thereby obtaining purified endothelial monocyte activating polypeptide II.

This invention also provides a method of obtaining an antibody to purified endothelial monocyte activating polypeptide II comprising a) immunizing a rabbit with Gly-Lys-Pro-Ile-Asp-Ala-Ser-Arg-Leu-Asp-Leu-Arg-Ile-Gly-Cys-Ile-Val-Thr-Ala-Lys (SEQ ID NO. 2) coupled to keyhole limpet hemocyanin; and b) obtaining purified IgG from the rabbit. In a specific embodiment, the antibody is a polyclonal antibody.

This invention provides a method of detecting the presence in a sample of EMAP II comprising a) adding cells to a to a first chamber; b) adding the sample to a second chamber which is separated from the first chamber by a membrane; c) visualizing migrating cells; d) counting the migrating cells; and e) determining the presence of EMAP II. In an embodiment, the cells are mononuclear phagocytes. In another embodiment, the cells are polymorphonuclear leukocytes.

This invention also provides a method of detecting the presence in a sample of EMAP II comprising a) injecting the sample into an animal footpad; and b) detecting an inflammatory response, thereby indicating the presence of EMAP II. In a preferred embodiment the animal footpad is a mouse footpad.

This invention also provides a method of detecting the presence in a sample of EMAP II comprising an immunoprecipitation step.

This invention also provides a method of detecting the presence in a saiple of EMAP II comprising a) contacting cells with the sample; and b) assaying for tissue factor activity, thereby indicating the presence of endothelial monocyte activating polypeptide II. In a specific embodiment the cells are endothelial cells. In another specific embodiment the cells are monocytes.

This invention also provides a method of inducing chemotaxis comprising a) adding cells to a to a first chamber; and b) adding a chemotaxis-inducing effective amount of EMAP II to a second chamber which is separated from the first chamber by a membrane, thereby inducing chemotaxis of the cells. In an embodiment, the cells are mononuclear phagocytes. In another embodiment the cells are polymorphonuclear leukocytes.

This invention provides a method of inducing inflammation in a subject comprising injecting an inflammation-inducing effective amount of endothelial monocyte activating polypeptide II into the footpad of the subject. In a specific embodiment the subject is a mouse.

This invention also provides a method of inducing tissue factor comprising contacting cells with a tissue factor-inducing effective amount of endothelial monocyte activating polypeptide II. In a specific embodiment the cells are endothelial cells. In another specific embodiment the cells are monocytes.

This invention further provides an effector cell activating protein comprising a polypeptide having an amino acid sequence wherein at least four amino acid residues are the same as Arg-Ile-Gly-Arg-Ile-Val-Thr (SEQ ID NO. 3) (RIGRIVT) and are in the same relative positions. For example, AILRQVT (SEQ ID NO. 12) has at least four amino acid residues that are the same as RIGRIVT and in the same relative positions because AILRQVT matches RIGRIVI in positions 2, 4, 6 and 7. The protein may have any number of amino acid residues as long as any seven-residue segment of the protein has at least four residues that are the same as RIGRIVT and in the same positions relative to each other. For example, LAILRQVT has four residues that are the same as RIGRIVT and are in the same relative positions because LAILRQVT matches RIGRIVT at positions 3, 5, 7 and 8 of LAILRQVT. In contrast, RGRIVTI has all residues the same as RIGRIVT (SEQ ID NO. 13) but only one residue is in the same relative position because RGRIVTI matches RIGRIVT only in position 1. In an embodiment, at least five amino acid residues are the same as RIGRIVT and are in the same relative positions. In a more specific embodiment at least six amino acid residues are the same as RIGRIVT and are in the same relative positions. A more specific embodiment comprises RIGRIVT.

In an embodiment the effector cell activating protein has at least seven amino acids. In a further embodiment the effector cell activating protein has between about 7 and about 16 amino acids.

In a specific embodiment, the effector cell activating protein is labeled. In an embodiment, the label is a radioactive label. In a preferred embodiment, the radioactive label is $^{125}I$.

In an embodiment of this invention, the effector cell activating protein comprises a polypeptide having an amino acid sequence selected from the group consisting of:

RIGRIVTAKY (SEQ ID NO. 4);
ASRLDLRIGCIVrAK (SEQ ID NO. 5);
ASRLDLRIGRIVTAKY (SEQ ID NO. 6);
ASRLDLRIGRIVTAK (SEQ ID NO. 7);
LRIGRIVTAKY (SEQ ID NO. 8);
RIGRIVT (SEQ ID NO. 9);
RIGRIIT; and
AIGRIVT (SEQ ID NO. 10).

In an embodiment, the effector cell activating protein is conjugated to an immobilizer. The immobilizer preferably comprises a polypeptide having a molecular weight of at least about 5,000 daltons. In a specific embodiment, the immobilizer is albumin.

This invention provides an antibody capable of binding to the effector cell activating protein. In a specific embodiment, the antibody is a polyclonal antibody. In another embodiment the antibody is a monoclonal antibody.

This invention further provides a method of obtaining an antibody to effector cell activating protein comprising a) immunizing a rabbit with the effector cell activating protein coupled to keyhole limpet hemocyanin; and b) obtaining purified IgG from the rabbit. In a specific embodiment the antibody is a polyclonal antibody. In another embodiment, the antibody is a monoclonal antibody.

This invention provides a method of detecting the effector cell activating protein.

This invention provides a method of detecting the presence in a sample of effector cell activating protein comprising a) adding cells to a first chamber; b) adding the sample to a second chamber which is separated from the first chamber by a membrane; c) visualizing migrating cells; d) counting the migrating cells; and e) determining the presence of the effector cell activating protein. In a further embodiment, the cells are mononuclear phagocytes. In another embodiment, the cells are polymorphonuclear leukocytes.

This invention also provides a method of detecting the presence in a sample of effector cell activating protein comprising the steps of a) injecting the sample into an animal footpad; and b) detecting an inflammatory response, indicating the presence in the sample of effector cell activating protein. In a specific embodiment of this method, the animal footpad is a mouse footpad.

A specific embodiment of the method of detecting the effector cell activating protein comprises a step of detecting binding to mononuclear phagocytes.

This invention provides a method of detecting the effector cell activating protein comprising a step of detecting increased $[Ca^{2+}]_i$ in effector cells. In a specific embodiment the effector cells are selected from the group consisting of mononuclear phagocytes and polymorphonuclear leukocytes.

This invention also provides DNA encoding the effector cell activating protein. This DNA may comprise the coding strand or the strand complementary to the coding strand. It may be single-stranded or double-stranded, circular or linear. It may further comprise promoters and other expression control sequences known to one with skill in the art to which this invention pertains. Because of the degeneracy of the genetic code, which is well known to one with skill in the art to which this invention pertains, various DNA sequences code for a single amino acid sequence.

In a specific embodiment, this invention provides DNA encoding the effector cell activating protein which comprises an amino acid sequence selected from the group consisting of:

RIGRIVTAKY;
ASRLDLRIGCIVTAK;
ASRLDLRIGRIVTAKY;
ASRLDLRIGRIVTAK;
LRIGRIVTAKY;
RIGRIVT;
RIGRIIT; and
AIGRIVW.

This invention provides a method of using the effector cell activating protein to induce cell chemotaxis. In a specific embodiment the cells are mononuclear phagocytes. In another specific embodiment the cells are polymorphonuclear leukocytes.

This invention provides a method of inducing chemotaxis comprising a) adding cells to a first chamber; and b) adding a chemotaxis-inducing effective amount of the effector cell activating protein of claim 27 to a second chamber which is separated from the first chamber by a membrane, thereby inducing chemotaxis of the cells. In a specific embodiment the cells are mononuclear phagocytes. In another specific embodiment the cells are polymorphonuclear leukocytes.

This invention further provides a method of inducing inflammation in a subject comprising administering an inflammation-inducing effective amount of the effector cell activating protein.

This invention also provides a method of increasing $[Ca^{2+}]_i$ in effector cells using the effector cell activating protein. In a specific embodiment the effector cells are selected from the group consisting of mononuclear phagocytes and polymorphonuclear leukocytes.

This invention further provides a method of treating a tumor in a subject comprising administering an effective dose of endothelial monocyte activating polypeptide II (EMAP II).

In a specific embodiment, this invention provides a method for treating the tumor by inducing hemorrhage in the tumor.

In another embodiment, this invention provides a method for treating the tumor by reducing the volume of the tumor. In a preferred embodiment, the volume of the tumor is reduced by at least twenty-five percent (25%).

In a specific embodiment, this invention provides a method of treating a methylcholanthrene A-induced fibrosarcoma tumor in a subject comprising administering an effective dose of endothelial monocyte activating polypeptide II (EMAP II). In a specific embodiment the subject is a mammal. In a more specific embodiment the subject is a mouse. In another specific embodiment, the subject is a human.

In a specific embodiment this invention provides a method of treating a tumor in a subject comprising administering an effective dose of endothelial monocyte activating polypeptide II (EMAP II) wherein the effective dose is between about two micrograms and about fifty micrograms. In a more specific embodiment the effective dose is about twenty micrograms. In another specific embodiment the effective dose is between about six micrograms and about one hundred fifty micrograms. In a more specific embodiment the effective dose is about sixty micrograms.

An embodiment of the method for treating a tumor in a subject further provides that the endothelial monocyte activating polypeptide II (EMAP II) is in a pharmaceutically acceptable carrier.

In an embodiment the administering comprises injecting intratumorally. In another embodiment, the administering further comprises administering systemically.

In a specific embodiment, the tumor comprises carcinoma cells. In a more specific embodiment the carcinoma cells are mouse mammary carcinoma cells.

Another embodiment further comprises administering an effective dose of tumor necrosis factor. Preferably, the effective dose of tumor necrosis factor is administered systemically. In a specific embodiment the effective dose is between about 500 nanograms and about fifteen micrograms. Preferably, the effective dose is about five micrograms.

In an embodiment this invention provides a method for treating a tumor in a subject wherein the tumor comprises carcinoma cells. In a specific embodiment the carcinoma cells are mouse mammary carcinoma cells.

This invention further provides the method for treating a tumor in a subject wherein the EMAP II is recombinant EMAP II.

This invention further provides the method for treating a tumor in a subject wherein the endothelial monocyte activating polypeptide II (EMAP II) comprises:

SKPIDASRLDLRIGCIVTAKKHPDADSLYVEEVDV-
GEAAPRTVVSGLVNHVPLEQMQNRMVVLLCN-
LKPAKMRGVLSQAMVMCASSPEKVEILAPPNG-
SVPGDRITFDAFPGEPDKELNPKKKIWE-
QIQPDLHTNAECVATYKGAPFEVKGKGVCRAQ-
TMANSGIK (SEQ ID NO. 11).

This invention further provides a pharmaceutical composition comprising an effective amount of endothelial monocyte activating polypeptide (EMAP II) in a pharmaceutically acceptable carrier. One of ordinary skill in the art will readily known how to select a pharmaceutically acceptable carrier for administration of EMAP II.

This invention will be better understood from the Experimental Details which follow. However, one skilled in the art will readily appreciate that the specific methods and results discussed are merely illustrative of the invention as described more fully in the claims which follow thereafter.

Experimental Details

First Series of Experiments

A. Endothelial Monocyte Activiting Polypeptide II Materials and Methods

Culturing of cells and preparation of meth A-conditioned medium, Meth A cells, provided by Drs. Hoffman and Old (Memorial Sloan-Kettering Cancer Center) (11), were grown in RPMI 1640 containing 10% calf serum (Hyclone Labs, Logan, Utah) using a continuously perfused three liter bioreactor (Bellco Biotechnology, Vineland, N.J.). The bioreactor was washed with ten liters of serum-free medium (to remove serum components from complete medium), and then serum-free conditioned medium was collected at a rate of 416 ml/h, and concentrated 20-fold by ultrafiltration (12). Human umbilical vein endothelial cells (ECs) were prepared by the method of Jaffe (13), as modified by Thornton et al (14). Experiments were performed within 48 hours of the cells achieving confluence.

Purification of 22 kDa meth A factor. Following concentration of the conditioned medium from meth A cells by ultrafiltration, it was acidified to pH 5.5 with MES (1 M) diluted 1:1 with 50 mM MES (pH 5.5), and applied to the cation exchange resin S-Sepharose Fast Flow (Pharmacia, Piscataway, N.J.; 5 ml resin/liter). TIhe resin was washed extensively in buffer containing MES (50 mM; pH 5.5), NaCl (50 mM), octyl-β-glucoside (0.1%) and PMSF (0.2 mM), and step-eluted with the same buffer supplemented with 1 M NaCl. Fractions with $OD_{280}$) 0.05 were pooled and dialyzed extensively versus phosphate buffer (50 mM); pH 5.5), NaCl (50 mM) and octyl-β-glucoside (0.1%). These procedures were performed at 4° C. The eluate from S-Sepharose was then applied to an FPLC Mono S column (HR 5/5; Pharmacia) equilibrated in the same buffer, and the column was eluted with an ascending salt gradient. Fractions were incubated with cultured ECs, and assayed for their ability to induce tissue factor (see below). Active fractions eluting at 250 to 300 mM NaCl were pooled, dialyzed in the presence of SDS (0.1%), and concentrated by ultrafiltration (10 kDa-filter, Centricon, Amicon, Lexington, Mass.). Samples were then 1:1 diluted in nonreducing Laemmli sample buffer (15), incubated at 37° C. for 1 hr and preparative SDS-PAGE (12%) was performed. Following electrophoresis, protein was visualized by staining with Coomassie Blue or proteins were eluted by incubating gel slices for 48 hrs at 4° C. with buffer containing sodium acetate (0.1 M; pH 8.3), octyl-β-glucoside (0.02%), azide (0.02%). Eluted proteins were incubated with ECs to test their ability to induce tissue factor (see below). In other cases, proteins in gels were visualized by silver staining using a kit (Biorad, Richmond, Calif.).

For sequence analysis, purified ≈22 kDa meth A factor was subjected SDS-PAGE 9.12%), transferred to polyvinylidene difluoride membranes (16), and the broad band corresponding to Mr ≈22,000 was sequenced (Applied Biosystems, Inc. model 470A, Foster City, Calif.). The sequence was entered into the program WordSearch for the sequence analysis software package y Genetics Computer Group (17) to search the National Biomedical Research Foundation protein database. Other lanes from the same gel used for sequence analysis were transferred to nitrocellulose, proteins were eluted by the method of Anderson (18) and their ability to induce tissue factor in ECs was studied (see below).

Purified ≈22 kDa meth A factor was tested in the D10 bioassay for Interleukin 1 activity using the D10(N4)M cell line (19) (limit of detection 2 U/ml; generously performed by J. Plocinski and Dr. W. Benjamin, Hoffmann-LaRoche, Nutley, N.J.) and in the L929 assay for tumor necrosis factor activity (20) (limit of detection, 0.8 ng/ml; generously performed by J. DiPirro and Dr. J. Brentjans, SUNY, Buffalo, N.Y.). Neutralizing antibody to murine Interleukin 1α was obtained from Dr. R. Chizzonete (Hoffmann-LaRoche) and antibody to urine tumor necrosis factor was purchased from Genzyme (Cambridge, Mass.). Murine EMAP I and VPF/VEGF were prepared as described previously (9,22). Murine IL-1α was generously provided by Dr. P. Lomedico (Hoffmann-LaRoche) and murine TNFα was obtained from Genzyme (Cambridge, Mass.).

Production and screening of polyclonal antibodies. Because only limited amounts of the ≈22 kDa polypeptide were available, a peptide based on the amino acid sequence was employed as immunogen. The peptide comprised the N-terminal sequence with Cysteine substituted for the undetermined amino acid at position 15 (see Table 1)(Multiple Peptide Systems, San Diego, Calif.) and an additional cysteine at the carboxy terminus to facilitate coupling to keyhole limpet hemocyanin using M-maleimidobenzoyl-N-hydroxysuccinimide (21). Rabbits were immunized by standard methods (initial immunization: 1 mg/animal; monthly boosts: 500 μg/animal; intradermal). Rabbit IgG, purified by affinity chromatography on protein A-Sepharose (Pharmacia)(22), was screened by ELISA (Enzyme-Linked Immunosorbent Assay) using purified ≈22 kDa polypeptide. The ELISA was performed as follows: partially purified ≈22 kDa polypeptide or purified ≈22 kDa polypeptide in coating buffer ($Na_2CO_3$, 15 mM; $NaHCO_3$, 35 mM, $CaCl_2$, 0.1 mM; final pH 9.2) were incubated overnight at 4° C. in Nunc-Immuno Plate Maxisorp (Nunc-Kamstrup, Denmark). After 4 rinses in washing buffer (Tris/HCl, 20 mM; NaCl, 120 mM; Tween 20, 0.05%; final pH 7.4), the primary antibody (3 μg/ml) was added for 1 hour at 37° C., wells were washed 4 times with washing buffer, and then incubated with peroxidase conjugated goat anti-rabbit IgG (Sigma, St. Louis, Mo.) at a 1:1000 dilution for an additional 1 hour at 37° C. Wells were washed 4 times, substrate solution (O-phenylenediamine dihydrochloride, 0.05 ml, 0.4 mg/ml, Sigma) dissolved in 0.1 M sodium citrate (pH 4.5) containing H2O2 (0.0006%) was added, and color was allowed to develop. The reaction was stopped by adding $H_2SO_4$ (0.025 ml; 8N), and adsorbence at 490 nm was measured.

Western blotting and immunoprecipitation of ≈22 kDa meth A factor. Western blotting was performed using purified ≈22 kDa meth A-derived polypeptide, as well as other samples, by subjecting them to SDS-PAGE (12%) and electroblotting onto nitrocellulose papar (23). Reactive sites on the nitrocellulose were blocked overnight at room temperature with 3% nonfat dry milk in tris-buffered saline containing Tween 20(0.05%) (24). After 5 washes with the same buffer, nitrocellulose membranes were incubated for 2 hrs with polyclonal rabbit antibodies raised to the ≈22 kDa meth A factor (3 μg of immune IgG). Sites of primary antibody binding were detected with a secondary antibody conjugated to horseradish peroxidase using a kit from Amersham (Arlington Hts., Ill.). The approximate Mr of the meth A-derived polypeptide was estimated from the migration of standard proteins run simultaneously: phosphorylase b, 97.4 kDa, bovine serum albumin, 69 kDa, ovalbumin 46 kDa, carbonic anhydrase, 30 kDa, trypsin inhibitor, 21.5 kDa, and lysozyme, 14.3 kDa (Amersham).

Immunoprecipitation was performed by labelling cells metabolically with $^{35}$S-methionine as previously described (27). In brief, meth A cultures were incubated for 72 hrs in methionine-poor serum-free medium supplemented with $^{35}$S-methionine (10 μCi/ml), supernatants were harvested, diluted 1:1 with 50 mM MES (pH 5.5), applied to FPLC Mono S (HR 5/5; Pharmacia), and the column was then eluted with an ascending salt gradient (0 to 1 M NaCl). The Mono S fractions which co-eluted with ≈22 kDa meth A factor, based on the studies described above (0.25–0.3 M NaCl), were pooled, incubated overnight at 4° C. with immune or nonimmune IgG (5 μg/ml), and immune complexes were precipitated by the addition of formalin-fixed, protein A-bearing Staphylococcus aureus (IgGSorb, Enzyme Center, Malden, Mass.) for 2 hrs at room temperature. The immune precipitate was washed four times with tris-buffered saline (tris/HCl, 20 mM; pH 7.4; NaCl, 120 mM) containing NP-40 (0.25%), non-reducing Laemmli buffer was added, and the sample was boiled prior to SDS-PAGE.

Assays of endothelial cell and monocyte tissue factor. Tissue factor activity in human ECs was assayed by incubating confluent cultures (9.6 $cm^2$ growth area; ≈$1.2 \times 10^5$ cells/$cm^2$) with purified ≈22 kDa polypeptide in Medium 199 containing HEPES (10 mM; pH 7.4), polymyxin B (50 units/ml) and fetal calf serum (5%) in the presence/absence of other agents, such as either cycloheximide (10 μg/ml), actinomycin D (5 μg/ml), antibodies to the ≈22 kDa factor, or VPF/VEGF. Where indicated, ≈22 kDa meth A factor was treated with trypsin (5 μg/ml for 2 hr at 37° C.; trypsin was inactivated by addition of aprotonin, 25 μg/ml, Sigma) or heated (100° C. for 10 min; this destroys ≈22 kDa meth A factor activity, but has no effect on endotoxin-mediated induction of tissue factor activity) prior to addition to endothelial cell cultures. Monolayers were then incubated for the indicated times at 37° C., cells were scraped into suspension with a rubber policeman, and tissue factor activity was determined using a coagulant assay, as described previously (9,22). A blocking, monospecific antibody to tissue factor (2.5 μg/ml; generously provided by Dr. W. Kisiel, Univ. of New Mexico, Albuquerque, N. Mex.) was added to certain cell preparations just prior to performing the coagulant assay. Tissue factor equivalents were determined using a standard curve from experiments with purified human tissue factor (26). Tissue factor reconstituted into phosphati-dylserine/phosphatidylcholine vesicles (20:80) was generously provided by Dr. Ronald Bach, Univ. of Minnesota, Minneapolis, Minn.).

Procoagulant activity of mouse macrophages was determined as follows: suspensions of macrophages ($10^4$ cells/assay), isolated from the peritoneum 3–4 days after stimulation with thioglycollate broth (2 ml; Sigma), were incubated with ≈22 kDa meth A factor alone or in the presence of other agents for the indicated times at 37° C. in RPMI 1640 containing HEPES (10 mM, pH 7.4), penicillin, streptomycin (50 U/ml; 50 μ/ml), β-mercaptoethanol ($5 \times 10^{-5}$ M), and polymyxin B (50 units/ml). Tissue factor was determined as described above using the coagulant assay with murine plasma. Data are expressed as clotting time in seconds per sample assayed, since purified murine tissue factor is not available to use as a standard.

The level of tissue factor mRNA transcripts in human ECs and mononuclears exposed to ≈22 kDa meth A factor was studied using the polymerase chain reaction (PCR). For this purpose, total RNA was extracted from stimulated or quiescent cells using the guanidinium thiocyanate procedure (27). First strand cDNA was synthesized with oligo dT primer (BRL, Bethesda, Md.) and served as template for PCR analysis. Tissue factor primers were generously provided by Dr. W. Konigsberg (Yale University, New Haven, Conn.) (28) and GAPDH primers (29) were 5' CCA CCC ATG GCA AAT TCC ATG GCA 3'(SEQ ID NO. 33) (sense) and 5' TCT AGA CGG CAG GTC AGG TCC ACC 3'(SEQ ID NO. 34) (antisense)(synthesized in the Cancer Center Core Laboratory, Columbia Univ.). For positive controls, 10 pg of plasmid carrying tissue factor (provided by Dr. Konigsberg) sequence were used. cDNA was amplified by PCR for 20 to 40 cycles, each cycle consisting of incubations at 94° C. for 1.25 min, 50° C. for 1.25 min, and 72° C. for 2.25 min. Products were analyzed by agarose gel electrophoresis (2%) and were visualized with ethidium bromide under UV.

Assessment of mononuclear phagocyte (mononuclears) and polymorphonuclear leukocyte (PMN) migration. Human peripheral blood monocytes were isolated from the blood of normal healthy volunteers (30). Blood was centrifuged on Hisopaque 1077 (Sigma, St. Louis, Mo.), the mononuclear fraction was obtained, washed twice in Earle's balanced salt solution, resuspended in RPMI 1640 containing human serum (10%; Gemini, Calabasas, Calif.), plated on tissue culture dishes and incubated at 37° C. for 1–2 hrs. Nonadherent cells were removed by washing the plate twice with balanced salt solution, and adherent cells were harvested by incubation with calcium-magnesium free buffer containing EDTA (2 mM) for 15 min at 37° C., followed by extensive washing. PMNs were prepared by centrifugation over Hisopaque 1119 as per the manufacturer's protocol (Sigma). Chemotaxis assays were performed in microchemotaxis chamber (NeuroProbe, Bethesda, Md.) containing Nucleopore polycarbonate membranes (5 µm; Nucleopore, Pleasonton, Calif.). Mononuclears or PMNs were suspended in RPMI 1640 containing fetal bovine serum (1%) and $10^4$ cells were added per well to the upper chamber. The chemotactic stimulus was added to the indicated chamber, and assays were performed in quadruplicate over a 3 hr or 45 min incubation period at 37° C., with mononuclear cells or PMNs, respectively, after which non-migrating cells were removed, membranes were fixed in methanol, migrating cells were visualized with Wright's stain. Cells in nine high-power fields were counted, and the mean and standard error of the mean (SEM) were determined.

Mouse footpad studies. The potential in vivo effects of the ≈22 kDa meth A factor were assessed in the mouse foot pad model (31). In brief, footpads of female Balb/c mice (6–12 wks) were injected with ≈0.03 ml of either (i) Tris-buffered saline, ≈22 kDa meth A polypeptide (homogeneous, gel-eluted material), (ii) gel-eluted material from a region of the same SDS gel which had no ≈22 kDa meth A factor, (iii) V6,13 22 kDa meth A factor which had been pre-treated with trypsin (enzyme:substrate ratio, 1:50, w:w) for 1 hr at 37° C. followed by addition of aproptonin (0.5 g), or (iv) ≈22 kDa meth A factor was heat-treated at 100° C. for 10 min to destroy tryptic activity. At the indicated times footpad thickness was measured with calipers (each footpad was measured five times at each time point), and, subsequently, animals were sacrificed. Footpads were fixed in buffered formalin (10%), decalcified, and embedded in paraffin. Sections were stained with hematoxylin and eosin.

Results

Purification of ≈22 kDa meth A factor (endothelial-monocyte activating polypeptide II [EMAP II]). In a previous study, two activities in conditioned medium from meth A fibrosarcomas which altered EC and mononuclear phagocyte properties were identified (9,10,22). The current report defines a third, novel meth A-derived polypeptide, distinct from those previously studied, which modulates endothelial and white cell functions.

Meth A-conditioned medium acidified, adsorbed to S-Sepharose, and the bound material was step-eluted (1 M, NaCl), dialyzed and applied to FPLC Mono S. The column was resolved with an ascending salt gradient, leading to the definition of three major peaks of activity, assessed by the induction of tissue factor activity in cultured ECs. The pool of fractions in activity peak I provided starting material for purification of EMAP I, a polypeptide with Mr ≈40,000, which was previously identified in tumor-conditioned medium (9,10). The material in activity peak III was used for preparation of murine Vascular Permeability Factor/ Vascular Endothelial Growth Factor (VEGF/VPF), and its activity could be neutralized by polyclonal antibody to guinea pig VPF, as described previously (22).

Activity peak II from the Mono S column was further analyzed by nonreducing SDS-PAGE, and elution of protein from nitrocellulose membranes after Western blotting. Although the pattern of protein bands visualized by Coomassie blue staining of the gels was complex, as expected form the chromatogram of the mono S column, there were only two areas on the gel, corresponding to Mr ≈'40,000 and ≈22,000, which on elution had the capacity to induce tissue factor activity in ECs. Since the higher molecular weight material was likely to correspond to EMAP I or VPF/VEGF, our attention was focussed on the factor(s) responsible for the activity at Mr ≈22,000.

To further characterized the material migrating with Mr ≈22,000 which was responsible for induction of EC tissue factor, the corresponding portion of the nitrocellulose membrane was eluted, and subjected to SDS-PAGE. One broad band with Mr ≈22,000 was visualized by silver staining of nonreduced and reduced SDS-PAGE. Gel elution studies demonstrated that the material in the slices co-migrating with this band on non-reduced SDS-PAGE induced tissue factor activity in ECs. Following reduction or exposure to trypsin, this material lost its activity (data not shown).

Characterization of the ≈22 kDa polypeptide. The ≈22 kDa polypeptide was characterized structurally, by N-terminal sequencing, and immunologically, using an antiserum prepared to a peptide comprising the N-terminal sequence, in order to assess its relationship to other mediators present in the tumor-conditioned medium.

The broad band of SDS-PAGE with Mr ≈22 kDa was transferred to PVDF and submitted for sequencing. Certain preparations ran as two closely spaced bands on SDS-PAGE, and both of these bands were transferred to PVDF and sequenced separately. In each case, identical preparations were transferred to nitrocellulose membranes, eluted, and demonstrated to induce tissue factor in ECs. The same N-terminal sequence was obtained each time (Table 1), and all samples displayed comparable capacity in the induction of EC tissue factor. Comparison of this sequence with others available in the database indicated that it was unique, with greatest homology to human von Willebrand antigen II (the propolypeptide region of von Willebrand Factor)(32–33) (Table 1).

TABLE 1

Comparison of amino terminal sequence of ≈22 kDa meth A factor (EMAP II) with human von Willebrand Factor (vWF) antigen II.

```
EMAP II:             Gly-Lys-Pro-Ile-Asp-Ala-Ser-
Arg-Leu-Asp-Leu-Arg-Ile-Gly-Xaa-Ile-Val-Thr-Ala-Lys
    |   |   |   |   |               |   |   |
    |   |   |   |   |               |   |   |
    |   |   |   |   |               |   |   |
vWFII -Asp-Leu-Arg-Ile-Gln-Arg-Thr-Val-Thr-Ala-Ser-(SEQ. ID NO. 15)
```

The portion of the vWF antigen II sequence shown corresponds to Asp (480) to Ser (490), and was deduced from the cDNA (32–33).

Antibodies to the ≈22 kDa polypeptide were prepared by immunizing rabbits with a synthetic peptide comprising the amino terminal sequence coupled to keyhole limpet hemocyanin. IgG from this antiserum neutralized the ability of the ≈22 kDa meth A factor to induce tissue factor activity in ECs in a dose-dependent manner and adsorbed the activity when the antibody was bound to a solid support. In contrast, non-immune IgG was without effect.

Immunoblotting with IgG prepared to the synthetic peptide, following non-reduced SDS-PAGE, visualized a major band with Mr 22,000 in samples of purified ≈22 kDa meth A factor and fractions from activity peak II from FPLC Mono S. Shorter exposure times of blots to the film showed that this major band was composed of two closely migrating bands. Addition of excess purified ≈22 kDa meth A factor during incubation of blots with the anti-peptide antibody greatly diminished intensity of the band, indicating that the antibody was recognizing determinants on EMAP II. Consistent with the specificity of the antibody for ≈22 kDa meth A factor, no bands were seen in blotting studies with EMAP I, VPF/VEGF, murine IL-1α or murine TNF. The distinction between ≈22 kDa meth A factor and the cytokines TNF and IL-1, both of which induce tissue factor in endothelium (34–37), was further supported by the finding that purified EMAP II had no IL-1 or TNF activity in sensitive bioassays (the D10 and L929 assays, respectively) (19–20), and that antibodies to these cytokines did not alter EMAP II activity.

To be certain that ≈22 kDa meth A factor was synthesized by the tumor cells, cultures were metabolically labelled with $^{35}$S-methionine, the supernatant was concentrated by cation exchange chromatography, and the eluate subjected to immunoprecipitation. Antipeptide IgG precipitated a band with Mr ≈22,000 from meth A tumor cells observed on both reduced and nonreduced SDS-PAGE. The appearance of this band was greatly diminished when excess ≈22 kDa meth A factor was added during incubation of reaction mixtures with the primary antibody, and no band was seen when immune IgG was replaced with non-immune IgG.

The IgG fraction of antiserum to the amino terminal peptide derived from the ≈22 kDa meth A factor was employed to construct an ELISA. This ELISA was used to monitor the purification procedure of the ≈22 kDa polypeptide (Table 2): about 195-fold purification was required to obtain homogeneous ≈22 kDa meth A factor with the series of steps used.

TABLE 2

Monitoring the purification procedure of ≈22 kDa meth A factor (EMAP II) by ELISA*.

| Total protein [mg] | EMAP II antigen [mg] | Sp.activity EMAP II antigen | Purification fold | Yield EMAPII antigen |
|---|---|---|---|---|
| Tumor supernatant | | | | |
| 150 Fast S. batch | 0.77 | .00513 | 1 | 100% |
| 170 Mono S | 0.38 | .0223 | 4.4 | 50% |
| 0.4 Gel elution | 0.14 | .35 | 68.2 | 36% |
| 0.01 | 0.0095 | 1 | 195 | 6.8% |

*EMAP II antigen was measured using an ELISA, as described in the text. The starting volume of culture supernatant for this preparation was about 40 liters.

Functional characterization of ≈22 kDa meth A factor. To understand the potential contribution of the ≈22 kDa polypeptide to vascular dysfunction in the tumor bed and the inflammatory infiltrate which characteristically surrounds meth A tumors (3–6, 38–39), experiments were performed to assess its effects on ECs, mononuclear phagocytes, and polymorphonuclear leukocytes (PMNs).

Incubation of cultured human ECs with purified ≈22 kDa meth A factor led to a time-dependent, reversible increase in procoagulant activity which was maximal by 10–12 hrs, and then declined. Procoagulant induction was also dependent on the dose of ≈22 kDa polypeptide, being half-maximal by about 20–30 pM. Studies with a blocking monospecific antibody to tissue factor identified the induced EC procoagulant activity as tissue factor. Tissue factor expression required de novo biosynthesis, as demonstrated by inhibition in the presence of actinomycin D and cycloheximide. Consistent with the involvement of biosynthetic mechanisms, the level of transcripts for tissue factor mRNA increased on exposure to ≈22 kDa meth A factor, as indicated by the greater intensity of the PCR reaction product. In contrast, the level of transcripts for glycerceraldehyde phosphate dehydrogenase (GAPDH) mRNA in ECs was unchanged under these conditions. EMAP II-mediated induction of EC tissue factor was not likely to be due to contaminating endotoxin, as demonstrated by the inhibitory effect of antibody raised to the amino terminal EMAP II peptide and pre-treatment of the polypeptide with trypsin. In addition, all assays of endothelial procoagulant activity were performed in the presence of polymyxin B.

Mononuclear cells associated with tumors are often enmeshed in fibrin, suggesting that they might express procoagulant activity (38). Therefore, experiments were performed to examine if ≈22 kDa meth A factor could induce monocyte procoagulant activity. Incubation of murine peritoneal macrophages with EMAP II resulted in induction of procoagulant activity, as shown by the ability of the treated cells to shorten the clotting time of recalcified murine plasma. Induction of procoagulant activity occurred in a time-dependent manner, peaking at about 6–12 hours, and could be blocked almost completely by a monospecific antibody against human tissue factor, indicating that most of the clot promoting activity was due to tissue factor. Tissue factor expression by mononuclears in response to ≈22 kDa meth A factor was also dependent on the polypeptide's concentration, could be blocked by treating EMAP II with trypsin, and required the integrity of biosynthetic mechanisms, as it was prevented by addition of actinomycin D to cultures. Similar to the results on ECs described above, enhanced expression of mononuclear cell tissue factor activity was accompanied by an increase in the level of tissue factor mRNA transcripts, as evidenced by PCR.

Immunogenic tumors, such as the meth A fibrosarcoma, are often surrounded by an inflammatory infiltrate (38, 40–41). Experiments were performed to examine if the ≈22 kDa meth A polypeptide could induce migration of human PMNs and mononuclear cells harvested from peripheral blood (Tables 3–4). Experiments in microchemotaxis chambers demonstrated that EMAP II enhanced cell migration in a dose-dependent manner for PMNs (Table 3) and for mononuclear cells (Table 4). Cell migration in response to EMAP II was prevented by exposing the polypeptide to trypsin or by adorption of EMAP II with polyclonal antibody to the N-terminal peptide. Checkerboard analysis in which the ≈22 kDa meth A factor was added to both the upper and lower compartments of the chambers indicated that enhanced migration was due to chemotaxis, not simply chemokinesis (Tables 3–4).

Figure 1:
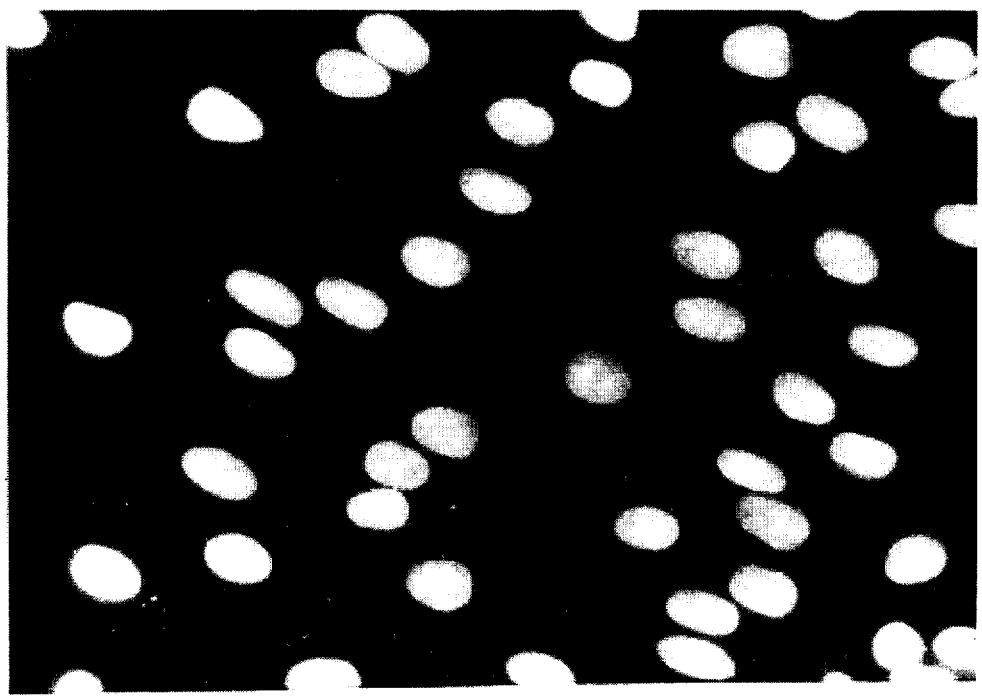

The effect of EMAP II on migration and division of bovine aortic endothelial cells in an in vitro wound model was also studied. Confluent monolayers of BAE were stimulated to migrate and divide by removal of a ring fence creating a 5 mm diameter wound, at the time of wounding monolayers were exposed to EMAPII or control medium for 24 hours. Following incubation monolayers were washed, fixed in 3.5% paraformaldehyde in phosphate buffered saline containing 0.1% Nonidet P-40 and nuclei were stained with Hoechst 33258. Control monolayers migrating into the wound margin display normal interphase nuclei compared with those exposed to EMAP, in which there are many condensed, pyknotic (apoptotic) nuclei (FIG. 1).

TABLE 3

Induction of polymorphonuclear leukocyte migration by ≈33 kDa meth A factor (EMAP II): checkerboard analysis*.

| Lower compartment | Upper compartment | | | |
|---|---|---|---|---|
| | 0 | 40 pM | 100 pM | 200 pM |
| 40 pM | 66 (S.D.7.8) | 50.5 (S.D.23.5) | 59 (S.D.19.8) | 52 (S.D.25.3) |
| 100 pM | 79 (S.D.22.9) | 63.6 (S.D.13) | 54 (S.D.17.4) | 58 (S.D.17.6) |
| 200 pM | 107 (S.D.29.8) | 95.7 (S.D.15.6) | 86.4 (S.D.23) | 57.8 (S.D.17.6) |

*Cell migration assays were performed by adding PMNs to the upper wells of microchemotaxis chambers, and placing the indicated concentration of ≈ kDa meth A factor in the upper and/or lower wells. The incubation period was 45 min at 37° C. Migrating cells from nine representative high-powered fields are shown (the mean and standard deviation, S.D.).

TABLE 4

Induction of mononuclear cell migration by ≈22 kDa meth A factor (EMAP II): checkerboard analysis*.

| Lower compartment | Upper compartment | | | |
|---|---|---|---|---|
| | 0 | 50 pM | 100 pM | 200 pM |
| 50 pM | 18 (S.D.2.6) | 20 (S.D.3.7) | 15.7 (S.D.2.3) | 14.3 (S.D.1.2) |
| 100 pM | 30.4 (S.D.5.8) | 24.4 (S.D.2.6) | 19 (S.D.1.8) | 17.2 (S.D.2.6) |
| 200 pM | 53.78 (S.D.3.1) | 31.2 (S.D.1.2) | 18.7 (S.D.2.4) | 13.7 (S.D.0.8) |

*Cell migration assays were performed by adding mononuclear cells to the upper wells of microchemotaxis chambers, and placing the indicated concentration of ≈22 kDa meth A factor in the upper and/or lower wells. The incubation period was 3 hr at 37° C. Migrating cells from nine representative high-powered fields are shown (mean and standard deviation, S.D.).

Figures 1, 2:
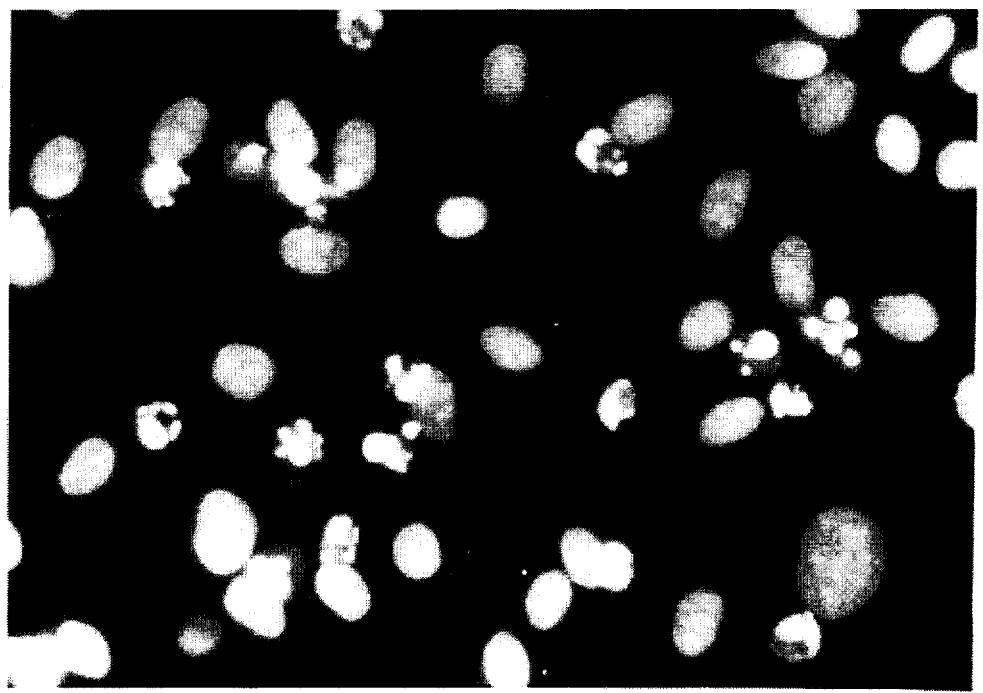
Figures 1, 2:
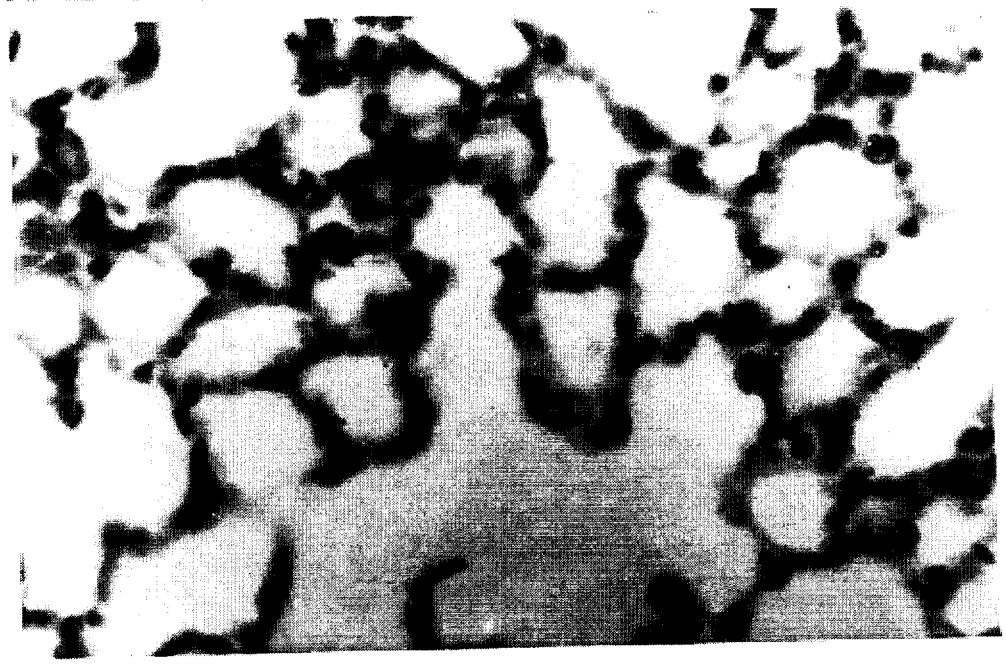
Figure 2:
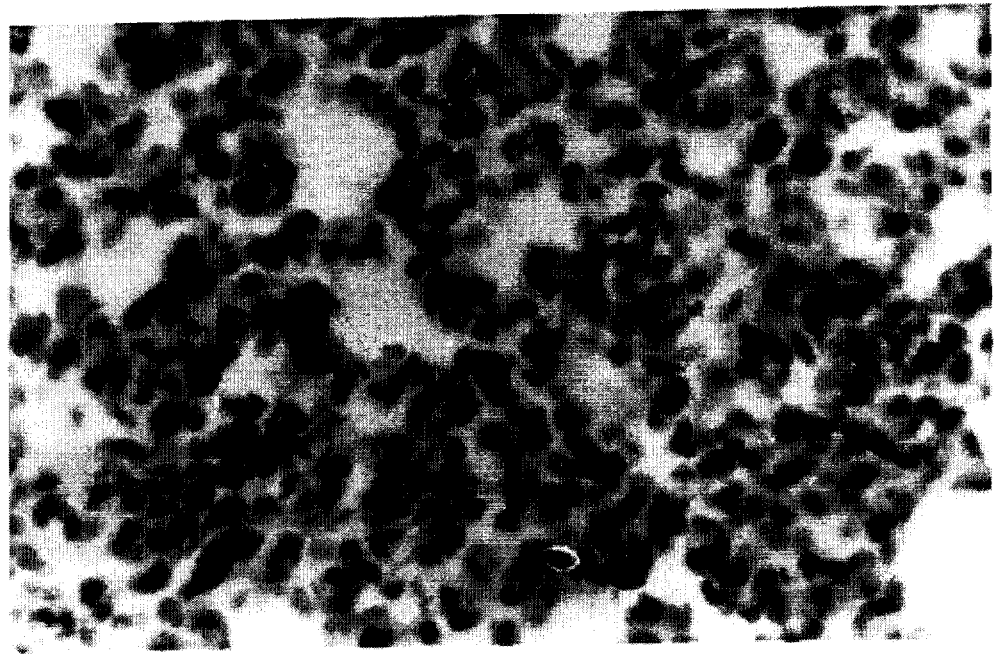
Figure 3A:
FIGS. 3(A–D): Light micrographs of footpads inoculated with either EMAP II-derived peptide-albumin conjugates or albumin alone. Mouse footpads were injected with either albumin alone (A), albumin exposed to glutaraldehyde (B), albumin-RIGRIVTAKY (C), or albumin-ASRLDLRIGRIVTAKY (D). Following 6 hrs, footpads were harvested, processed as described in the text, and stained with hematoxylin/eosin. Magnification: ×350.
Figure 3B:
Figure 3C:
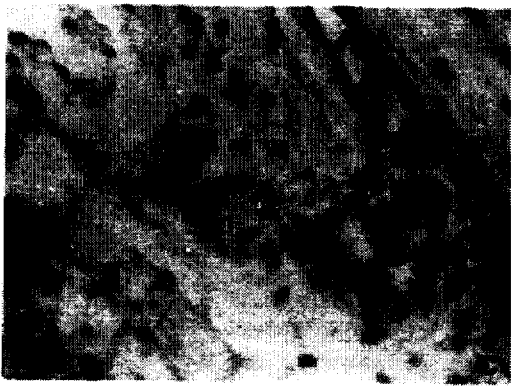
Figure 3D:
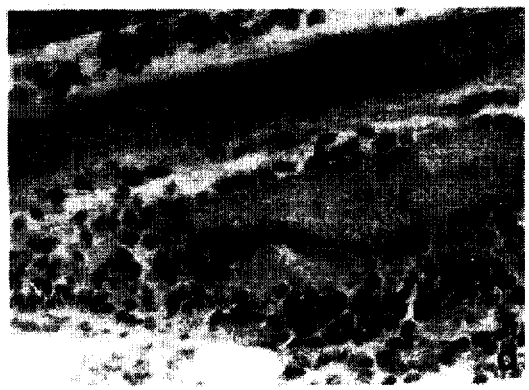

Phloaogenic properties of ≈22 kDa meth A-derived polypeptide (EMAP II) in the mouse footpad model. When EMAP II was injected into mouse footpads, swelling was observed as evidenced by the increase in footpad thickness compared with buffer controls. The footpad showed an acute inflammatory response characterized by a PMN infiltrate and edema in the subcutaneous tissues, compared with the untreated control. The inflammatory response had begun to recede by 8 hr after injection of EMAP II. In contrast to these results with intact EMAP II, trypsin-treatment of polypeptide abrogated its phlogogenic properties (FIG. 2).

Discussion

Immunogenic tumors, such as the murine meth A fibrosarcoma, characteristically have a peripheral zone which contains a chronic inflammatory infiltrate (38–41). The presence of these inflammatory cells, often embedded in a meshwork of fibrin which can extend throughout the tumor stroma, contributes to the concept that tumors might be considered "wounds that do not heal (38)." This has led us to identify tumor-derived mediators which could prime the host response, altering endothelial properties and attracting inflammatory cells to the tumor. Previously, we presented the initial characterization of two polypeptides which, based on in vitro studies, could activate ECs and monocytes: EMAP I, a trypsin-sensitive, ≈40 kDa polypeptide distinct from other cytokines and growth factors (9–10), and a polypeptide which turned out to be the murine homolog of VPF/VEGF (22), a factor which had previously been shown to increase vascular permeability and to be mitogenic for ECs (42–46). In this report, a third polypeptide has been identified in supernatants of meth A tumor cells (EMAP II). EMAP II activates ECs and mononuclear cells, potentiating their participation in procoagulant reactions through induction of tissue factor, promoting migration of monocytes and PMNS, and leading to a phlogogenic response when injected into murine footpads. EMAP II is an apparently unique polypeptide which runs as a broad band, Mr ≈22,000. In view of the apparently similar spectrum of biological properties of EMAP II and the other two mediators, VPF/VEGF and EMAP I, it was important to determine if there was a relationship between these molecules. Although the amino terminal sequence and chromatographic properties of EMAP II were distinct, it could represent an alternatively spliced or degraded form derived from the other polypeptides, which appear to be about twice as large, Mr 38–44 kDa versus ≈22 kDa. However, studies with polyclonal antibody directed against the amino terminal portion of EMAP II did not show any immunoreactivity with either EMAP I or VPF/VEGF. In addition, polyclonal antibodies which adsorb murine VPF/VEGF (22) did not react with EMAP II (data not shown). Furthermore, metabolic labelling and immunoprecipitation of meth A tumor cells demonstrated EMAP II to be synthesized as a ≈22 kDa polypeptide, no larger precursor form was evident. These findings are supported by functional studies which showed that EMAP II has distinct biologic activities compared with EMAP I and VPF/VEGF: EMAP II stimulates PMN migration, in contrast to the other two mediators, but EMAP II does not directly increase EC monolayer permeability in culture, whereas EMAP I and VPF/VEGF do. Finally, molecular cloning studies have shown EMAP II to be distinct from EMAP I, VPF/VEGF, and vWF antigen II. With respect to vWF antigen II, the region of sequence homology with EMAP II is limited to the portion of the amino terminus shown in Table 1. Taken together, these data suggest that EMAP II is a distinct molecule, capable of eliciting a phlogogenic response and, potentially, augmenting the effects of other tumor-derived cytokines.

An important and unexplained question concerning the production of inflammatory mediators by meth A, as well as other tumors, is why polypeptides such as EMAP I, VPF/VEGF, and EMAP II do not result in a more striking host response in the tumor bed. On the one hand, other components of the tumor milieu, such as binding proteins, proteases or cytokines with opposing actions, could modulate their effects. Alternatively, the amount of EMAP II or other mediators elaborated by tumors in vivo might be insufficient to induce an optimal host response. Future studies, employing neutralizing antibodies to these polypeptides and cell lines expressing variable amounts of these mediators, will be required to directly assess the effect of tumor-derived cytokines on the neoplasm.

B. Peptide Derived From the Amino Terminus of Endothelial-Monocyte Activating Polypeptide II Materials and Methods Purification of EMAP II, preparation and radiolabelling of synthetic peptides. Murine EMAP II (EMAP II), purified as described (7), was homogeneous on SDS-PAGE, migrating as single band, Mr ≈18 kDa. Elution of the latter band from SDS-PAGE demonstrated its capacity to induce EC and MP tissue factor activity, as well as to promote MP and PMN migration, as described previously (7). A series of peptides were prepared based on the N-terminal sequence of murine EMAP II (7) via solid phase methodology (22) using either t-boc or f-moc chemistry. Crude peptides were purified by HPLC and analyzed via mass spectrometry. The peptide RIGRIIT was generously provided by Drs. Arun Patel and George Glover (SmithKline Beecham, King of Prussia Pa.). As indicated, peptides were prepared with an additional C-terminal tyrosine to facilitate radioiodination by the chloramine T method (23). The final specific radioactivity of RIGRWTAKY was $3 \times 10^5$ cpm/ng.

Murine tumor necrosis factor-α(TNF) was purchased from Genzyme (Cambridge Mass.), murine IL-1α (TNF) was generously provided by Dr. Peter Lomedico (Hoffmann-LaRoche, Nutley N.J.), and formyl-methlonyl-leucinyl-phenylalanine (fMLP) was obtained from Sigma (St. Louis Mo.).

Preparation of PMNS, MPs, and ECs. Human PMNs were isolated from heparinized blood of normal volunteers by centrifugation over Histopaque 1119 (Sigma). Pellets containing erythrocytes and PMNs were diluted 1:2 in normal saline, exposed to NaCl (0.2%) for 20 sec (to lyse erythrocytes), restored to isotonicity, and centrifuged (350× g) for 10 min (7,24). The latter procedure was repeated twice, and the resulting cell population, >98% PMNs, was resuspended in RPMI 1640 containing heat-inactivated human serum (5%; Gemini, Calabasas Calif.) at a density of ≈$10^8$ cells/ml. Human peripheral blood monocytes were isolated by centrifugation on Histopaque 1077 (Sigma). The mononuclear fraction was obtained, washed twice in Hank's balanced salt solution, resuspended in RPMI 1640 containing human serum (10%), and subjected to an adherence step on tissue culture plasticware. The adherent cell population was harvested by incubation in calcium-magnesium-free buffer containing EDTA, as described previously (7,25), and MPs were resuspended in RPMI 1640 containing human serum (10%) at a density of $10^6$ cells/ml. Human umbilical vein ECs were prepared by the method of Jaffe (26) as mod-iied by Thornton et al (27, and were characterized as described previously (28). Experiments were carried out within 48 hrs of the cells achieving confluence.

Assays of MP, PMN, and EC properties. The effect of synthetic peptides on MP and PMN migration and cytosolic $[Ca^{2+}]_i$, MP and EC tissue factor, and PMN peroxidase release was studied as described below.

Cell migration was studied by adding MPs or PMNs ($10^4$ cells/well) resuspended in RPMI 1640 with fetal calf serum (1%; Gemini) to the upper wells of a microchemotaxis chamber (Neuro Probe, Bethesda, Md.) containing Nucleopore polycarbonate membranes (5 μm, Nucleopore, Pleasanton Calif.), as described (7,29–30). The chemotactic stimulus was placed in the upper or lower chamber, as indicated, and cells were allowed to migrate for 3 hrs (for MPs) or 45 min (for PMNs) at 37° C. Following removal of non-migrating cells, membranes were fixed in methanol and migrating cells were visualized with Wright's stain. Assays were performed in quadruplicate, and cells were counted in nine high-power fields in each case (mean±SEM is shown in the figures).

Tissue factor activity of monolayers of ECs and MPs was determined (7) after incubation with EMAP II-derived peptides at 37° C. for 4–12 hrs by washing cultures with HEPES (10 mM; pH 7.4), NaCl (137 mM), KCl (4 mM), $CaCl_2$ (3 mM), glucose (10 mM), bovine serum albumin (0.5 mg/ml), and addition of 0.5 ml of the same buffer along with purified human Factor VIIa (1 mM) and Factor X (200 nM) for 45 min at 37° C. Aliquots (0.05 ml) of the reaction mixture (one per well) were withdrawn at 15 min intervals, added to a buffer containing Tris (50 mM; pH 7.9), NaCl (175 mM), EDTA (5 mM) and bovine serum albumin (0.5 mg/ml; 0.05 ml), and the zuhromogenic substrate Spectrozyme Factor Xa (American Diagnositca, Inc., Greenwich Conn.; 0.01 ml; 2 mM). Cleavage of the substrate was monitored by the change in absorbance at 405 nm (BioKinetics Reader, Winooski, Vt.). Factor Xa concentration was determined by comparison with a standard curve generated with known amounts of purified human Factor Xa. Human, plasma-derived Factors VIIa and X were purified to homogeneity as described (31).

$[Ca^{2+}]_i$ measurements. PMNs or MPs ($2 \times 10^7$ cells in each case) were incubated with fura-2AM (1 μM) and pluronic detergent (0.02%) for 12 min at room temperature, diluted sixfold, and incubated for a further 30 min at room temperature to allow for complete hydrolysis of the dye. Cells were then resuspended in HEPES-buffered saline at $5 \times 10^5$ cells/ml (32). For experiments using MPs, sulfinpyrazone (0.5 mM) was included at all steps to minimize both dye sequestration into intracellular organelles and dye efflux (33). Fluorescence of fura-2 was monitored at 37° C. in a thermostatically-controlled cuvette installed in a Perkin Elmer Model 650-40 fluorescense spectrophotometer. Calibration of $[Ca^{2+}]_i$ was performed as described (34).

Release of peroxidase generatinc activity from PMNs (myeloperoxidase) was determined by oxidation of the peroxidase substrate 3,3',5,5'-tetramethylbenzidine (TMB; Sigma), monitored at 620 nm, as described (35). In brief, PMNs ($3 \times 10^6$ cells/ml; 0.05 ml) were incubated for 60 min at 37° C. with RPMI 1640 containing fetal calf serum (1%) alone or in the presence of phorbol ester (phorbol 12-myristate 13-acetate; Sigma) or EMAP II-derived peptides. TMP and hydrogen peroxide were added for 1 min at room temperature, and the reaction was stopped with sodium azide and acetic acid. Peroxidase activity, assessed by oxidation of TMB, was determined spectrophotometrically and is reported as percent total peroxidase activity (100% is the activity observed with that number of PMNs following 60 min exposure to phorbol ester, 10 μM). A standard curve was generated by assaying peroxidase activity from different numbers of PMNs treated with phorbol ester (10 μM) under these conditions, and peroxidase activity of PMN/EMAP II peptide incubation mixtures was determined by comparison with the linear portion of the standard curve (35).

Cell Binding and Cross Linking Studies

Radioligand binding studies were performed on human MPs plated in 96-well plates ($5-6 \times 10^4$ cell/well). Cells were washed twice with Hanks balanced salt solution, and then Dulbecco's Modified Eagle Medium containing HEPES (25 mM; pH 7.4), penicillin/streptomycin (50 U/ml; 50 μg/ml), and bovine serum albumin-fatty acid free (0.5%; Sigma) were added (0.1 ml/well). Cultures were incubated at 4° C. for 2 hrs with $^{125}$I-RIGRIVTAKY alone or in the presence of unlabelled peptide/protein. Each well was washed four times over a period of 20 sec, and cell-associated radioactivity was eluted by an acidic buffer (HCl, 0.1 M, pH 2; NaCl, 0.1 M) at 4° C. for 5 min. During the elution period, there was no detachment of cells from the growth substrate. The conditions for incubation and washing used in the binding studies shown in FIG. 3 (2 hrs at 4° C.) were insufficient to allow binding of $^{125}$I-RIGRIVTAKY to reach an apparent maximum, even at the lowest tracer concentrations, and to remove unbound material by washing quickly so that <10% of the cell-bound radioactivity dissociated. Binding data were analyzed according to the equation of Klotz and Hunston (36), B=nKA/(1+KA), where B=specifically bound ligand (specific binding=total binding, wells incubated with tracer alone, minus nonspecific binding, wells incubated with tracer in the presence of excess unlabelled material), n=sites/cell, K=the dissociation constant, and A=free ligand concentration using nonlinear least-squares analysis (Enzfitter, Cambridge UK).

Cross-linking experiments were performed on MPs plated in 24-well plates ($1.5$–$2.5 \times 10^5$ cells/well) and incubated with radiolabelled peptides as described above. At the end of the incubation period, disuccinimidyl suberate (0.2 mM; Pierce,. Rockford, Ill.)(37) was added for 15 min at room temperature. Cultures were then washed four times with Hanks balanced salt solution, solubilized with lysis buffer (Tris, 10 mM, pH 7.5; NP-40, 1%; EDTA, 1 mM; PMSF, 1 mM; pepstatin A, 1 µg/ml; aprotinin, 1.5 µg/ml) and centrifuged (13,000×g for 10 min) to remove cellular debris. Proteins that remained in the supernatants were precipitated by trichloroacetic acid (20%, final concentration). The pellet was washed twice with ice-cold acetone, dried (Speedvac, Savant, Farmingdale, N.Y.), solubilized and prepared for non-reduced SDS-PAGE (4–15%, Bio-Rad, Hercules Calif.) (38). After electrophoresis, gels were dried and subjected to autoradiography. The approximate Mr of the band corresponding to putative complexes of $^{125}$I-RIGRIVTAKY-cell surface proteins was estimated based on the migration of simultaneously run standard proteins (Amersham, Arlington Heights, Ill.); myosin (200 kDa), phosphorylase b (97.4 kDa), bovine serum albumin (69 kDa), ovalbumin (46 kDa), carbonic anhydrase (30 kDa) trypsin inhibitor (21.5 kDa), and lysozyme (14.3 kDa).

Preparation and implantation of Deptide-albumin conjugates into mice. Peptide-albumin conjugates (made with either ASRLDLRIGRIVTAKY, RIGRIVTAKY or CRAQTMANSGIK (SEQ ID NO. 16)) were prepared using glutaraldheyde as described (39). In brief, mouse serum albumin (50 µg) was incubated with glutaraldehyde (450 µg) and the indicated peptide (200 µg) in NaCl (0.1 M) Tris (0.05 M, pH 7.3) for 10 min at room temperature. Excess lysine was added (final concentration, 0.5 M), and the albumin-peptide conjugates were dialyzed exhaustively versus phosphate-buffered saline. BALB/c mice (6–12 weeks) each received an injection into the footpad (7,40–41) of 0.05 ml of a solution of either (i) albumin-peptide conjugate (50 µg, total protein/footpad), (ii) albumin treated with glutaraldehyde in an identical fashion, except that no peptide was present (50 µg, total protein/footpad), (iii) native albumin (50 µg total protein/footpad), or (iv) buffer alone. At the indicated time, animals were sacrificed by humane euthanasia, footpads were harvested, fixed in buffered formalin (10%), decalcified, and embedded in paraffin. Sections were stained with hematoxylin and eosin.

Results

Effect of N-terminal derived EMAP II peptides on PMNs and MPs. In view of the close homology between a short span of EMAP II (residues #10–20) (7) and von Willebrand factor antigen II (residues #480–490) (14–15), and the similar cytokine-like properties of these molecules (18), a peptide homologous to the N-terminal region of murine EMAP II was prepared and its effects on PMNs and MPs were tested. Since the peptide including residues #6–20 from EMAP II, ASRLDLRIGCIVTAK, proved to be unstable/insoluble, the Cys residue (residue #15) was replaced with an Arg, similar to that present in the comparable position (residue #485) in von Willebrand antigen II (14–15). Incubation of PMNs with ASRLDLRIGRIVTAKY (residues #6–20 from EMAP II, Cys to Arg substitution at position #15, and a C-terminal Tyr) led to induction of migration, compared with controls containing medium alone. In contrast, no chemotaxis was observed with a peptide derived from the C-terminal portion of EMAP II (CRAQTMANSGIK), a peptide derived from the ELR-region of IL-8 (AVLPRSAKELRL (SEQ ID NO. 17); residues #23–34) (42–43), or an irrelevant peptide derived from growth hormone (IRKDMDKVETFLRIVQ). Induction of PMN migration by ASRLDLRIGRIVTAKY (SEQ ID NO. 18) at 100 pM was roughly comparable to that observed with formulated chemotactic peptide fMLP (44) at 1 µM. The effect of ASRLDRIGRIVTAKY added to the lower well of chemotaxis chambers was dose-dependent over a range of 10–10000 pM, and at doses >1 nM reached an apparent maximum (data not shown). In four different experiments using PMNs from three individuals and multiple concentrations of peptide, half-maximal PMN migration occurred at an ASRLDLRIGRIVTAKY concentration of ≈150–300 pM. The peptide induced directional PMN migration rather than simply chemokinesis since addition of peptide to the upper well attenuated/abolished the response to ASRLDLRI-GRIVTAKY added to the lower well. In addition to stimulating PMN motility, ASRLDLRIGRIVTAKY also released PMN myeloperoxidase activity in the peroxidase generation assay, as did phorbol ester-treated positive controls. In contrast, negative controls utilizing the EMAP II C-terminal peptide (CRAQTMANSGIK) or medium alone demonstrated no induction of cell migration.

To further elucidate structural determinants in the N-terminal region of EMAP II (residues #6–20) critical for induction of PMN migration, a series of synthetic peptides was prepared (Table 4).

TABLE 4

Effect of peptides derived from the N-terminus of EMAP II on PMN migration@

| PEPTIDE | PMN MI- GRA- TION |
|---|---|
| 1. A S R L D L R I G R I V T A K Y# | + |
| 2. A S R L D L R I G R I V T A K | + |
| 3. A S R L D L R I G C*I V T A K | + |
| 4. A S R L D L | − |
| 5.             L R I G R I V T A K Y | + |
| 6.                R I G R I V T A K Y | + |
| 7.                R I G R I V T | + |
| 8.                R I G R I I T | + |
| 9.                R I G R A V T (SEQ ID NO. 19) | − |
| 10.               A I G R I V T (SEQ ID NO. 20) | + |

@Cell migration assays were performed using PMNs and peptides (100 pM in each case) as described in the text. (+) indicates the peptide induced PMN migration. (−) indicates the peptide did not induce PMN migration above levels seen in controls which contained no chemotactic stimulus. Each experiment was repeated at least three times.
Residues of peptides were assigned numbers (referred to in the text) starting with #6, N-terminal A, to #21, C-terminal Y. These numbers were based on the N-terminal protein sequence of EMAP II in which A was residue #6.
*Cys at this position was carboxymethylated.

For these studies, comparable molar concentration of peptide were employed, and where the data is reported as (+), there was a similar response (the designation [−] indicated no response above that observed in untreated control wells). The data is reported in this nonquantitative fashion because absolute numbers migrating cells vary in different assays (PMNs from different donors, assays performed on different days), though the same trend was observed over a similar range of peptide concentrations. Compared with ASRLDLRIGRIVTAKY (line 1), the peptide ASRIZLRI-GRIVTAK without an added C-terminal Tyr residue promoted PMN migration (line 2). Since we had arbitrarily replaced Cys (residue #15 in EMAP II) with Arg to enhance peptide stability, it was important to determine if this substitution, which also made the peptide more positively charged, altered its biologic properties. A peptide in which the Arg at position #15 in the peptide was replaced with carboxymethylated-Cys (line 3) was prepared and found to induce PMN migration. To determine which portion of the sixteen residue peptide was involved in the interaction with PMNs, we synthesized several shorter peptides. ASRLDL (residues #6–11; line 4), the N-terminal region of the initial peptide #6–20), was inactive in the PMN migration assay, whereas several peptides closer to C-terminus were active: LRIGRIVTAKY (#11–20; line 5), RIGRIVTAKY (#12–20; line 6), and RIGRIVT (#12–18; line 7). Our recent molecular cloning studies have shown that, in the human homologue of EMAP II, Val at position #17 in murine EMAP II is replaced by Ile; thus, the latter peptide was tested (RIGRIIT; resides #12–18; line 8) and was found to stimulate PMN migration. Whereas replacement of Ile (position #16) with Ala in this peptide rendered it inactive (RIGRAVT; line 9), substitution of Arg at position #12 with Ala (AIGRIVT, resides #12–18; line 10) resulted in a peptide which retained activity for induction of PMN migration.

When the same peptides employed in the studies with PMNs were studied for their effects on MP migration, ASRLDLRIGRIVTAKY was found to induce chemotaxis, whereas the C-terminal EMAP II-derived peptide, as well as the IL-8-derived peptide and growth hormone-derived peptide were inactive, i.e., comparable to medium alone. Migration of MPs in the presence of ASRLDLRIGRIVTAKY at a concentration of 100 pM was similar to that observed with FMLP at 1 µM. The effect of ASRLDLRIGRIVTAKY on MP migration was dependent on the amount of peptide added to the lower compartment of the microchemotaxis chamber over a similar concentration range to that observed with PMNs and the effect was prevented by addition of peptide to the upper compartment of the chamber.

In view of the similar effects of the N-terminal EMAP II-derived peptides and intact EMAP II for the induction of MP and PMN chemotaxis, experiments were performed to determine if peptides mimicked other activities of EMAP II (7). However, studies with ECs and MPs did not demonstrate induction of tissue factor activity by any of the peptides from EMAP II, based on Factor VIIa-dependent Factor X activation, when either of these cell types was incubated with a range of ASRLDLRIGRIVTAKY concentrations. In contrast, intact EMAP II stimulated tissue factor expression in ECs and MPs (7).

Binding and cross-linking of $^{125}$I-EMAP II-derived N-terminal region Deptide to MPs. To delineate further the interaction of EMAP II-derived peptides with target cells, the tyrosinated derivative of RIGRIVTAKY was radioiodinated and employed as a tracer for binding studies. Incubation of $^{125}$I-RIGRIVTAKY with MPs led to dose-dependent specific binding at 4° C. Binding data fit a one-site model with Kd=0.19±0.11 nM and N=8.3±1.2×10$^3$ molecules of peptide bound per cell. Competitive binding studies demonstrated inhibition of $^{125}$I-RIGRIVTAKY binding in the presence of increasing concentrations of unlabelled RIGRIVTAK (SEQ ID NO. 21) and ASRLDLRI-GRIVTAKY. CRAQTMANSGIK, derived from the C-terminal region of EMAP II, ASRLDL, derived from the first six amino acids of the original peptide (residues #6–20), and RIGRAVT had no effect. These data are consistent with the lack of effect on PMN chemotaxis of ASRLDL (line 4, Table 4), RIGRAVT (line 9, Table 4) and CRAQTMANS-GIK. Further evidence for the specificity of $^{125}$I-RIGRIVTAKY interaction with cellular surfaces was based on inhibition of binding on addition of excess unlabelled intact EMAP II, but not by fMLP, murine TNFA or murine Il-1α.

In order to better define MP cell surface structures with which $^{125}$I-EMAP II interacted, cross-linking studies with DSS were performed. Addition of cross-linker to MPs with cell-bound $^{125}$I-RIGRIVTAKY resulted in the appearance of a ≈73 kDa band on autoradiograms of reduced SDS-Page. The likelihood that the latter ≈73 kDa band was due to a MP polypeptide potentially contiguous to cell-bound $^{125}$I-RIGRIVTAKY was supported by the results of experiments demonstrating disappearance/striking reduction of the ≈73 kDa band when: (i) DSS was added to $^{125}$I-RIGRIVTAKY alone (i.e., MPs were omitted); (ii) DSS was omitted from incubation mixtures containing $^{125}$I-RIGRIVTAKY and MPs; (iii) excess unlabelled RIGRIVTAKY was added to reaction mixtures containing $^{125}$I-RIGRIVTAKY and MPs, and cross-linked with DSS.

EMAP II-derived N-terminal Deptide increases [Ca$^{2+}$]$_i$ in MPs and PMNs. ASRLDLRIGRIVTAKY induced a rise in [Ca$^{2+}$]$_i$ in PMNs, similar to results using the intact EMAP II molecule. The rise in [Ca$^{2+}$]$_i$ was due mainly to redistribution of Ca$^{2+}$ from intracellular stores since a similar increase was seen when the cells were incubated in Ca$^2$+-free medium containing 5 mM EGTA. Neither the shorter peptides RIGRIVT nor RIGRIVTAKY were capable of inducing a rise in [Ca$^{2+}$]$_i$ in PMNs when used at the same concentration, and the hexapepide ASRLDL, derived from the N-terminus of the larger peptide, was also inactive in this regard. Similar results were seen in MPs, except the magnitude of rise in [Ca$^{2+}$]$_i$ from peptide stimulation was less than that of PMNs. These observations indicate that ASRLDLRIGRIVTAKY, derived from the N-terminus of EMAP II, results in elevation of [Ca$^{2+}$]$_i$ in PMNs and MPs, but that a rise in [Ca$^{2+}$]$_i$ is not necessary for migration per se since the shorter migration-inducing peptides did not promote enhanced [Ca$^{2+}$]$_i$.

Implantation of EMAPII-derived Deptide-albumin conjugates into mice. To complement in vitro studies, experiments were performed in vivo to determine if the peptide had the ability to incite an inflammatory response. The mouse footpad was selected as a model system for these experiments since it is well-characterized and provides a relatively confined space for testing the host response to inflammatory cytokines, such as intact EMAP II as will as other mediators (7,40–41). Initial experiments employing ASRLDLRIGRIVTAKY injected subcutaneously into mice demonstrated at most a transient inflammatory response, probably due to rapid diffusion of the small peptide away from the implantation site. For this reason, ASRLDLRI-GRIVTAKY and RIGRIVTAKY were conjugated to albumin using glutaraldehyde, and the experiments were repeated. First, we verified the chemotactic activity of peptide-albumin conjugates in vitro with MPs and PMNS; ASRLDLRIGRIVTAKY-albumin induced both MP and PMN migration compared with medium alone. In contrast, neither albumin treated with glutaraldehyde nor albumin alone induced migration. In other experiments, RIGRIVTAKY-albumin conjugates were shown to have chemoattractant properties for PMNs and MPs, whereas CRAQTMANSGIK-albumin did not. When ASRLDLRIGRIVTAKY-albumin or RIGRIVTAKY-albumin was injected into mouse footpads, tissue infiltration with inflammatory cells, especially PMNs, was observed (shown at 6 hr in FIG. 3), whereas the same amount of albumin or glutaraldehyde-treated albumin was without effect. In contrast, footpads injected with CRAQTMANSGIK-albumin were indistinguishable from untreated controls.

Discussion

EMAP II, a novel polypeptide mediator made by the immunogenic murine meth A fibrosarcoma, modulates cellular properties resulting in induction of tissue factor in ECs, in tissue factor and cell migration in MPs, and in cell migration and release of myeloperoxidase in PMNs (7 and unpublished observation). Based on the activities of EMAP II in vitro, and its ability to induce an acute inflammatory response in vivo (7), it was hypothesized that it may contribute to the host response elicited by immunogenic tumors (1–4). To define regions of EMAP II which are recognized by putative receptors on target cells, it is demonstrated that synthetic peptides comprising fifteen amino acids near the N-terminus of murine EMAP II (residues #6–20) promote PMN and MP migration, elevate $[Ca^{2+}]_i$, and lead to release of PMN peroxidase activity. These data, in addition to the demonstration that albumin conjugates of EMAP II-derived N-terminal peptides lead to an inflammatory infiltrate when injected into mouse footpads, support the concept that this peptide comprises a functional domain of EMAP II.

Our first structure-function studies of the peptide demonstrated that although ASRLDLRIGRIVTAKY stimulated both chemotaxis and increase cytosolic calcium in MPs and PMNS, the shorter peptide RIGRIVT was sufficient to stimulate chemotaxis, but insufficient to promote increases in $[Ca^{2+}]_i$. Thus, RIGRIVT is an example of a stimulus which promotes cell migration without altering cytosolic calcium, as had been observed with tumor necrosis factor-α (45 and S. Greenberg, unpublished observation). This suggests that the longer peptide, ASRLDLRIGRIVTAKY, might have two functional domains, whereas the shorter peptide, RIGRIWV, had more limited activity. In view of the lack of calcium mobilizing activity of ASRLDL, we hypothesize that attachment of these residues to RIGRIVTAK is required for cellular association and subsequent stimulation of $[Ca^{2+}]_i$. The results of radioligand binding studies on MPs supported this view, since binding of $^{125}$I-RIGRIVTAKY to cells was blocked by excess unlabelled RIGRIVT and ASRLDLRIGRIVT (SEQ ID NO. 23), but not ASRLDL. Analysis of residues within the septa-peptide RIGRIVT that contribute to induction of PMN migration has demonstrated the importance of the sequence XIGXI(V/I)T (SEQ ID NO. 24 and 25), although further studies will be necessary to precisely determine structure-function relationships.

Experiments with $^{125}$I-RIGRIVTAKY demonstrated specific and saturable binding to human MPs. Pilot studies using ECs also show specific binding of this peptide (data not shown). Competition studies in which neither murine TNFα, IL-1α, nor fMLP inhibited binding of $^{125}$I-RIGRIVTAKY to MPs suggested that cell surface acceptor sites interact specifically with EMAP II-related ligands. Consistent with the potential selectivity of EMAP II-derived peptide-cell surface interaction, cross-linking studies with $^{125}$I-RIGRIVTAKY labelled and ≈73 kDa MP surface polypeptide. The potential uniqueness of the cellular recognition site for the N-terminal region of EMAP II was also suggested by our recent molecular cloning studies which have shown that its ligand, EMUS II, is novel, and is not, on the basis of primary structure, a member of either a known cytokine (such as IL-1 or TNF) (46–47) or chemokine (IL-8 and related murine homologs) (48) family.

Taken together, these data provide a starting point for more detailed structure-function studies of EMAP II, and highlight contributions of an N-terminal functional domain for modulation of MP and PMN properties. However, it is important to note that none of the peptides studied fully mimicked the cellular effects of intact EMAP II. For example, even the longest peptide (residues #6–20) did not induce tissue factor in ECs or MPs. Thus, there are likely to be several functional domains which account for EMAP II-induced modulation of cellular functions. In this context, the design of peptide agonists and antagonists of the N-terminal region may provide valuable reagents for analyzing cellular effects of EMAP II and isolating the putative cell surface receptor.

C. cDNA Clone and Recombinant EMAP II

Materials and Methods

Isolation of Meth A cell RNA. Meth A cells were grown in RPMI 1640 containing fetal bovine serum (10%; Hyclone, Sterile Systems, Logan, Utah) to ≈90% confluence, cells were harvested (≈$10^8$) with trypsin, resuspended in fetal bovine serum (10%), and poly(A)$^+$RNA isolated directly as described (Bradley 1988). Briefly, cells were lysed in SDS-containing buffer and proteins were digested with proteinase K (Boehringer Mannheim, Indianapolis, Ind.) for 3 hr at 55° C. Oligo(dt)cellulose (Collaborative Biomedical, Bedford, Mass.) was added and the poly(A)$^+$RNA removed by centrifugation and then eluted with water. A second step in the purification utilized oligo (dt) cellulose bound to magnetic beads (Promega, locationx) by a similar procedure.

Isolation of murine cDNA clones. Meth A mRNA (1 µg) was denatured with MeHgOH and reverse transcribed with AMV reverse transcriptase using oligo(dt) $_{17}$ as a primer. The first strand cDNA obtained was used as template for the polymerase chain reaction (PCR) using degenerate primers based on the amino terminal protein sequence obtained for EMAPII. The sense primer was 5'-AARCCNATHGAYGC-3'(SEQ ID NO. 26) and the antisense primer was 5'-YTTNGCNGTNACDAT-3'(SEQ ID NO. 27), 48- and 184-fold degenerate, respectively. In addition, both primers contained EcoRI sites to facilitate cloning of the PCR products. The thermocyte parameters consisted of three cycles of 95° C. for 30 sec, one min to reach 37° C., 30 sec at 37° C., 2.5 min to 72° C., one min at 72° C., and one min to reach 95°. This was followed by 30 cycles of 30 sec at 95° C., 30 sec at 55° C., and one min at 72° C. Analysis of the amplified products on an acrylamide gel showed a DNA fragment of the expected size of 77 bp. The PCR products were then digested with EcoRI, run on an acrylamide gel, the appropriate band excised and eluted, and the DNA fragment cloned into the plasmid vector pUC219. Plasmids containing EcoRI inserts were sequenced by the Sanger dideoxynucleotide method using Sequenase (US Biochmical Corp.). The deduced amino acid sequence was found to match exactly that obtained by protein sequencing. A 57-mer nucleotide probe was designed based on the consensus nucleotide sequence obtained from sequencing several clones, as follows: (5'-AAGCCCATTGATGCCTCCCGGCTGGAC-CTGCGGATTGCTGCATTGTGACAGCCAAG-3'(SEQ ID NO. 28)). This probe was end-labelled with [τ³²P]dCTP using polynucleotide kinase and employed to screen a Meth A cDNA library in the lambda vector HEB05 (Leung et al, 1992). Hybridization was in formamide (20%), SSC (5×), sodium phosphate (50 mM; pH 6.5), denatured salmon sperm DNA (40 μg/ml), SDS (0.1), and Denhardt's solution (5×) at 42° C. One positive plaque was identified which contained a 700 bp insert. A second library, in lambda-gt10, was constructed from cDNA primed with a specific primer, 5'-ATTTTGCATCTGITTCTAG-3'(SEQ ID NO. 29), complementary to sequence near the 5'-end of the original clone. This library was screened with the same oligonucleotide probe described above under the same conditions. Eight positive plaques were obtained from ≈10⁵ screened. The three with the longest inserts, all ≈300 bp, were subcloned into the EcoRI site of pUC219 and sequenced. When this sequence was overlapped with the original clone, an 1086 bp sequence was obtained. A full length EMAPII cDNA was constructed in the Epstein-Barr virus-based vector, pHEBO23 (Leung et al, 1992), by joining the two fragments at the XbaI restriction site present in both pieces.

Cloning of the Human EMAPII cDNA. Low strigency Northern analysis of human U937 mRNA using a murine probe suggested the EMAPII transcript was expressed by this cell line (data not shown). Thus, an oligo(dt)-primed U937 library in lambda-gt10 (kindly provided by Brain Bennet, Genetech, So. San Francisco, Calif.) was screened. Plaques (≈10⁶) were screened using a probe consisting of the first 310 nucleotides at the 5'-end of the murine EMAP II clone. This ClaI (in the vector polylinker) to ScaI (500 bp) fragment ws nick-translated and hybridized in formamide (20%), sodium phosphate (50 mM; pH 6.5), SSC (5×), DenhardtIs solution (5×), SDS (0.1%), and denatured salmon sperm DNA (40 μg/ml) at 42° C. About 20 positives were obtained, and ten of these were purified. The three which contained the longest inserts appeared to have identical 1100 bp EcoRI inserts. These inserts were subcloned in pUC219 and sequenced.

Northern analysis of Meth A cell mRNA for EMAPII expression. Poly(A)⁺RNA from MethA sarcoma cells was denatured and electrophoresed on an agarose gel (1.2%) in MOPS-formaldehyde (Sambrook et al, 1989). The RNA was transferred to nitrocellulose (Schleicher and Schuell) and prehybridized in formamide (50%), sodium phosphate (50 mM; pH 6.5), SSC (5×), Denhardt's solution (5×), SDS (0.1%), and denatured salmon sperm DNA (40 μg/ml) at 42° C. A 279 bp DNA fragment was isolated from the murine EMAPII clone following XbaI and SacI digestion corresponding to nucleotides 652–930. This was nick-translated with [α³²P] dCTP and hybridized to the blot overnight. Washing was performed at a final stringency of SSC (0.2×)/SDS (0.1%) at 55° C. The blot was then exposed overnight for autoradiography.

E. coli expression of murine EMAPII. In order to confirm the biological activity of the protein encoded by the cloned DNA sequence, the region corresponding to the predicted mature protein, based on the N-terminal sequence obtained from purified EMAPII, was expressed. This was accomplished using a fragment of the murine clone extending from the BstB I site (nucleotide 529) to the 3'-untranslated region and synthetic DNA encoding the N-terminal end, KPIDA-SRLEL (SEQ ID NO. 30) (5'TATGAAACCAATCGATG-CATCTCGTCTGGATCTT-3'(SEQ ID NO. 31) AND 5'-CGAAGATCCAGACGAGATGCATCGATTGGTT-TCA-3'). This sequence, which differs from the amino terminal region obtained by microsequencing because the N-terminal residue, serine, was inadvertently omitted when designing the synthetic DNA, was cloned into the NdeI site, containing the ATG initiation codon, and the BamHI site of the vector pET-3a in which cDNA expression is driven by the T7 promoter (novagen). The protein was then expressed in the host HMS174(DE3) which contains the T7 RNA polymerase gene under control of the lacUV5 promoter. Following growth to log phase the T7 polymerase was induced with IPTG (0.4 mM) and the cells were harvested by centrifugation 3 hr later.

Transfection of Meth A cells. Meth A cells, a methylcholanthrene A-induced fibrosarcoma originally derived from BALB/c mice were generously provided by Dr. L. Old (Ludwig Cancer Inst., New York). Cells were grown in RPMI 1640 (Gibco BRL, Grand Island, N.Y.) containing fetal calf serum (10%; HyClone Laboratories, Logan, Utah) penicillin/streptomycin (1×; Gibco BRL), and L-glutamine (2 mM) (this is termed complete medium-CRPMI), and maintained at 37° C. in a humidified, 5% $CO_2$ atmosphere. The medium for selection of transfectants contained G418 (400 μg/ml; Gibco BRL). Full-length EMAP II cDNA was subcloned into the pRK5 plasmid. Exponentially growing Meth A cells were transfected with Cel-Porator electroporation System I (Gibo BRL). Briefly, serum-free RPMI (1 ml) containing meth A cells (2×10⁶), pRK5-proEMAPII cDNA (20 μg), and pRK5-Neo DNA (1 μg; containing the G418 resistence gene) was transferred into the electorporation chamber, and the electorporation ws conducted at 250 V. After transfection, the cells were incubated for 15 min at 23° C., and then transferred to CRPMI (15 ml). After a further 24 hrs, cells were pelleted, resuspended in the selective medium containing G418 (400 μg/ml), and aliquoted into four 48-well plates. Cells were re-fed with selective medium every three days, and 2–3 weeks later colonies became visible. Wells with a single colony were chosen for expansion. Production of EMAPII antigen was quantitated by ELISA.

Preparation of and in vitro assays with endothelial cells, mononuclear phagocytes (MPs), polymorphonuclear leukocytes (PMNs). Human umbilical vein ECs were prepared by the method of Jaffee et al as modified by Thornton et al, as done previously (7). Bovine aortic ECs were harvested fron the aortae of veal calves and grown in culture as described previously. Human peripheral blood monocytes were isloated from the blood of normal healthy volunteers. Blood was centrifuged on Histopaque 1077 (Sigma), the mononuclear fraction was obtained, washed twice in Earle's balanced salt solution, resuspended in RPMI 1640 containing human serum (10%, Gemini, Calabases, Calif.), plated on tissue culture dishes, and incubated at 37° C. for 1–2 h. Nonadherent cells were removed by washing the plate twice with balanced salt solution, and adherent cells were harvested by incubation with calcium-magnesium free buffer containing EDTA (2 mM) for 15 min at 37° C., followed by extensive washing. PMNs were prepared by centrifugation over histopaque 1119 according to the manufacturer's protocol (Sigma).

Results cDNA cloning of EMAPII. Purification of EMAPII from conditioned medium of murine meth A sarcoma yielded an ≈22 kDa protein from which an unique amino terminal sequence was obtained. Degenerate oligonucleotide primers were designed to generate a 77 bp fragment encoding a portion of the N-terminal sequence by PCR. The sequence obtained was then used as the basis for design of a 57 base oligonucleotide probe for screening a meth A oligo(dt)-primed cDNA library. One clone, 680 bp, was isolated and represented a partial cDNA sequence with an open reading frame at the 5'-end. A second meth A cDNA library was constructed using a specific primer based on the first sequence obtained, and the same 57 base probe was used to identify 8 clones. Three of these appeard to have identical inserts of 660 bp based on restriction analysis, and the sequence obtained from these clones was overlapped with that of the original clone to produce contiguous sequence of 1086 bp (FIGS. 4-1–4-2). Northern blot analysis of RNA from Meth A cells using a 275 bp XbaI to SacI fragment as a probe demonstrated a single transcript of approximately 1070 bp suggesting the cDNA clone was full-length. Analysis of this sequence revealed an open reading frame containing residues encoding the N-terminal sequence with a termination codon at the nucleotide 894 followed by a polyadenylation signal (AATAAA). There are three ATG codons in this reading frame in the first 200 nucleotides of the cDNA with no upstream stop codons. However, only the second, at position 64, meets the criteria of Kozak (1989) for initiation of translation. Thus, using codon 64 as the start codon, the open reading frame would encode a protein of 310 amino acides with a predicted molecular wieght of ≈34 kDa. A fragment of the murine cDNA was used as a probe to isolate a full-length human cDNA clone for EMAPII from a lambda gt 11 U937 monocyte library (FIGS. 4-1–4-2). Compared with murine EMAPII, the human cDNA was 86% identical, and the deduced sequence contained an additional two amino acids. The ATG designated as the start codon and the upstream ATG are both conserved in the human cDNA.

Since the N-terminal sequence obtained from the purified EMAPII is encoded by an internal sequence of the EMAPII clone, it was predicted that mature EMAPII results from processing from a larger polypeptide. The cDNA corresponding to the N-terminal, processed portion of the sequence encodes 165 amino acids which would result in a polypeptide of ≈18 kDa, in close agreement with the ≈22 kDa observed for EMAPII purified from meth A sarcoma cells. Although EMAPII is apparently secreted by meth A sarcoma cells, a hydropathy analysis of the predicted murine primary amino acid sequence lacked evidence for a hydrophobic signal peptide. Of note is that, both the predicted size of the protein before cleavage, as well as the cleavage site of this protein, are reminiscent of another secreted cytokine which also lacks a classical signal peptide, interleukin-1β (IL-1β). The mRNA for IL-1β encodes a 31 kDA precursor to the mature 17 kDA from (March et al, 1985), and proteolytic processing releases a 17 kDa secreted, active IL-1β (Black, 1989). An Asp in the P1 position of IL-1β is necessary for cleavage by the cysteine protease IL-1β converting enzyme (ICE) to yield the active 17 kDa IL-1β (Thronberry et al, 1992; Cerretti, 1992). In EMAPII, an Asp is present in the P1 position in both the murine and the human forms (FIG. 4-1, arrow). Thus, a cystine protease similar or identical to ICE might be responsible for producing mature EMAPII from its pro-from. Supportive of the idea that the mature form is the biologically active protein, sequence conservation is 95% between the murine and the human region of the mature polypeptide, but drops to 74% in the putatuive pro-region.

The primary amino acid sequence of EMAPII shows little homology to any other proteins in the data banks. Nevertheless, a limited resemblance exists between residues in the N-terminal portion of EMAPII and several other cytokines, notably IL-8 and IL-1β, as well as von Willebrand antigen II, a product released by activated platelets and endothelial cells. All of these molecules share chemoattractant properties towards neutrophils and/or monocytes (Yoshimira, 1987; Sauder, (18)). For IL-8, Hebert et al (1991) have demostrated by in vitro mutagenesis that changing residues in this area, E31, L32, R33, or I37, to alanine resulted in a molecule incapable of mobilizing calcium in neutrophils and having reduced ability to compete with native IL-8 for binding to neutrophil IL-8 receptors.

Expression of Murine EMAPII in E coli. E. coli transfected with the portion of the EMAPII CDNA corresponding to mature EMAPII were pelleted by centrifugation, sonicated in the presence of tris-buffered saline, and the supernatants chromatographed on FPLC Mono Q. The peak containing EMAPII activity was identified based on the induction of tissue factor activity in ECs. In contrast, little protein eluted at a similar salt concentration from material obtained from E. coli transformed with vector alone, and this small peak had no significant tissue factor inducting activity. The material from the Mono Q activity peak of the E. coli transfected with the construct containing EMAPII cDNA was pooled, concentrated, and subjected to nonreduced SDS-PAGE. Silver staining revealed a complex pattern of bands, although elution of material from an identical lane of the gel demonstrated that only material with Mr ≈18 kDa had the capacity to induce tissue factor in ECs. This material was re-run on SDS-PAGE, and a single band was observed under both reduced and non-reduced conditions, the latter having the capacity to induce EC tissue factor. Western analysis with an antibody raised to a peptide comprising ASRLDLRIGRIVTAK of EMAPII visualized the ≈18 kDa band purified from E. coli transfected with the EMAPII cDNA, whereas no band was observed when the control vector was used.

D. Treatment of Tumors

Experiment 1: Localized Thrombohemorrhage

Normal C3H/He mice were injected intradermally with 20 micrograms of EMAP II. Each mouse received 100 micrograms of endotoxin, systemically, either 9, 15, or 18 hours after the EMW II. Skin was harvested three hours later. In each case, localized hemorrhage was observed in the skin, at the site of the initial EMAP II injection.

Experiment 2: Localized Thrombohemorrhage

Normal Balb/C mice were injected intradermally with 20 micrograms EMAP II. Each mouse received 100 micrograms of endotoxin, systemically, either 18 or 24 hours after the EMAP II. Skin was harvested three hours later. In each case, localized hemorrhage was observed in the skin, at the site of the initial EMAP II injection.

Experiment 3: Hemorrhage in Meth A Fibrosarcomas

Methycholanthrene A-induced fibrosarcomas (meth A) were raised in the backs of C3H/He mice by intradermal injection of $2 \times 10^5$ tumor cells. Seven days later, mice were given a single intratumor injection of either purified recombinant human Tumor Necrosis Factor (TNF, 5 micrograms, in a PBS/albumin vehicle), heat treated TNF (inactivated by 15 minutes in a boiling water bath), EMAP II (20 micrograms in the vehicle), heat-treated EMAP II, or vehicle solution alone. Six hours after injection, mice were sacrificed and tumors were observed for the presence of gross hemorrhage. EMAP II elicited gross hemorrhage in a proportion of tumors comparable to TNF, but the controls were without appreciable effect. (FIG. 5).

Experiment 4: Hemorrhage in Mouse Mammary Carcinomas (Single Injections)

Figure 6:
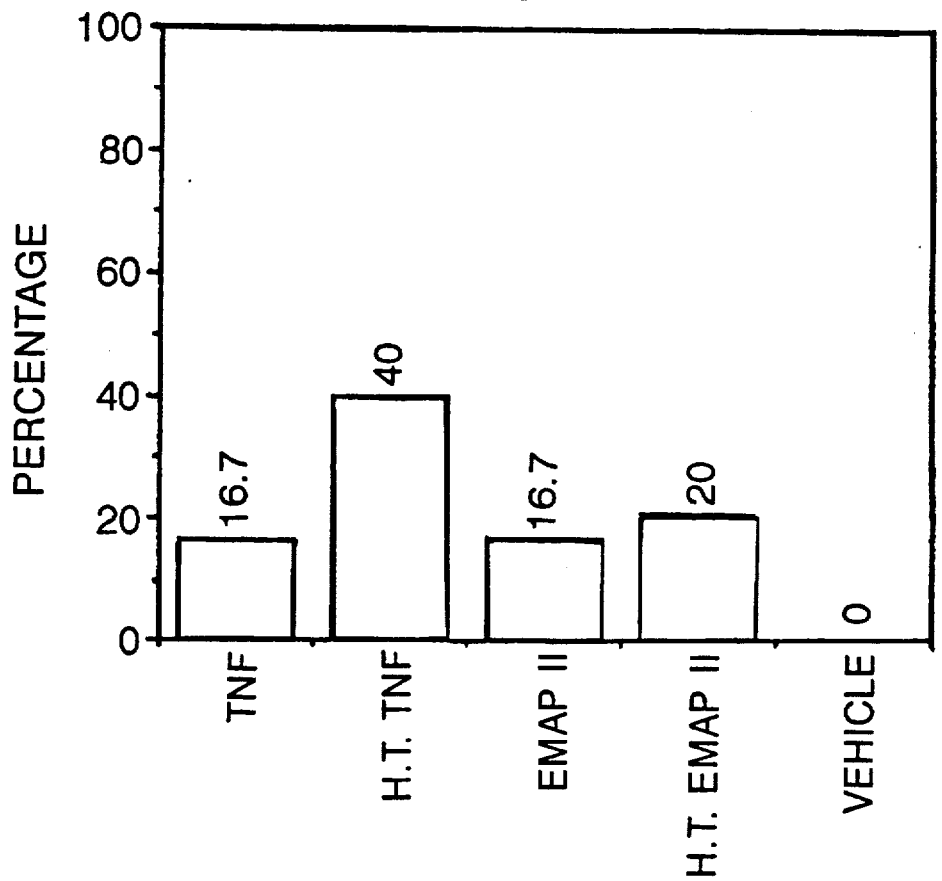

Mouse mammary carcinomas derived from MC2 cell line were raised in the backs of C3H/He mice by intradermal injection of $10^6$ tumor cells. Seven days later, mice were given a single intratumor injection of 5 micrograms TNF, heat-treated TNF, 20 micrograms EMAP II, heat-treated EMAP II, or vehicle alone. Six hours later, mice were sacrificed and tumors were observed for the presence of gross hemorrhage. No treatment elicited hemmorhage above baseline. (FIG. 6).

Experiment 5: Hemorrhage in Mouse Mammary Carcinomas (Dual Injections)

Figure 7:
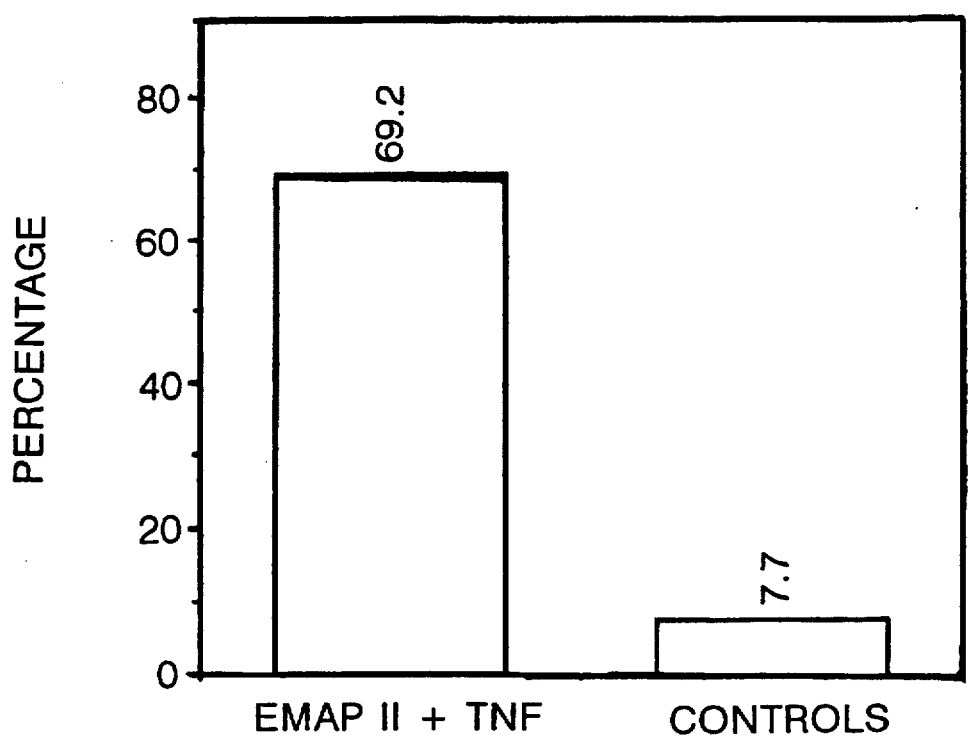
Figure 8A:
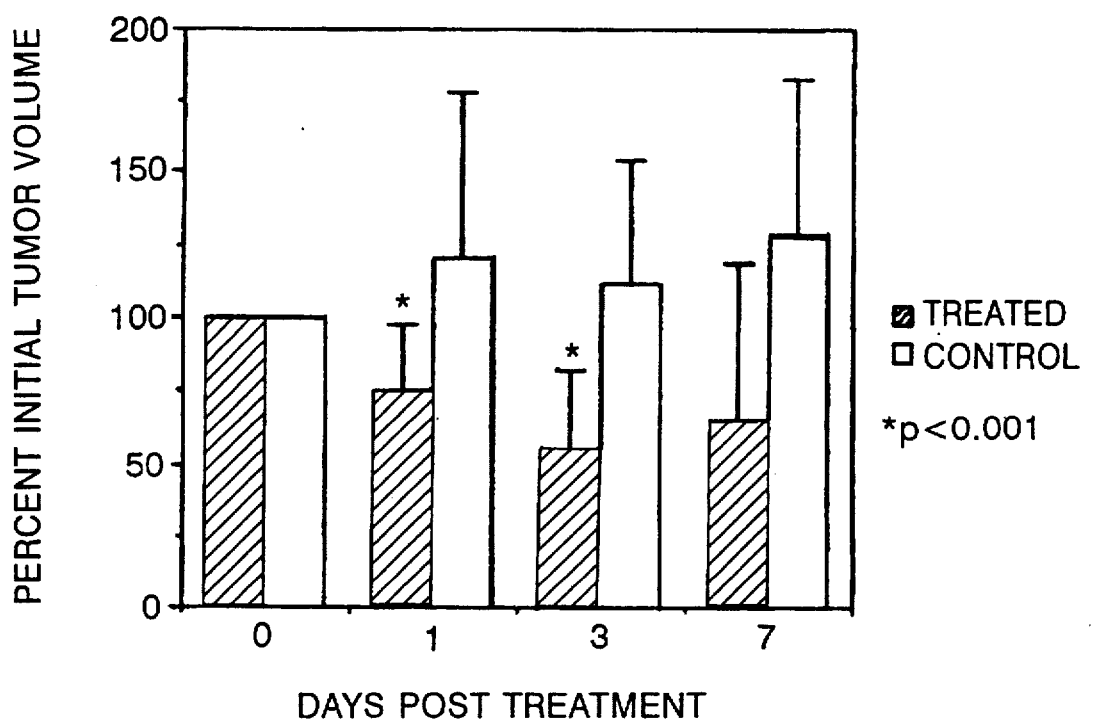
Figure 8C:
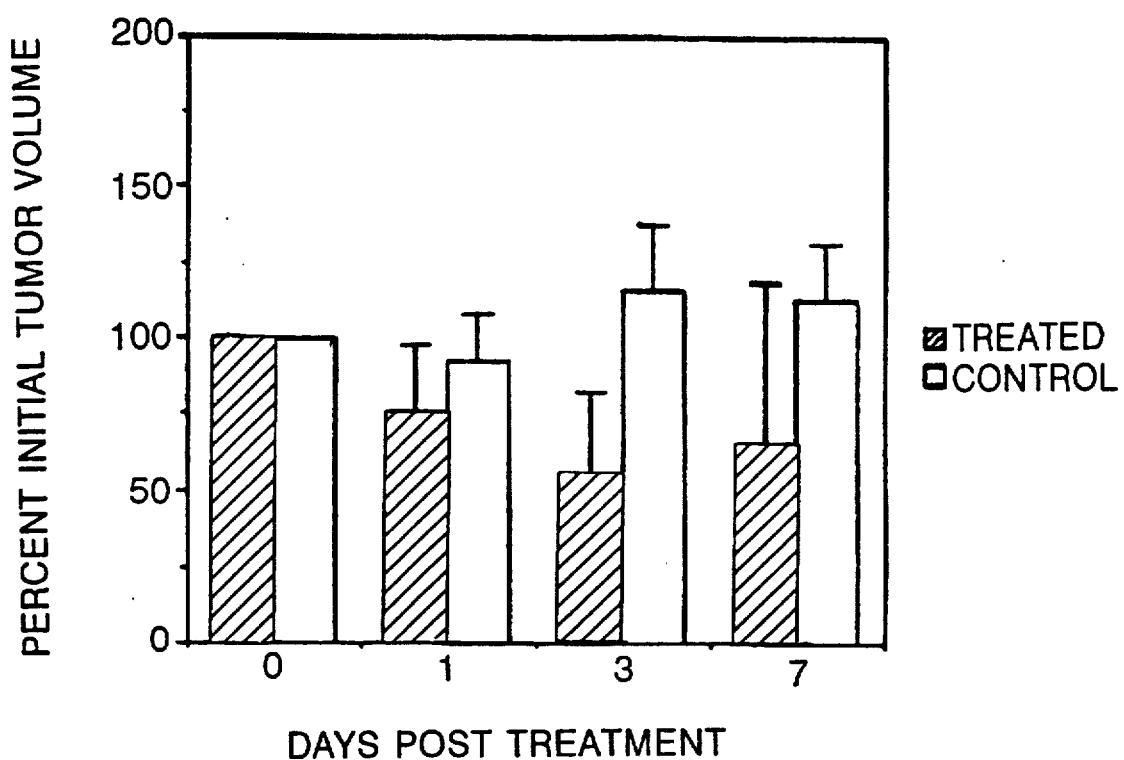
Figure 8D:
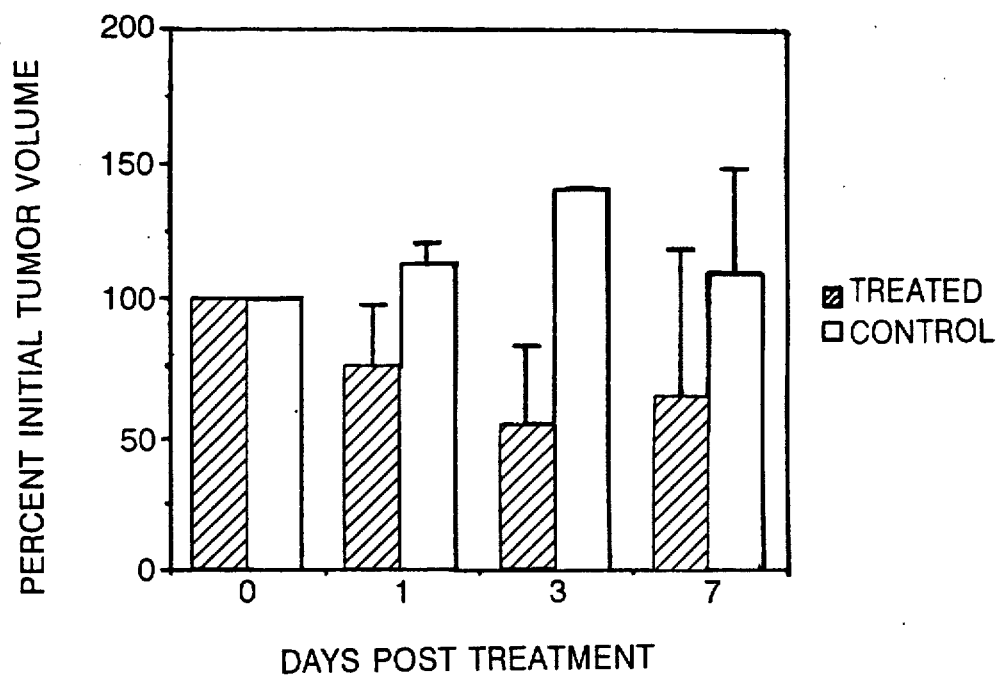
Figure 8E:
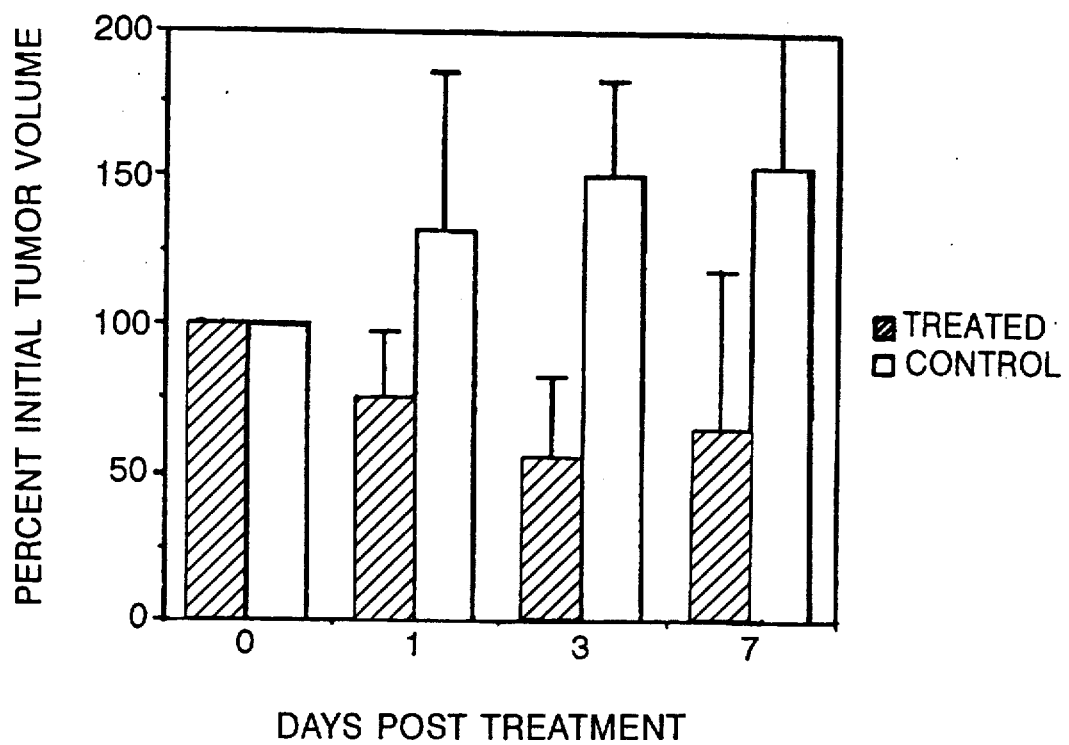

Mouse mammary carcinomas derived from the MC2 cell line were raised in the backs of C3H/He mice by intradermal injection of $10^6$ tumor cells. Six days later, mice received intratumor injections of 20 micrograms EMAP II followed 12–18 hours later by a systemic dose of 5 micrograms TNF. Control animals received combinations of either heat-treated (H.T.) EMAP II+TNF, EMAP II+H.T. TNF, H.T. EMAP II+H.T. TNF, or vehicle+TNF. Tumors were excised six hours following the second (systemic) injection and examined for the presence of gross hemorrhage. (FIG. 7).

Experiment 6: Tumor Regression Following EMAP II+TNF Treatment

Mouse mammary carcinomas were treated as in experiment 5 with a local injection of 20 micrograms EMAP II followed 12–18 hours later by a systemic dose of 5 micrograms TNF, with control animals receiving heat-treated cytokines or vehicle. Length, width and height of each tumor was measured prior to the systemic dose and again on days 1, 3, and 7 after the systemic injection. Tumor volume was calculated by assuming the shape of each tumor was that of a spherical segment, and according to the formula:

$$V=(pi/6)h(h^2+3a^2)$$

where a is taken as half the average of the length and width of the tumor base. EMAP II+TNF treatment is compared with each combination of heat-inactivated control, as well as to vehicle+TNF. (FIGS. 8A–E).

Experiment 7: Tumor Regression Following EMAP II+EMAP II Treatment vs. Tumor Regression Following EMAP II+TNF Treatment Mouse mammary carcinomas were raised as above but given a local injection Of 20 micrograms EMAP II followed 12–18 hours later by a systemic dose of 40 micrograms EMAP II. Tumor volume was calculated as in Experiment 6, and comparison was made with control tumors as well as EMAP II+TNF-treated tumors from Experiment 6. Local EMAP II followed by systemic EMAP II produced tumor regression to a greater degree than local EMAP II followed by systemic TNF. (FIG. 9).

Experiment 8: Clonocenic Cell Viability Assay (2.3) Following EMAP II+TNF

Figure 10:
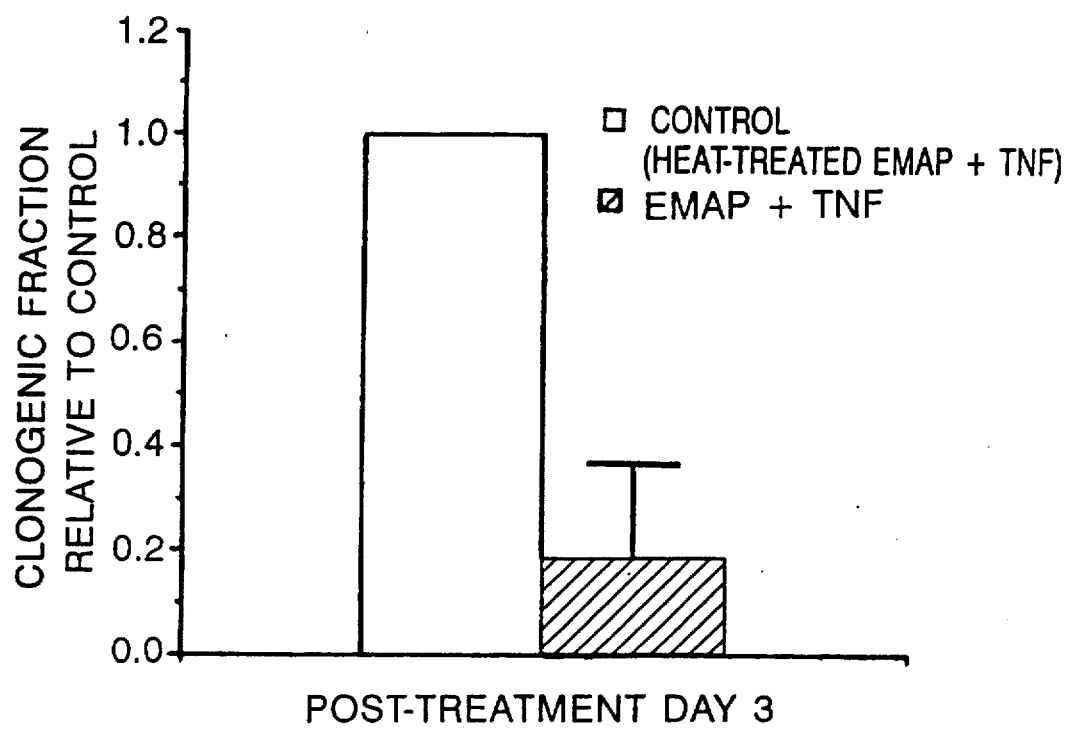

Mouse mammary carcinomas were raised as above and treated with 20 micrograms EMAP II by intratumor injection, followed 18 hours later by 5 micrograms TNF by systemic injection. On the third day after treatment, tumors were aseptically excised, digested, and washed; cells were counted and placed in culture medium for four days, at which time the number of dividing colonies was assessed. The number of dividing colonies divided by the number of cells retrieved from the tumors was taken as the surviving clonogenic fraction; this was compared with the surviving clonogenic fraction from tumors treated with heat-inactivated EMAP II plus active TNF. (FIG. 10).

REFERENCES FOR THE FIRST SERIES OF EXPERIMENTS

A. Endothelial Monocyte Activating Polypeptide II

1. Quintana, A., E. Raczyka, Z. Latellio, and M. Donati. 1983. Eur. J. Cancer Clin. Oncol. 19:1031–1035.
2. Murray, J., K. Smith and G. Thurston. 1989. Brit. J. of Cancer 60:729–733.
3. Old., L. 1986. Science 230:630–632.
4. Haranaka, K., N. Satomi, and A. Sakurai. 1984. Int. J. Cancer 34:263–267.
5. Asher, A., J. Mule, C. Reichert, E. Shiloni, and S. Rosenberg. 1987. J. Immunol. 138:963–974.
6. Palladino, Jr., M., M. Shalaby, S. Kramer, D. Ferraiolo, R. Baughman, A. Deleo, D. Crase, B. Marifino, B. Aggarwal, I. Figari, D. Liggitt, and J. Patton. 1987. J. Immunol. 138:4023–4032.
7. Nawroth, P., D. Handley, G. Matsueda, R. De Waal, H. Gerlach, D. Blohm, and D. Stern. 1988. J. Exp. Med. 168:6637–647.
8. Sugarman, B. J., B. B. Aggarwal, P. Hass, I. Figari, M. Palladino, and H. Shepard. 1985. Science 230:943–945.
9. Clauss, M., J. Murray, M. Vianna, R. De Waal, G. Thurston, P. Nawroth, H. Gerlach, M. Gerlach, R. Bach, P. Familletti, and D. Stern. 1990. J. Biol. Chem. 265:7078–7083.
10. Clauss, M., J. Kao, S. Koga, J. Brett, J. Ryan, and D. Stern. 1991. Blood 78:376(Abstract).
11. Old, L., B. Benacerraf, D. Clarke, E. Carswell, and E. Stockert. 1961. Cancer Res. 21:1281–1300.
12. Familletti, P., and J. Fredericks. 1988. BioTechnology 6:41–44.
13. Jaffe, E., R. Nachman, C. Becker, and C. Minick. 1973. J. Clin. Invest. 52:2745–2753.
14. Thornton, S., S. Mueller, and E. Levine. 1983. Science 222:623–626.
15. Laemmli, U. 1970. Nature 227:680–685.
16. Matsudaira, P. 1987. J. Biol. Chem. 262:10035–10038.
17. Devereux, J., P. Haeberli, O. Smithies. 1984. Nucleic Acids Res. 12:387–395.
18. Anderson, P. 1985. Anal. Biochem. 148:105–110.
19. Humphreys, M., and S. Hopkins. 1989. J. Immunol. Methods 120:271–276.
20. Ruff, M., and G. Gifford. 1980. J. Immunol. 125:1671–1677.
21. Lerner, R., N. Green, H. Alexander, F. T. Liu, J. G. Sutchiffe, and T. Shinnick, 1981. Proc. Natl. Acad. Sci. (USA) 78:3403–3407.
22. Clauss, M., M. Gerlach, H. Gerlach, J. Brett, F. Wang, P. Familletti, Y-C. Pan, J. Olander, D. Connolly, and D. Stern. 1990. J. Exp. Med. 172:1535–1545.
23. Towbin, H., T. Staehelin, and J. Gordon. 1979. Proc. Natl. Acad. Sci. (U.S.A.) 76:4350–4364.
24. Johnson, D. A., J. W. Gautsch, J. R. Sportsman, and J. H. Elder. 1984. Gene Anal. Tech 1:3–8.
25. Kaye. J., S. Porcelli, J. Tite, J. Barry, and C. Janeway. 1983. J. Exp. Med. 158:836–856.
26. Bach, R., R. Gentry, and Y. Nemerson. 1986. Biochemistry 25:4007–4020.
27. Chomczynski, P., and N. Sacchi. 1987. Anal. Biochem. 162:156–159.
28. Conway, E., R. Bach, R. Rosenberg, and W. Konigsberg. 1989. Thromb. Res. 53:231–241.
29. Maier, J., P. Voulalas, D. Roeder, and T. Maciag. 1990. Science 249:1570–1574.
30. Quinn, M., S. Parthasarathy, L. Fong, and D. Steinberg. 1987. Proc. Natl. Acad. Sci. (U.S.A.) 84:2995–2998.
31. Granstein, R., R. Margolis, S. Mizel, and D. Sauder. 1986. J. Clin. Invest. 77:1020–1027.
32. McCarroll, D., E. Levin, and R. Montgomery. 1985. J. Clin. Invest. 75:1089–1095.
33. Verweij, C., P. Diergaarde, M. Hart, and H. Pannekoek. 1986. EMBO J. 5:1839–1847.
34. Bevilacqua, M., J. Pober, G. Majeau, R. Cotran, and M. Gimbrone. 1984. J. Exp. Med. 160:618–623.
35. Nawroth, P., D. Handley, C. Esmon, and D. Stern. 1986. Proc. Natl. Acad. Sci. 83:3460–3464.

36. Nawroth, P. and D. Stern. 1986. J. Exp. Med. 164:740–745.
37. Bevilacqua, M., J. Pober, G. Majeau, W. Fiers, R. Cotran, and M. Gimbrone. 1986. Proc. Natl. Acad. Sci. (U.S.A.) 83:4533–4537.
38. Dvorak, H. 1986. New Engl. J. Med. 315:1650–1658.
39. Dvorak, H., A. Dvorak, E. Manseau, J. Wiberg, and W. Churchill. 1979. J. Natl. Cancer Inst. 62:1459–1466.
40. Karpati, R., S. Banks, B. Malissen, S. Rosenberg, M. Sheard, J. Weber, and R. Hodes. 1991. J. Immunol. 146:2043–2051.
41. Webb, D., H. Mostowski, and T. Gerrard. 1991. J. Immunol. 146:3682–3686.
42. Senger, D., S. Galli, A. Dvorak, C. Perruzii, V. Harvey, and H. Dvorak. 1983. Science 219:983–985.
43. Keck, P., S. Hauser, G. Krivi, K. Sanzo, T. Warren, J. Feder, and D. Connolly. 1989. Science 246:1309–1312.
44. Connolly, D., D. Heuvelman, R. Nelson, J. Olander, B. Eppley, J. Delfino, N. Siegel, R. Leimbruber, and J. Feder. 1989. J. Clin. Invest. 84:1470–1478.
45. Ferrara, N., and W. Henzel. 1989. Biochem. Biophys. Res. Comm. 161:851–858.
46. Leung, D., G. Cachianes, W-J. Kuang, D. Goeddel, N. Ferrara. 1989. Science 246:1306–1309.

B. Peptide Derived from Amino Terminus of EMAP II
1. Dvorak, H. (1986) New Engl. J. Med. 315, 1650–1658.
2. Dvorak, H., Dvorak, A., Manseau, E., Wiberg, J., and Churchill, W. (1979) J. Natl. Cancer Inst. 62, 1459–1466.
3. Karpati, R., Banks, S., Malissen, B., Rosenberg, R., Sheard, M., Weber, J., and Hodes, R. (1991) J. Immunol. 146,2043–2051.
4. Old, L. (1990). In *Tumor Necrosis Factor: Structure, Mechanism of Action, Role in Disease, and Therapy.* Eds. Bonavida, B. and Granger. Publ. S. Karger, Basel. pp 1–30.
5. Clauss M., Murray, J., Vianna, M., DeWaal, R., Thurston, G., Nawroth, P., Gerlach, H., Gerlach, M., Bach, R., Familletti, P., and Stern, D. (1990) J. Biol. Chem. 265:7078–7083.
6. Clauss, M., Gerlach, M., Gerlach, H., Brett, J., Wang, F., Familletti, P., Yan, Y-C., Olander, J., Connolly, D., and Connolly, D. (1990) J. Exp. Med. 172:1535–1545.
7. Kao, J., Ryan, J., Brett., J., Chen, J., Shen, H., Fan, Y-G., Godman, G., Familletti, P., Wang, F., Pan, Y-C., Stern, D. and Clauss, M. (1992) J. Biol. Chem. 267:20239–20247.
8. Keck, P., Hauser, S., Krivi, G., Sanzo, K., Warren, T., Feder, J., and Connolly, D. (1989) Science 246, 1309–1312.
9. Senger, D., Galli, S., Dvorak, A., Perruzzi, C., Harvey, V., and Dvorak, H. (1983) Science 219,983–985.
10. Connolly, D., Heuvelman, D., Nelson, R., Olander, J., Epley, B., Delfino, J., Siegel, N., Leimbruber, R., and Feder, J. (1989) J. Clin. Invest. 84:1470–1478.
11. Brock, T., Dvorak, H., and Senger, D. (1–991) Am. J. Pathol. 138, 213–221.
12. Leung, D., Cachianes, G., Kuang, W-J., Goeddel, D., and Ferrara, N. (1989) Science 246, 1306–1309.
13. Shen, H., Clauss, M., Ryan, J., Schmidt, A-M., Tijburg, P., Bordon, L., Connolly, D., Stern, D. and Kao, J. (1993) Blood 81, 2767–2773.
14. Fay, P., Kawai, Y., Wagner, D., Ginsburg, D., Bonthron, D., Ohlsson-Wilhelm, B., Chavin, S., Abraham, G., Handing, R., Orkin, S., Montgomery, R., and Marder, J. (1986) Science 232, 995–998.
15. Bonthron, D., Handin, R., Kaufman, R., Wasley, L., Orr, E., Mitsick, L., Ewenstein, B., Loscalzo, J., Ginsburg, D., and Orkin S. (1986) Nature 324,270–273.
16. Scott, J., and Montgomery, R. (1982) Blood 58, 1075–1080.
17. Wagner, D., and Bonfanti, R. (1991) Mayo Clin. Proc. 66,621–627.
18. Tijburg, P., Kao, J., Yan, S-D., van Mourik, J., and Stern, D. (1992) Circ. 86 (suppl I), #1627.
19. Clark-Lewis, I., Schumacker, C., Baggiolini, M., and Moser, B. (1991) J. Biol. Chem. 266, 23128–23134.
20. Herbert, C., Vitangcol, R., and Baker, J., (1991) J. Biol. Chem. 266, 18989–18994.
21. Moser, B., Dewald, B., Barella, L., Schumacker, C., Baggioini, M., and Clark-Lewis, I. (1993) J. Biol. Chem. 268, 7125–7128.
22. Barany, G., and Merrified, R., (1980) in *The Peptides.* Gross, E., and Meienhofer, J. Eds. Academic Press, NY. pp. 281–284.
23. Fraker, P., and Speck, J., (1978) Biophys. Res. Commun. 80, 849–857.
24. Boyum, A. (1968) Scand. J. Lab. Invest. 21 (Suppl. 97), 77–81.
25. Fluks, A. (1981) J. Immunol. Methods 41, 225–233.
26. Jaffe, E., Nachman, R., Becker, C., and Minick, R. (1973) J. Clin. Invest. 52, 2745–2756.
27. Thornton, S., Mueller, S., and Levine, E. (1983) Science 222, 623–625.
28. Shreeniwas, R., Koga, S., Karakurum, M., Pinsky, D., Kaiser, E., Brett, J., Wolitzky, C., Norton, C., Plocinski, J., Benjamin, W., Burns, D., Goldstein, A., and Stern, D. (1992) J. Clin. Invest. 90, 2333–2339.
29. Quinn, M., Parthasarathy, S., Fong, L., and Steinberg, D. (1987) PNAS(U.S.A.) 84, 2995–2998.
30. Harvath, L., Falk, W., and Leonard, E. (1980) J. Immunol. Meth. 37, 39–45.
31. Kondo, S., and Kisiel, W. (1987) Blood 70, 1947–1954.
32. Greenberg, S., DiVirgilio, F., Steinberg, T., and Silverstein, S. (1988) J. Biol. Chem. 263, 10337–10343.
33. DiVirgilio, F., Meyer, B., Greenberg, S., and Silverstein, S. (1988) J. Cell Biol. 106, 657–666.
34. DiVirgilio, F., Steinberg, T., and Silverstein, S. (1990) Cell Calcium 11, 57–62.
35. Menegazzi, R., Zabucchi, G., Knowles, A., Cramer, R., and Patriarca, P. (1992) J. Leuk. Biol. 52, 619–624.
36. Klotz, I., and Hunston, D. (1984) J. Biol. Chem. 258, 11442–11445.
37. Montesano, L., Cawley, D., and Herschman, H. (1982) Biochem. Biophys. Res. Commun. 109, 7–13.
38. Laemmli, U. (1970) Nature 227, 680–685.
39. Kloczewiak, M., Timmons, S., and Hawiger, J. (1987) Biochemistry 26, 6152–6156.
40. Kay, J., Porcelli, S., Tite, J., Barry, J., and Janeway, C. (1983) J. Exp. Med. 158, 836–856.
41. Granstein, R., Margolis, R., Mizel, S., and Sauder, D. (1986) J. Clin. Invest. 77, 1020–1027.
42. Matsushima, K., Morishita, K., Yoshimura, T., Lavu, S., Obayashi, Y., Lew, W., Appella, E., Kung, H., Leonard, E., and Oppenheim. (1988) J. Exp. Med. 167, 1883–1893.
43. Baggiolini, M., and Clark-Lewis, I. (1992) FEBS Lett. 307, 97–101.
44. Schiffman, E., Corcoran, B., and Wahl, S. (1975) PNAS (U.S.A.) 72, 1059–1062.
45. Ming, W., Bersani, L., and Mantovani, A. (1987) J. Immunol. 138, 1469–1474.
46. Durum, S., Schmidt, J., and Oppenheim, J. (1985) Annu. Rev. Immunol. 3, 263–287.
47. Pennica, D., Nedwin, G., Hayflick, J., Seeburg, P., Derynck, R., Palladino, M., Kohr, W., Aggarwal, B., and Goeddel, D. (1984) Nature 312, 724–729.

48. Oppenheim, J., Zachariae, C., Mukaida, N., and Matsushima, K. (1991) Annu. Rev. Immunol. 9, 617–648.

D. Treatment of Tumors

1. Vaage J. and Pepin K. G., Morphological Observations during Developing Concomitant Immunity against a C3H/He Mammary Tumor. Cancer Research 45, 659–66 February 1985.
2. Twentyman P. R. Brown J. M., Franko A. J., Scoles M. A., and Kallman R. F., A New Mouse Tumor Model System (RIF-1) for Comparison of End-Point Studies. JNCI, Vol 64(3), 595–604, March 1980.
3. Braunschweiger P. G., Kumar N., Constantinidis I., Wehrle J. P., Glickson J. D., Johnson C. S., and Furmanski P., Potentiation of Interleukin 1-alpha Mediated Antitumor Effects by Ketoconazole. Cancer Research 50, 4709–17, August 1990.

Second Series of Experiments

Characterization of a Novel Tumor-Derived Cytokine: Endothelial-Monocyte Activating Polypeptide II Endothelial-monocyte activating polypeptide II (EMAP II) was initially identified in the supernatant of murine methylcholanthr,ne A-induced fibrosarcomas (Meth A) by its capacity to activate host effector cells )Kao, J., Ryan, J., Brett, J., Chen, J., Shen, H., Fan, Y-G., Godman, G., Familletti, P., Wand, F., Pan, Y-C., Stern, D., and Clauss, M. (1992) J. Biol. Chem 267, 20239–20247). Based on the $NH_2$-terminal protein sequence, a full-length cDNA has been cloned which indicates that the precursor of EMAP II is a unique, leaderless, single polypeptide chain with predicted molecular mass ≈34 kDa and that the mature form released by Meth A cells corresponds to ≈20 kDa. Purified recombinant mature EMAP II (EMAP II, ≈20 kDa form) activated endothelial cells with resulting elevation of cytosolic free calcium concentration, release of von Willebrand factor, induction of tissue factor, and expression of the adhesion molecules E-selectin and P-selectin. Neutrophils exposed to EMAP II demonstrated elevated cytosolic free calcium concentration, peroxidase generation, and chemotaxis. EMAP II also activated mononuclear phagocytes elevating cytosolic free calcium concentration, inducing tumor necrosis factor-α (TNF) and tissue factor, and stimulating chemotaxis. Systemic infusion of EMAP II into C3H/HeJ or Balb/c mice was associated with systemic toxicity, pulmonary congestion, and the appearance of TNF, interleukin-1 and -6 in the plasma. A single intra-tumor injection of EMAP II into Meth A sarcomas induced acute thrombohemorrhage and partial tumor regression. Local injection of EMAP II into a tumor resistant to the effects of TNF, murine mammary carcinoma, rendered it sensitive to subsequently administered TNF, which resulted in acute thrombohemorrhage and partial regression. These data suggest that recombinant EMAP II, a tumor-derived cytokine, has properties of a proinflammatory mediator with the capacity to prime the tumor vasculature for a locally destructive process.

Tumor vasculature represents a critical link between the host and neoplasm. It serves as a conduit for the delivery of nutrients necessary to sustain the tumor and promote its growth and spread, but it also serves as a portal for the entry of host effector cells and cytotoxic agents (1,2). The vasculature of certain tumors has properties which distinguish it from the normal vasculature; these include an exaggerated response to the systemic infusion of flavone acetic acid or cytokines, such as interleukin 1 (IL-1)[1] and tumor necrosis factor-α (TNF), increased permeability, and infiltration by inflammatory/immune effector cell (3–10). To understand mechanisms responsible for vascular dysfunction in the tumor bed, mediators released by the immunogenic murine methylcholanthrene A-induced fibrosarcoma (Meth A) have been characterized based on their capacity to modulate properties of endothelial cells (ECs), mononuclear phagocytes (MPs), and polymorphonuclear leukocytes (PMNs), cells which have important roles in tumor vasculature (11–13).

Meth A tumors provide a suitable model for assessing the effects of tumor-derived factors which modulate the host response (4, 14). The vasculature of these tumors is distinguished from that of normal tissues by the properties described above. The response of Meth A tumors to systematically administered cytokines has been well characterized, beginning with hemorrhage/thrombosis and increased permeability of tumor vessels, and associated with diminished blood flow as well as subsequent influx of hose effector cells (4). Although Meth A cells produce multiple mediators capable of interacting with inflammatory/immune effector cells, three polypeptides which are likely to contribute to host-tumor interactions have been characterized in more detail (11–13). One of these proved to be identical to vascular permeability factor/vascular endothelial growth factor (VPF/VEGF), which has effects on PMNs and MPs, in addition to its well-known ability to perturb EC functions (12, 15). The other two Meth A-derived polypeptide mediators were termed endothelial-monocyte activating polypeptides (EMAPs) I and II, base on their ability to modulate functions of ECs and MPs (11, 13). Molecular characterization of EMAPs is a first step in delineating their possible contributions to the biology of Meth A tumors.

Here is reported the cloning of the cDNA for EMAP II, expression of recombinant EMAP II, and experiments concerning its effects on ECs, PMNs, and MPs in vitro as well as its effects following injection into normal and tumor-bearing mice. The results are consistent with a model in which local production of EMAP II by certain tumors sensitizes the vasculature to subsequent provocative challenge with a systemically administered cytokine, such as TNF, thereby promoting a destructive process in the tumor bed.

Mareials and Methods

Isolation of Meth A cell RNA—Meth A cells (generously provided by Dr. L. Old, Cancer Research Institute, New York, N.Y.; 14) were grown in RPMI 1640 containing fetal bovine serum (10%; Gemini, Calabsssas, Calif.) to ≈90% confluence. Cells (≈$10^8$) were harvested with trypsin, resuspended in fetal bovine serum (10%), and poly(A)+RNA isolated directly as described (16). Briefly, cells were lysed in SDS-containing buffer, and proteins were digested with proteinase K (Boehringer Mannheim) for 3 h at 55° C. The poly(A)+RNA was further purified using oligo)dT)-cellulose bound to magnetic beads (Promega, Madison, Wis.).

Isolation of Murine CDNA Clones—Meth A mRNA (1 μg) was denatured with MeHgOH and reverse transcribed with avian myeloblastosis virus reverse transcriptase (Invitrogen, San Diego, Calif.) using oligo(dT)$_{17}$ as a primer. The first strand cDNA obtained was used as template for the polymerase chain reaction (PCR) using degenerated primers based on the $NH_2$-terminal protein sequence obtained for EMSP II (13). The sense primer was 5'-GGCGAATTCAARCCNATHGAYGC-3'(SEQ ID NO. 32) and the antisense primer was 5'-GGCGAATTCYTTNGCNGTNACDAT-3'(SEQ ID NO. 33) with EcoRI sites near their 5'-ends to facilitate cloning of the PCR products. The thermocycling parameters consisted of three cycles of 95° C. for 30 s, 30 s at 37° C., and 1 min at 72° C. This was followed by 30 cycles of 30 s at 95° C., 30 s at 55° C., and 1 min at 72° C. Analysis of the amplified products on an acrylamide gel showed a DNA fragment of the expected size of 77 bp. The PCR products were then digested with EcoRI, run on an acrylamide gel, the appropriate band excised and eluted, and the DNA fragment cloned into the plasmid vector pUC219. Plasmids containing EcoRI inserts were sequenced by the Sanger dideoxynucleotide method using Sequenase (U.S. Biochemical Corp., Cleveland, Ohio). The deduced amino acid sequence was found to match exactly that obtained by protein sequencing (13). A 57-mer nucleotide probe was designed based on the consensus nucleotide sequence obtained from sequencing several clones (5'-AAGCCCATTGATGCCTCCCGGCT-GGACCTGCGGATTGGCTGCATTGTGACAGCC-AAG-3'). This probe was end-labeled with $^{32}$P-dCTP using polynucleotide kinase and employed to screen a Meth A cDNA library in the λvector HEBO5 (17). Hybridization was performed in formamide (20%), SSC (5×), sodium phosphate (50 mM, pH 6.5), denatured salmon sperm DNA (40 ug/ml), SDS (0.1%), and Denhardt's solution (5×) at 42° C. One positive plaque was identified which conta;ined a 700-bp insert. A second library, in λgt 10, was constructed from cDNA primed with a specific primer, 5'-ATTTTGCATCTGTTCTAG-3', complementary to sequence near the 5'-end of the original clone. This library was screened with the same oligonucleotide probe described above under the same conditions. Eight positive plaques were obtained from ≈$10^5$ screened. These were sub-cloned in pUC219 and sequenced in both directions. When this sequence was overlapped with the original clone, a 1086-bp sequence was obtained. A full-length EMAP II cDNA was constructed in the Epstein-Barr virus-based vector, pHEBO23 (17), by joining the two fragments at the XbaI restriction site present in both pieces.

Cloning of the Human EMAP II cDNA—Low stringency Northern analysis of human U937 mRNA using a murine probe suggested the EMAP II transcript was expressed by this cell line (data not shown). Thus, an oligo(dT)-primed U937 library in λgt 10 (kindly provided by Brian Bennett, Genetech, So. San Francisco, Calif.) was screened. Plaques (≈$10^6$) were screened using a probe consisting of the first 310 nucleotides at the 5'-end of the murine EMAP II clone. This ClaI (in the vector polylinker) to ScaI (500 bp) fragment was nick-translated and hybridized in formamide (20%), sodium phosphate (50 mM, pH 6.5), SSC (5×), Denhardt's solution (5×), SDS (0.1%), and denatured salmon sperm DNA (40 ug/ml) at 42° C. About 20 positives were obtained, and 10 of these were purified. The three which contained the longest inserts appeared to have identical 1100-bp EcoRI inserts. These inserts were subcloned in pUC219 and sequenced.

Northern Analysis of Meth A Cell mRNA for EMAP II Expression-Poly(A)+RNA from Meth A sarcoma cells was denatured and subjected to electrophoresis on an agarose gel (1.2%) in MOPS-formaldehyde (18). The RNA was transferred to nitrocellulose (Schleicher and Schuell) and prehybridized in formamide (50%), sodium phosphate (50 mM, pH 6.5), SSC (5×), DeDenhardt's solution (5×), SDS (0.1%), and denatured salmon sperm DNA (40 ug/ml) at 42° C. A 279-bp DNA fragment was isolated from the murine EMAP II clone following XbaI and SacI digestion corresponding to nucleotides 652–930. This was nick-translated with 32P-dCTP and hybridized to the blot overnight. Washing was performed at a final stringency of SSC (0.2×)/SDS (0.1%) at 55° C. The blot was then exposed overnight for autoradiography.

*E. coli* Expression of Murine EMAP II—In order to confirm the biological activity of the protein encoded by the cloned DNA sequence, the region corresponding to the predicted mature protein, based on the $NH_2$-terminal sequence obtained from purified EMAP II, was expressed. This was accomplished using a fragment of the murine clone extending from the BstBI site (nucleotide 529) to the 3'-untranslated region and synthetic DNA encoding the $NH_2$-terminal end, KPIDA-SRLEL (5'-TATGAAACCAA-TCGATGCATCTCGTCTGGATCTT-3' and 5'-CGAAGA-TCCAGACGAGATGCATCGATTGGTTTCA-3'). This sequence, which differs from the $NH_2$-terminal region obtained by micro-sequencing because the $NH_2$-terminal residue, serine, was inadvertently omitted when designing the synthetic DNA, was cloned into the NdeI site, containing the ATG initiation codon, and the BamHI site of the vector pET-3a in which cDNA expression is driven by the T7 promoter. The protein was then expressed in the host HMS174(DE3) which contains the T7 RNA polymerase gene under control of the lacUV5 promoter. Following growth to log phase, the T7 polymerase was induced with isopropyl-1-thio-β-D-galactopyrnoside (0.4 mM), and the cells were harvested by centrifugation 3 h later.

The pellet was dissolved in Tris (20 mM, pH 7.4)/EDTA (2 mM) /benzamidine (1 mm)/sodium azide (0.02%)/octyl-B-glucoside (0.1%), agitated at 4° C., and sonicated. The supernatant was centrifuged at 20,000 revolutions/min for 40 min (4° C.), and dialyzed versus Tris (20 mM, pH 7.4)/octyl-B-glucoside (0.1%). After dialysis, the sample (30–40 mg) was applied to FPLC Mono Q (HR 5/5), and the column was eluted with an ascending salt gradient (0–1.0 M). Fractions were assayed for their ability to induce EC tissue factor (see below), and active material was pooled, concentrated (Centricon 3, Beverly, Mass.), and subjected to preparative nonreduced SDS-PAGE (12.%; 19). Gels were then sliced into 1-mm portions and eluted during incubation in sodium acetate (0.5 M, pH 8.3, 0.5 ml)/octyl-B-glucoside (0.1%) overnight at 4° C. samples were tested for their ability to induce EC tissue factor (see below), subjected to analytical SDS-PAGE (12.5%) and silver staining, and tested for their lipopolysaccharide (LPS) content (Endospecy, Seikagaku Corp., Tokyo, Japan). According to the latter assay, LPS contamination of the purified material was, 10 pg/ml. In control experiments, *Escherichia coli* pellets from bacteria transformed with vector alone (e.e. no EMAP II) were subjected to the same purification steps. In certain experiment, heat-treated EMAP II was prepared by boiling the polypeptide for 15 min. The latter material demonstrated none of the activities described below.

Characterization of purified recombinant EMAP II included SDS-PAGE, with visualization of protein by silver staining, and immunoblotting with an antibody generated to a synthetic peptide comprising residues 1–14 from mature EMAP II (residues 145–158 from the precursor form) (13). Sites of binding of primary antibody were visualized with peroxidase-conjugated goat anti-rabbit IgG (Sigma).

Preparation of ECs, MPs, and PMNs—Human umbilical vein ECs were prepared by the method of Jaffe et al. (20) as modified by Thornton et al. (21), and characterized as described previously (13). Human peripheral blood monocytes were isolated from the blood of normal healthy volunteers (22). Blood was centrifuged on Histopaque 1077 (Sigma), the mononuclear fraction was obtained, washed twice in Hanks' balanced salt solution, resuspended in RPMI 1640 containing human serum (10%; Gemini, Calabassas Calif.), plated on tissue culture dishes (106 cells/ml), and incubated at 37° C. for 1–2 h. Nonadherent cells were removed by washing the plate three times with balanced salt solution, and adherent cells were harvested by incubation with calcium-magnesium-free buffer containing EDTA (2 mM) for 15 min at 37° C. followed by extensive washing. The adherent population, which is enriched for human mononuclear phagocytes (although there are also some additional cells) were termed MPs. Cytosolic [$Ca^{2+}$] and chemotaxis experiments employed freshly isolated MPs. For other experiments, MPs were allowed to differentiate in culture for 10–14 days is RPMI 1640 containing human serum (10%) and penicillin/streptomycin (100 units/ml-100 ug/ml). Human PMNs were prepared from heparinized blood by centrifugation over Histopaque 1077 and 1119 (Sigma).

Cell pellets containing red cells and PMSs were diluted 1:2 in normal saline, exposed to NaCl (0.2) for 20 s (to lyse erythrocytes), restored to isotonicity with sodium chloride (1.6%), and centrifuged (250×g) for 10 min (13, 23). Following two repetitions of this procedure, the cell population of 0.98% PMNs was resuspended in RPMI 1640 containing heat-inactivated human serum (3%).

In Vitro Assays of EC, MP, and PMN Functions-Cell-associated tissue factor was assayed by its functional activity, using purified coagulation proteins, and tissue factor mRNA was detected by PCR. Cells (ECs and MPS, ≈$10^4$ cells/assay in each case) were exposed to EMAP II alone or in the presence of other agents as indicated at 37° C. Cells were then treated with ammonium hydroxide (0.1 N), washed twice with HEPES (10 mM, pH 7.4), NaCl (137 mM), KCl (4 mM), flucose (10 mM), and were then incubated in the same buffer containing bovine serum albumin (0.5 mg/ml) and CaCl2 (3 mM) for 1 h at 37° C. in the presence of purified human Factors VIIa (1 nM) and X (200 nM) (13, 24). The reaction was stopped by the addition of Tris-HCl (50 mM, pH 7.9)/NaCl (175 mM) /EDTA (5 mM)/albumin (0.5 mg/ml), and the sample was assayed for Factor Xa activity using a chromogenic substrate assay at $OD_{405nm}$ (Spectrozyme Factor Xa, American Diagnostica, Inc., Greenwich, Conn.), as described (25). The concentration of Factor Xa was determined based on a standard curve generated with purified Factor Xa. Less than 10% of the available substrate was consumed during these reactions, and reaction rates were linear during the time interval of this reaction. Where indicated, monospecific, blocking rabbit ant-human tissue factor IgG (24) or nonimmune IgG was also included in the assay along with Factors VIIa and X. PCR analysis to detect tissue factor transcripts was performed on human mononuclear phagocytes and ECs as described previously (13). Controls included amplification of glyceraldehyde phosphate dehydrogenase (GAPDH) transcripts (13).

Ec expression of the leukocyte adherence molecule E-selectin was monitored by ELISA (R&D Systems, Cambridge, Mass.) on the surface of nonpermeabilized, fixed ECs, as described (26). In brief, ECs were exposed to medium alone, LPS or EMAP II for 4 h, cultures were then fixed in glutaraldehyde (0.05%), blocked with bovine serum albumin (3%), and incubated with mouse anti-human E-selectin IgG followed by peroxidase-conjugated goat anti-mouse IgG. Western blotting was performed on EC monolayers exposed to the above stimuli by dissolving the cells in lysis buffer (Tris, 10 mM; pH 7.5; Nonidet P-40, 1%; EDTA, 1 mM; phenylmethylsulfonyl fluoride, 1 mM; pepstatin, 1 μg/ml; aprotonin, 15 ug/ml), centrifuged (13,000×g for 10 min) to remove all debris, and the supernatant was diluted in SDS sample buffer and subjected to nonreduced SDS-PAGE (4–15% gradient gel). Immunoblotting was performed using the Blotto procedure (27). The primary antibody was murine monoclonal anti-human E-selectin IgG (50 ng/ml: Sigma). Cell surface expression of P-selectin was determined by assessing binding of $^{125}$I-murine monoclonal anti-human P-selectin IgG (Endogen, Boston Mass.: radiolabeled using Iodobeads; 28) to EC monolayers. In brief, ECs were incubated with either EMAP II or a-thrombin (2 units) for 1 h, foxed for 15 min in paraformaldehyde (1%; 29), and exposed to $^{125}$I-anti-P-selectin IgG (100 ng) for 2 h at 4° C. Cultures were then washed four times in balanced salt solution, and bound antibody was eluted by dissolving the cell monolayer with Triton X-100 (1%) in phosphate-buffered alsine. Nonspecific binding of $^{125}$I-anti-P-selectin antibody to EC monolayers was determined in the presence of a 1,000-fold excess of unlabeled anti-P-selectin antibody. Specific binding is the difference of total binding (in the presence of $^{125}$I-anti-P-selectin IgG alone) and nonspecific binding (in the presence of excess unlabeled anti-P-selectin IgG). Data in FIG. 7C are reported as a percent of the specific $^{125}$I-anti-P-selectin IgG binding observed following exposure of monolayers to thrombin (the positive control). EC release of vWF into culture supernatants was quantified by ELISA.

[$Ca^{2+}$], Measurements-Ionized calcium levels were measured in ECs grown on glass converslips. Endothelium was loaded with fura-2 by incubation for 30 min at room temperature in HEPES-buffered saline with fura-2 AM (5 UM) and pluronic acid (0.1%). Coverslips were mounted in a lucite chamber and placed in a Zeiss Axiovert 135 TV inverted microscope equipped with epifluorescence optics. The switching of excitation filters (350 and 380 nm) was controlled by a computer running Videoprobe software (ETM Systems). Eight video frames were averaged at each wavelength; ratio images were obtained at 1 Hz. [Ca2+] was derived from the ratios as described previously (30). $R_{min}$ and $R_{max}$ were derived from in vitro measurements using fura-2 free acid in a 20-um thick glass chamber (31).

For determination of [$Ca^{2+}$] in PMSs and MPs, cells (2×$10^7$ in each case) were incubated with fura-2AM (1 um) and pluronci detergent (0.02%) at room temperature, diluted 6-fold, and incubated for a further 30 min at room temperature to allow for complete hydrolysis of the dye. Cells were then resuspended in HEPES-buffered saline at 5×$10^5$ cells/ml (32). For MPs, sulfinpyrazone (0.5 mM) was included at all steps to minimize both dye sequestration into intracellular organelles and dye efflux (33). Fluorescence of fura-2 was monitored at 37° C. in a thermostatically controlled cuvette installed in a Perkin Elmer model 650-40 fluorescence spectrophotometer. Calibration of [$Ca^{2+}$] was performed as described (34).

Migration of PMNs and MPs—Migration was studied using cells ($10^4$ and $10^3$ cells/well form PMNs and MPs, respectively) resuspended in RPMI 1640 with fetal calf serum (1%) added to the upper wells of a microchemotaxis chamber (Neuro Probe, Bethesda, Md.) containing Nucleopore polycarbonate membranes (5 um, Nucleopor, Pleasanton, Calif.), as described (13, 22, 35). The stimulus was placed in the upper or lower chamber, as indicated, and the cells were allowed to migrate for 3 h (for MPs) or 45 min (for PMNs) at 37° C. Following removal of nonmigrating cells, membranes were fixed in methanol, and migrating cells were visualized with Wright's stain. Assays were performed in quadruplicate, and cells were counted in eight high-power fields in each case (mean±S.E. is shown in the figures).

Release of Peroxidase Generating Activity from PMNs (myeloperoxidase)—Release was determined by a previously described assay (36) which monitors oxidation of the substrate 3,3',5,5'-tetramethylbenzidine (TMB; Sigma). PMNs were assayed at a concentration of $3 \times 10^6$ cells/ml for 60 min at 37° C. with RPMI 1640 containing fetal calf serum (1%) alone or in the presence of EMAP II or phorbol ester (phorbol 12-myristate 13-acetate; Sigma). Peroxidase activity was determined spectrophotometrically at 620 =m and is reported as percent total peroxidase activity (100% being defined as the activity observed with that number of PMNs following 60 min of exposure to phorbol ester, 10 UM). A standard curve was generated by assaying peroxidase activity from different numbers of PMNs treated with phorbol ester (10 UM). A modification of this method (37) was used to determine myeloperoxidase activity in lung tissue from mice infused with EMAP II as an index of pulmonary leukostasis (see below).

TNF Production by Human Macrophages—Production in RPMI containing heat-treated human serum (1%) was studied by incubating cultures ($10^5$ cells/well) with EMAP II for 6 h and assaying aliquots of culture supernatant using an ELISA for TNF antigen. PCR analysis for human TNF$\alpha$ transcripts was also performed on cultured macrohpages exposed to EMAP II by extracting total RNA using the acid-guanidinium thiocyanate procedure (Stratagene Inc., Torrey Pines, Calif.). Random hexanucleotide-primed first strand cDNA was prepared and served as template for PCR analysis. TNF primers were those described previously (38). cDNA was amplified by PCR for 30 cycles (with TNF primers) and 20 cycles (with GAPDH primers), each cycle consisting of incubations at 94° C. for 1 min, 50° C. for 2 min, and 72° C. for 2 min. Products were analyzed by agarose gel electrophoresis (1%) and visualized by ethidium bromide staining under ultraviolet light.

IL-8 production by human MPs in RPMI 1640 containing heat-treated human serum (1%) was studied by exposing cultures (105 cells/well) to EMAP II for 8 h and assaying aliquots of culture supernatant in an ELISA for human IL-8 as reported (39). EMAP II-induced changes in IL-8 transcripts were studied by PCR, as described above. IL-8 primers were those described by Carre et al. (40) and GAPDH primers used were as above. Conditions for PCR consisted of incubations at 95° C. for 2 min for 1 cycle, 1 min at 95° C. followed by 1 min at 60° C. for 35 cycles, and 7 min at 60° C. for 1 cycle for IL-8 and GAPDH.

EMAP II Infusion Studies—Infusion studies were performed with EMAP II (LPS content <10 pg/ml), heat-treated (15 min boiling) EMAP II, or saline alone by injecting the material in a single intravenous bolus into the tail vein of C3H/HeJ or Balb/c mice (Jackson Laboratories, Bar Harbor, Me.). Mice were monitored for general evidence of distress over 24 h. Lung tissue was harvested from animals 4 h post-treatment and was fixed overnight with formalin (10%) in phosphate-buffered saline, dehydrated, embedded in paraffin, and stained with hematoxylin/eosin by standard procedures (41). Other samples of lung tissue were flushed with saline to remove residual blood, and then lungs were removed from the chest cavity and homogenized in phosphate buffer (50 mM; pH 6.0) containing hexadecyl trimethyl ammonium bromide (0.5%). This extraction procedure was repeated three times, as described previously (37, 42), the extracts were pooled, and myeloperoxidase activity was assayed using standard chromogenic spectrophotometric techniques. In other experiments, animals were sacrificed at specified time points, blood was obtained, and the levels of murine IL-1$\alpha$, IL-6, and TNF$\alpha$ were determined by ELISA using commercially available kits.

Local Injection of EMAP II into Meth A Sarcomas and Murine Mammary Carcinomas—Meth A cells were used to product tumors in C3H/He mice (Charles River Laboratories, Wilmington, Mass.) by intradermal injection of $2 \times 10^5$ cells into the dorsal skin of each animal. Seven days later, when tumors reached ≈0.5-cm diameter, tumors were directly injected using a 30-gauge needle with vehicle solution)phosphate-buffered saline with bovine serum albumin, 0.1%), TNF (5 ug in the vehicle), heat-treated TNF (5 ug), EMAP II (10 ug in the vehicle), or heat-treated EMAP II (10 ug). Purified, recombinant human TNF$\alpha$ was generously provided by Knoll Pharmaceuticals (Whippany, N.J.). Six hours after the injection, animals were sacrificed, and tumors were excised and scored for the presence or absence of gross hemorrhage. Tissue samples for pathlogic analysis were fixed in buffered formalin (10%) and processed as above. Where indicated, tumor volume was calculated from caliper measurements of length, width, and height, according to the formula for a spherical segment, V-$\pi$h $(h^2+3a^2)/6$, where h=height of the segment, a=radius of the base of the segment, and V=volume (43).

Mouse mammary carcinomas derived from the MC2 cell line (generously provided by Dr. Jan Vaage, Rosewell Park Cancer Institute, Buffalo, N.Y.) (44) were raised by intradermal injection of 106 tumor cells into the dorsal skin of female C3H/He mice. Six days later, when tumors had reached ≈0.6 in diameter, each mouse received an intratumor injection of EMAP II (10 ug in vehicle), heat-treated EMAP II (10 ug), or vehicle alone (same volume as other injections), followed 12–18 h later by a single tail vein injection of either TNF (5 ug), heat-treated TNF (5 ug), EMAP II (20 ug), or heat-treated EMAP II (20 ug). Tumors were either excised 6 h following the intravenous injection and examined for the presence of hemorrhage, or else followed for up to 7 days for assessment of tumor volume (as above) over time. In one set of experiments, on the third post-treatment day, groups of three tumors were pooled and assayed for clonogenic cell survival by a modification of the methods of Twentyman et al. (45) and Braunschweiger et al. (46). Tumors were aseptically excised and weighed, then finely minced, and digested by gently agitation for 90 min at room temperature in Hanks' balanced salt solution containing trypsin (0.75 mg/ml), collagenase (0.75 mg/ml), and DNase (0.05 mg/ml) (all from Sigma). The resulting cell suspension was passed through a sterile wire mesh filter (Collector tissue sieve, Bellco Glass, Inc., Vineland, N.J.), washed twice, counted, and plated out at serial dilutions in RPMI 1640 containing fetal calf serum (10%), penicillin (150 units/ml), and streptomycin (150 ug/ml). After 4 days, the number of dividing colonies (each reflecting an initially clonogenic cell) derived from treated and control tumors were counted by a blinded observer. The proportion of clonogenic cells/gram of tumor, relative to control, was taken as the surviving fraction. All experiments involving tumor growth were performed with age- and sex-matched controls.

Results cDNA Cloning of EMAP II

Figure 11:
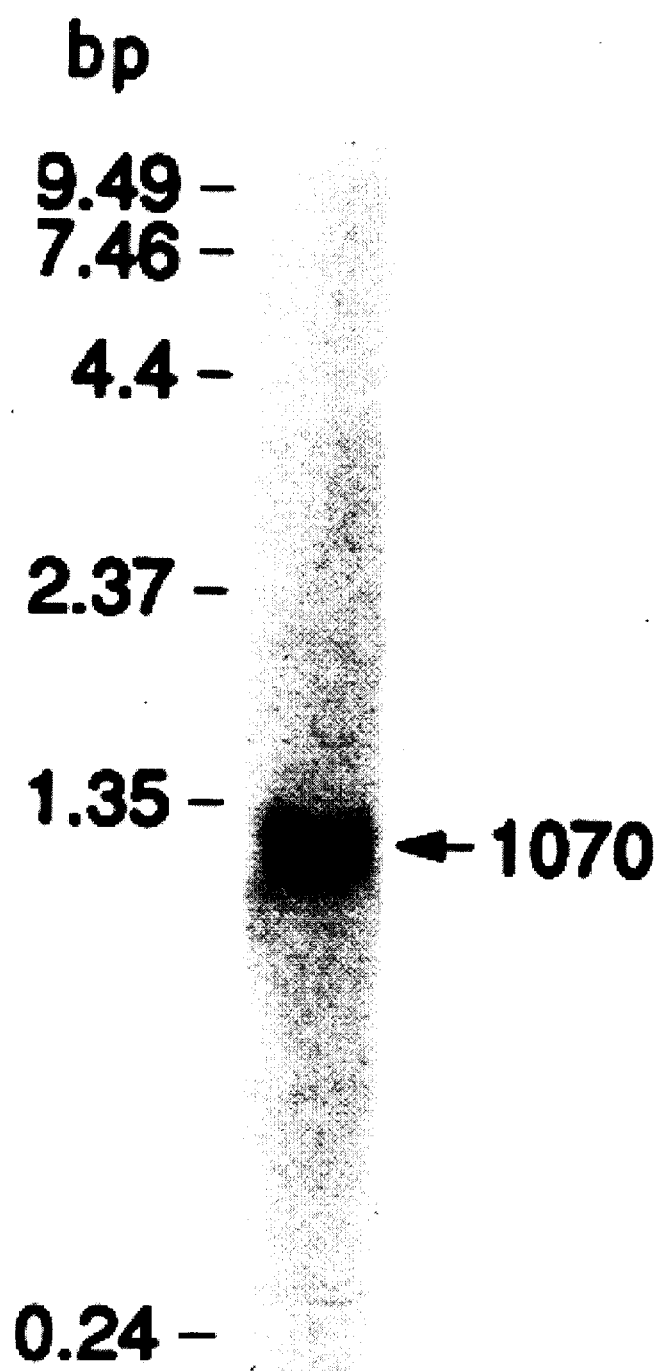

Purification of EMAP II from conditioned medium of murine Meth A sarcoma cells yielded a ≈22-kDa protein from which a unique amino-terminal sequence was obtained (13). Degenerate oligonucleotide primers were designed to generate a 77-bp fragment encoding a portion of the NH2-terminal sequence by PCR. The sequence obtained was then used as the bases for design of a 57-base oligonucleotide probe for screening a Meth A oligo(dT)-primed cDNA library. One clone, 680 bp, was isolated and represented a partial cDNA sequence with an open reading frame at the 5'-end. A second Meth A cDNA library was constructed using a specific primer based on the first sequence obtained, and the same 57-base probe was used to identify eight clones. Three of these appeared to have identical inserts of 660 bp based on restriction analysis, and the sequence obtained from these clones was overlapped with that of the original clone to produce a contiguous sequence of 1086 bp (FIGS. 4-1-4-2). Northern blot analysis of RNA from Meth A cells using a 275-bp XbaI to SacI fragment as a probe demonstrated a single transcript of ≈1070 bp suggesting the cDNA clone was full-length (FIG. 11). Analysis of this sequence revealed an open reading frame containing residues encoding the NH2-terminal sequence with a termination codon at nucleotide 894 followed by a polyadenylatio signal (AATAAA). There are three ATG codons in this reading frame in the first 200 nucleotides of the cDNA with no upstream stop codons. However, only the second, at position 64, meets the criteria of Kozak (47) for initiation of translation. Thus, using codon 64 as the start codon, the open reading frame would encode a protein of 310 amino acids with a predicted molecular mass of ≈34 kDa. A fragment of the murine cDNA was used as a probe to isolate a full-length human cDNA clone for EMAP II from a λgt 11 U937 monocyte library (FIG. 13). Compared with murine EMAP II, the human cDNA was 86% identical, and the deduced sequence contained an additional 2 amino acids. The ATG designated as the start codon and the upstream ATG are both conserved in the human cDNA.

Since the $NH_2$-terminal sequence obtained from purified EMAP II is encoded by an internal sequence of the EMAP II clone, it was predicted that mature EMAP II results from processing of a larger polypeptide. The cDNA corresponding to the $NH_2$-terminal, processed portion of the sequence encodes 165 amino acids which would result in a polypeptide of ≈18 kDa, in close agreement with the ≈22 kDa observed for EMAP II purified from Meth A sarcoma cells. Although EMAP II is apparently secreted by Meth A sarcoma cells (13), hydropathy analysis of the predicted murine primary amino acid sequence lacked evidence of a hydrophobic signal peptide (FIG. 12). Of note is that both the predicted size of the protein before cleavage, as well as the cleavage site in this protein, are reminiscent of another secreted cytokine which also lacks a classic signal peptide, IL-1β. The mRNA for IL-1β encodes a 31-kDa precursor to the mature 17 kDa form (48). The pre-IL-1β is cell associated, unable to bind to IL-1 receptors, and is biologically inactive (49). Proteolytic processing releases a 17-kDa secreted, active IL-1β (50). An Asp in the P-1 position of IL-1β is necessary for cleavage by the cysteine protease IL-1β-converting enzyme to yield the active 17-kDa IL-1β4 (51, 52). This Asp, as well as other residues of the prohormone processing site, are evolutionarily conserved in all known IL-1 μ sequences (53). In EMAP II, an Asp is present in the P-1 position in both the murine and human forms (FIG. 13, arrow). Thus, a cysteine protease similar or identical to IL-1β-converting enzyme might be responsible for producing mature EMAP II from its pro-form. Supporting the idea that the mature form is the biologically active protein, sequence conservation is 95% between the murine and human region of the mature polypeptide but drops to 74% in the putative pro-region.

The primary amino acid sequence of EMAP II showed little homology to any other proteins in the data banks. Nevertheless, a limited resemblance existed between residues in the NH2-terminal portion of mature EMAP II and several other cytokines, notably IL-8 (54, 55) and IL-1β (48), as well as von Willebrand antigen II, a product released by activated platelets and endothelial cells (56–60) (FIG. 13). All of these molecules share chemoattractant properties toward neutrophils and/or monocytes (61–63). In vitro mutagenesis of IL-8 demonstrated that changing residues in this area, E31, L32, R33, or I37, to alanine results in a molecule incapable of mobilizing calcium in neutrophils and having reduced ability to compete with native IL-8 for binding to neutrophil IL-8 receptors (64).

Purification of Murine EMAP II from *E. coli*

*E. coli* transformed with the portion of the EMAP II cDNA corresponding to mature EMAP II were pelleted by centrifugation, sonicated in the presence of Tris-buffered saline, and the supernatants chromatographed on FPLC Mono Q (FIG. 14A). The peak containing EMAP II activity was identified based on induction of tissue factor activity in ECs. In contrast, little protein eluted at a similar salt concentration from material obtained from *E. coli* transformed with vector alone, and this small peak had no significant tissue factor inducing activity when applied to ECs (FIG. 14b). Active fractions eluted from the Mono Q column (FIG. 14A) were pooled, concentrated, and subjected to nonreduced SDS-PAGE (FIG. 6A, lane I). Coomassie staining revealed a complex pattern of bands, although elution of protein from an identical lane of the gel demonstrated that only material with molecular mass ≈18 kDa had the capacity to induce tissue factor in ECs (FIG. 15A, right panel). This material was re-run on SDS-PAGE, and a single band visualized by silver staining was observed under both reduced and non-reduced conditions (FIG. 15B, lanes II and III, respectively), the latter having the capacity to induce EC tissue factor (FIG. 6B, far right panel). Immunoblotting of gel-eluted, purified EMAP II with an antibody raised to a peptide comprising residues 145–158 of EMAP II (corresponding to residues 1–14 of the mature form isolated from media conditioned by Meth A cells; 13) visualized the ≈18 kDa band purified from *E. coli* transfected with the EMAP II cDNA (FIG. 15C), whereas no band was observed when the control vector was used (data not shown).

Effects of EMAP II on ECs, MPs, and PMNs

In view of the production of EMAP II by Meth A tumors, whose vasculature displays distinct thrombogenic properties and which is infiltrated by hose effector cells (4), the ability of EMAP II to activate ECs, MPs, and PMNs was tested as the means by which it could contribute to producing the pathologic effects observed in vivo.

Endothelial Cells—Exposure of ECs to EMAP II induced a rise in $[Ca^{2+}]$ (FIG. 16), due mainly to redistribution of $[Ca^{2+}]$, from intracellular stores since a similar increase was seen when the cells were incubated in $[Ca^{2+}]$-free medium containing EGTA (5 mM; data not shown). Rises in EC cytosolic calcium are more typically identified with mediators such as histamine and thrombin (65, 66), rather than cytokine-like molecules such as EMAP II. In parallel with the effects of the latter mediators, elevated EC cytosolic calcium in response to EMAP II was accompanied by (i) enhanced release of vWF antigen into the supernatant of EC cultures (FIG. 16B), and (ii) increased cell surface expression of P-selectin, based on enhanced binding of $^{125}I$-monoclonal anti-P-selectin IgG (FIG. 16C). EMAP II-induced expression of P-selectin on the EC surface and release of vWF were comparable to a maximal stimulus, thrombin (29). Heat-treated EMAP II did not affect either vWF release or P-selectin expression on the cell surface (nor did it elevate Ec cytosolic calcium), and binding of nonimmune murine IgG to ECs was not changed by exposure to EMAP II (data not shown). These observations suggested that EMAP II could rapidly activate ECs in a manner promoting leukocyte adherence, i.e. by cell surface expression of P-selectin. Translocation of P-selectin and release of vWF is likely due to exocytosis of EC Weibel-Palade bodies (57) due to EMAP II-induced rise in cytosolic calcium.

EMAP II also modulated EC functions by causing the expression of gene products not normally present in quiescent ECs. Analogous to previous results with EMAP II purified from Meth A cells (13), recombinant EMAP II induced tissue factor activity in ECs in a dose-dependent manner, with half-maximal effect at 26 2–5 PM (FIG. 8A), and in a time-dependent manner (FIG. 17B). Heat-treated EMAP II was inactive. The necessity for de novo biosynthesis in EMAP II-induced expression of EC tissue factor was indicated by the inhibitory effect of actinomycin D (FIG. 17A). Consistent with the latter observation, EMAP II increased tissue factor transcripts (FIG. 17C, tissue factor, TF), whereas levels of transcripts for GAPDH remained unchanged (FIG. 17C. GAPDH).

Other stimuli which induce tissue factor, such as IL-1, TNF, and LPS, also result in enhanced expression of the leukocyte adherence molecule E-selectin (67). A cell surface ELISA for E-selectin demonstrated that ECs exposed to EMAP II expressed E-selectin antigen, comparable to levels observed following LPS stimulation, in contrast to undetectable levels in untreated controls (FIG. 17D). The presence of E-selectin antigen was confirmed by Western blotting of ECs exposed to EMAP II, where a single major band was observed (FIG. 17E, EMAP II) comigrating with that induced after exposing ECs to LPS (FIG. 17E, LPS). Immunoblots of extracts from untreated control cultures showed no immunoreactive band with anti-E-selectin IgG (FIG. 17E, control). EMAP II-mediated induction of E-selectin was not due to possible contaminating LbPS as (i) the EMAP II preparations used had <10 pg/ml LfPS (this amount of LiPS is inefective for E-selectin induction in ECs); and (ii) heat treatment of EMAP II abrogated its induction of E-selectin (these conditions have no effect on LPS; data not shown). The results of these studies indicate two overlapping mechanisms through which EMAP II potentially modulates EC adhesivity for PMNs: rapid translocation of P-selectin to the cell surface and subsequent induction of E-selectin.

Leukocytes (PMNs)—Because EMAP II could potentially increase adhesivity of PMNs for ECs by P-selectin and E-selectin-mediated mechanisms, it was important to determine whether EMAP II would also directly modulate properties of leukocytes. EMAP II elevated [$Ca^{2+}$], in ECs, and it did so in PMNs also (FIG. 9A). The average [$Ca^{2+}$], observed in PMNs was 130±7.9 nM; addition of EMAP II resulted in a peak increase in [$Ca^{2+}$], of 406±113 nM (mean±S.E.) (FIG. 18A). This increase in [$Ca^{2+}$], was due mainly to release from intracellular stores since it occurred in buffer without added $Ca^{2+}$ which had been supplemented with 1 mM EGTA (data not shown). A smaller, more sustained increase in [$Ca^{2+}$], which occurred after the peak of intracellular calcium, was due to influx of $Ca^{2+}$ across the plasma membrane (FIG. 18A), since it was seen only in cells incubated in the presence of 1 mM extracellular $Ca^{2+}$ (data not shown). Consistent with the capacity of EMAP II to activate PMNs, EMAP II induced concentration-dependent increase in myeloperoxidase activity, as measured in the peroxidase generation assay. This occurred in a dose-dependent fashion (FIG. 18B; EMAP II, bars 4–6) and was comparable to peroxidase generation by phorbolester (FIG. 18B; PMA, bars 1–3). Heat-treated EMAP II had the same effect on myeloperoxidase release as did medium alone (FIG. 18B; heat treatment (H. T.) and medium, bars 7 and 8, respectively).

Having previously observed that small amounts of EMAP II purified from supernatants of Meth A cells could induce cell migration (13), confirmation of these results was sought with recombinant material. Incubation of PMNs with recombinant EMAP II induced migration in chemotaxis chambers; the latter occurred in a dose-dependent manner in the picomolar range (FIG. 18C, 1–100 pM). Heat-treated EMAP II or medium alone were without effect (FIG. 18C; heat-treated and medium, respectively). At 100 pM, EMAP II induced PMN migration comparable to that observed with fMLP ($10^{-6}$M; FIG. 18C, 0/fMLP); this migration of PMN induced by EMAP II was true chemotaxis, as addition of mediator to the upper compartment of the chemotaxis chamber, in amount sufficient to destroy the concentration gradient, prevented directed cell movement (FIG. 18C; EMAP II, bars corresponding to 10/1, 10/10, 100/10).

Mononuclear Phagocytes—Because EMAP II had major effects on PMN function, it was inquired whether it might further perturb leukocyte function by promoting elaboration of mediators by MPs capable of activating PMNs, such as TNF and IL-8 (4, 68). Enriched human peripheral blood mononuclear phagocyte populations (termed MPs) exposed to EMAP II released TNFα antigen into the culture medium (FIG. 10A); TNF release was maximal within 6–8 h and was prevented by inclusion of cycloheximide (data not shown). In contrast, MPs exposed to heat-treated EMAP II (FIG. 19A, H.T. EMAP II) or medium alone (FIG. 19A; control) did not release TNFA. Generation of TNF by MPs exposed to EMAP II was accompanied by an elevation in the level of TNF transcripts (FIG. 19B, TNF) but not in GAPDH transcripts (FIG. 19B, GAPDH), as assessed by PCR.

As Il-8 is a tumor-associated cytokine which also activates PMNs (68), whether EMAP II could induce MPs to release IL-8 was studied. MPs exposed to EMAP II elaborated IL-8 antigen, though in lesser amounts than that observed following exposure to LPS (FIG. 19C), whereas heat-treated EMAP II (H.T. EMAP II) was without effect. Increased IL-8 antigen production was associated with elevated levels of IL-8 transcripts in MPs exposed to EMAP II (FIG. 19D, IL-8), where as GAPDH transcripts were unchanged (FIG. 19D, GAPDH).

Since Meth A-derived EMAP II Stimulates monocyte migration, and also shortens the clotting time of murine MPs (13), suggesting induction of procoagulant activity, the effect of recombinant EMAP II on these cellular properties was examined. Recombinant EMAP II induced directional migration of human MPs in a dose-dependent manner (FIG. 19E), over a similar range of concentrations to that observed for inducing PMN migration (FIG. 18C). Recombinant EMAP II also induced MP tissue factor activity in a time-dependent manner (FIG. 19F), which was accompanied by elevation of tissue factor transcripts (FIG. 10G, TF). Heat treatment of EMAP II abrogated its ability to induce tissue factor activity in MPs (FIG. 19F). Tissue factor induction in MPs was prevented by addition of actinomycin D, and tissue factor activity in the Factor VIIa-dependent Factor Xa formation assay was completely blocked by neutralizing anti-tissue factor IgG (data not shown). Similar to the data for ECs and PMNs, a rise in [$Ca^{2+}$], following exposure of MPs to EMAP II was observed (FIG. 19H), although the magnitude of the rise in [$Ca^{2+}$], was considerably less (39±6 nM; mean±S.E.; n=4) than that observed with ECs and PMNs.

Administration of EMAP II to Normal and Tumor-bearing Mice

Studies of isolated cell populations in vitro suggested that EMAP II would be phlogogenic in the intact animal, and indeed earlier studies in the mouse footpad showed that Meth A-derived EMAP II induced an inflammatory response (13). To extend these observations and gain further insights into the biology of EMAP II, tow models were selected: systemic infusion into normal mice and intratumor injection in mice bearing Meth A and murine mammary tumors.

Systemic Infusion of EAP II—C3H/Hej mice (LPS-resistant animals; 63) infused with recombinant EMAP II (10 ug) became lethargic within 2–4 h and decreased their food/water intake over the next 6–18 h. Body hair became ruffled, respirations were labored and rapid, but no fatalities were observed at this dose. Samples of plasma taken during the post-infusion period demonstrated the presence of IL-1a (with peak levels at 1–3 H), IL-6 (peaking at about 3 h), and TNFα (peaking about 4 h and decaying over the remaining 6 h) (FIG. 20A). Consistent with the potential of infused EMAP II to induce systemic effects, lung tissue from treated animals demonstrated arrest of circulating leukocytes/inflammatory cells in the pulmonary vasculature compared with untreated controls (FIG. 20, C and D). As an index of pulmonary leukostasis, sequential myeloperoxidase activity was determined in lung tissue from mice infused with EMAP II: myeloperoxidase activity rose within 0.5 H, remaining elevated for about 3 h (FIG. 20B). Animals receiving heat-inactivated EMAP II showed no similar increase in myeloperoxidase activity. When repeated in Balb/c mice, infusion of EMAP II produced a similar pattern of cytokine induction.

Intratumor Injection of EMAP II—The heterogeneity of the Meth A tumors, with areas of necrosis and infiltration by immune/inflammatory cells (4, 14), suggested the possibility that low concentrations of locally produced mediators, such as EMAP II, had perturbed the microenvironment. Thus it was determined whether administration of a single dose of EMAP II directly into the malignant lesion might result in changes including thrombohemorrhage and subsequent tumor regression. To test this hypothesis, C3H/He mice bearing Meth A tumors received a single intratumor injection of either EMAP II, heat-treated EMAP II, TNF, heat-treated TNF, or vehicle alone. Six h later, gross hemorrhage in the tumor bed was observed in 67% of animals receiving EMAP II, significantly more than that observed with heat-treated EMAP II (21%) or vehicle alone (13%) ($p<0.04$ by $x^2$ analysis) (FIG. 21, A). TNF, included as a positive control because it is known to cause hemorrhage in Meth A tumors (4), induced tumor hemorrhage in 93% of cases. Since the negative controls (heat-treated cytokines or vehicle alone) were delivered by intratumor injection of the same volume (0–1 ml) of solution, it may be concluded that the hemorrhagic response in the tumor bed following administration of EMAP II was a tissue response to EMAP II rather than an artifact of the injection. Microscopic examination of Meth A tumors injected with EMAP II demonstrated hemorrhage and infiltration with PMNs compared with controls (FIG. 21). The inflammatory infiltrate in the tumor bed is clearly shown in the higher power micrograph. A consequence of EMAP II injection into Meth A tumors was the subsequent accelerated decrease in tumor volume, compared with vehicle-treated controls, evident by the second day after treatment ($p<0.05$) (FIG. 21B).

These data suggested that endogenous production of EMAP II serves to shift the phenotype of tumor vascular endothelium to a surface promoting thrombohemorrhage and leukocyte adhesivity, enabling subsequent administration of systemic mediators to induce profound thrombohemorrhage and intense inflammation localized to the tumor bed. It was postulated that local EMAP II treatment might render TNF-insensitive tumors susceptible to the effects of TNF. A murine mammary carcinoma (MC2) was selected for these studies (44) since it does not undergo thrombohemorrhage or regression in response to $TNF^2$. Intratumor injection of either TNF or EMAP II alone did not induce visible hemorrhage in mammary tumors (FIG. 22A). In contrast, mammary tumors which received intratumor injections of EMAP II followed ≈15 h later by intravenous TNF showed increased intratumor hemorrhage 6 h later as compared with controls (i.e. animals that received substitutions of heat-inactived EMAP II, heat-inactivated TNF, or both, in place of the active cytokines; $p<0.005$) (FIG. 22B). Microscopic examination of tumors from animals which received EMAP II followed by TNF revealed an acute inflammatory infiltrate composed primarily of PMNs associated with tumor cell lysis within 6 h compared with controls (FIG. 22, C and D). Further evidence for diffuse change in tumor physiology following administration of EMAP II and TNF was the marked reduction in cell survival, based upon clonogenic survival assays performed on tumors harvested on the third post-treatment day (FIG. 13E). When animals receiving intratumor EMAP II followed by intravenous TNF or EMAP II were evaluated for longer times, it was evident that the initial acute response of the tumors to cytokine treatment was followed by a reduction in tumor volume over the next 7 days (FIG. 22F).

Discussion

A critical factor contributing to the properties of tumor neovasculature is the effect of mediators made by the tumor cells on elements of the vessel wall and circulating leukocytes and monocytes. These studies to characterize EMAP II have the goal of understanding how this novel polypeptide modulates these host-tumor interactions. Molecular cloning has shown that EMAP II is distinct from previously reported families of cytokines or growth factors, although it shares some features in common with IL-1 (48) including lack of a signal peptide and a 19–22 kDa mature form derived from a 34-kDa precursor. This suggests that similar mechanisms may be involved in processing several cytokines elicited in response to environmental stimuli. The only significant region of EMAP II with homology to previously described mediators (IL-8 and IL-1β) is a locus proximal to the NH2 terminus of mature EMAP II which is also similar to von Willebrand factor antigen II. A peptide comprising this portion of EMAP II has recently been shown to modulate properties of MPNs and MPs and to induce an acute inflammatory response when injected into the mouse footpad (25). Consistent with these data, the homologous peptide from von Willebrand antigen II effectively modulates these same properties in PMs and PMNs (62). Although $NH_2$-terminal peptides from EMAP II induce PMN and MP chemotaxis and elevate $[Ca^{2+}]$, in these cells, they do not stimulate MPs or ECs to express tissue factor (25). This suggests that these shorter peptides derived from EMAP II mimic only a portion of the biologic activities of the intact polypeptide.

The phlogogenic potential of EMAP II was suggested by in vitro studies demonstrating activation of ECs, MPs, and PMNs by several criteria, including direct effects on cellular properties and release of proinflammatory cytokines, such as TNFα and IL-8 Administration of EMAP II to mice resulted in evidence of systemic toxicity, as well as release of cytokines into the plasma. The pattern of cytokine elaboration following infusion of EMAP II was somewhat different than that observed with LPD (69); in the former, TNFα appeared later, while IL-6 was detected earlier. EMAP II also produced a more sustained elevation in plasma levels of IL-1β. In other studies, it was observed that local injection of recombinant EMAP II into the mouse footpad evoked an acute inflammatory response (data not shown) comparable to that previously seen in experiments with EMAP II purified from Meth A cells (13). These data suggest the importance of pursuing studies to delineate the contribution of EMAP II in models of inflammation. Preliminary evidence suggests that treatment of MPs and LPS leads to their production of EMAP II3, suggestion a role for EMAP II in endotoxin-mediated host responses and the proinflammatory cytokine cascade.

In the setting of tumor biology, EMAP II has the potential to modulate tumor vasculature by promoting thrombohemorrhage and increasing vascular permeability (13). One consequence of these changes is likely to be EMAP II-induced compromise of tumor vasculature. Injection of EMAP II into a tumor which is capable of eliciting an inflammatory response, such as the Meth A sarcoma (4), augments tumor thrombohemorrhage, acute inflammation in the tumor bed, and subsequent tumor regression. Administration of EMAP II to a tumor which is not initially sensitive to TNF, such as the MC2 murine mammary carcinoma, resulted in a local priming effect permitting subsequent thrombohemorrhage and regression once the tumors were treated with systemic TNF or EMAP II. Although it might have been anticipated that EMAP II-induced TNF production at the site of the tumor would be sufficient to initiate thrombohemorrhage, the priming dose of EMAP II had to be followed by a provocative challenge with TNF for the tumor vascular response to be observed. The potential of locally injected EMAP II to prepare the site for a later severe inflammatory response is reminiscent of the preparatory injection in the Shwartzman reaction (70, 71) and suggests its potential in the therapy of tumors which are relatively resistant to cytokines such an TNF. Consistent with this hypothesis, recent pilot studies suggest that EMAP II similarly primes the tumor bed of B16 melanomas and human fibrosarcomas (the later grown in immunodeficient mice) to undergo an acute inflammatory response followed by tumor regression.

The effects of EMAP II in the tumor bed are likely to be complex. Based on the protracted duration of inflammation following local injection of EMAP II into the tumor bed, compared with a much briefer acute inflammatory response following injection of EMAP II into normal tissue (13; also, EMAP II-induced changes in properties in cells in vitro are transient, returning to the base line in most cases by 12-24 h), it is speculated that EMAP II produces multiple effects on inflammatory and vascular cells in the tumor resulting in a sustained perturbation of cellular properties. EMAP II is also likely to have direct effects on neoplastic cells as well, as suggested by the striking decrease of viable cells obtained from murine mammary carcinomas following treatment with EMAP II and TNF. In support of this hypothesis, pilot studies have shown that EMAP II induces apoptosis of mammary carcinoma cells as well as other tumor cell lines in vitro.[3] It is unlikely that a tumor would elaborate a mediator designated solely for its destruction, means through which EMAP II could also have a beneficial effect on survival of the neoplasm have been considered. One such mechanism is suggested by the observation that EMAP II induces IL-8 production by MPs. Since IL-8 is a potent inducer of angiogenesis (72, 73), EMAP II may indirectly facilitate the establishment and growth of a tumor early in its development. Further studies with transfected tumor cell lines which overexpress EMAP II, and with reagents which block EMAP II-cellular interactions, will be required to fully assess the many mechanisms likely to be involved.

REFERENCES FOR THE SECOND SERIES OF EXPERIMENTS

1. Folkman, J., and Klagsbrun, M. (1987) Science 235, 442–447
2. Risau, W. (1990) Prog. Growth Factor Res. 2, 71–79
3. Bibby, M., Double, J., Loadman, P., and Duke, C. (1989) J. Natl. Can. Inst. 81, 216–220
4. Old, L. (1986) Science 230, 630–632
5. Asher, A., Mule, J., Reichert, C., Shiloni, E., and Rosenberg, S. (1987) J. Immunol. 138, 963–974
6. Karpate, R., Banks, S., malissen, B., Rosenberg, S., Sheard, M., Weber, J., and Hodes, R. (1991) J. Inununol. 146, 2043–2051
7. Constantinidis, I., Branuschweiger, P., Wehrie, J., Kumar, N., Johnson, C., Furmanski, P., and Glickson, J. (1989) Cancer Res. 49, 6379–6382
8. Watanabe, N., Niitsu, Y., Umeno, H., Kuriyama, H., Neda, H., Yamsuchi, N., Maeda, M., and Urushizaki, I. (1988) Cancer Res. 48, 2179–2183
9. Senger, D., Galli, S., Dvorak, A., Perruzii, C., Harvey, V., and Dvorak, H. (1983) Science 219, 983–985
10. Nawroth, P., Handley, D., Matsueda, G., De Waal, R., Geriach, H., Blohm, D., and Stern, D. (1988) J. Exp. Med. 168, 637–647
11. Clauss, M., Murray, J., Vianna, M., De Waal, R., Thruston, G., Nawroth, P., Geriach, H., Gerlach, M., Bach, R., Familletti, P., and Stern, D. (1990) J. Biol. Chem. 265, 7078–7083
12. Clauss, M., Gerlach, M., Gerlach, H., Brett, J., Wang, F., Familletti, P., Pan, Y-C., Olander, J., Connolly, D., and Stern, D. (1990) J. Exp. Med. 172, 1535–1545
13. Kao, J., Ryan, J., Brett, J., Chen, J., Shen, H., Pan, Y-G., Godman, G., Familletti, P., Wang, F., Pan, Y-C., Stern, D., and Clauss, M. (1992) J. Biol. Chem. 267, 20239–20247
14. Old, L., Benacerraf, B., Clarke, D., Carswell, D., and Stockert, E. (1961) Cancer Res. 21, 1281–1300
15. Shen, H., Clauss, M., Kao, J., Ryan, J., Schmidt, A-M., Tijburg, P., Borden, L., and Stern, D. (1993) Blood 81, 2767–2773
16. Bradley, J., Bishop, G., St. John, T., and Frelinger, J. (1988) BioTechniques 6, 114–116
17. Leung, D., Parent, A., Cachianes, G., Esch, F., Coulombe, J., Nikolics, K., Eckenstein, F., and Nishi, R. (1992) Neuron 8, 1045–1053
18. Sambrook, J., Fritsch, E., and Maniatis, T. (1989) Molecular Cloning: a Laboratory Manual, Cold Spring Harbor Laboratory Press, Cold Spring Harbor, N.Y.
19. Laemmli, U. (1970) Nature 227, 680–685
20. Jaffe, E., (1984) in Biology of Endothelial Cells (Jaffe, E., ed) pp. 1–13, Martinus Nijhoff, Boston
21. Thornton, S., Mueller, S., and Levine, E., (1983) Science 222, 623–626
22. Quinn, M., Parthasarathy, S., Fong, L., and Steinberg, D. (1987) Proc. Natl Acad. Sci. U.S.A. 84, 2995–2998
23. Boyum, A. (1968) Scank. J. Lab. Invest. 21, (Suppl. 97) 77–81
24. Kondo, S., and Kisiel, W. (1987) Blood 70, 1947–1954
25. Kao, J., Fan, Y-g., Haehnel, I., Brett, J., Greenberg, S., Clauss, M., Kayton, M., Houck, K., Kisiel, W., Burnier, J., and Stern, D. (1994) J. Biol Chen. 269, 9774–9782
26. Pober, J., Slowik, M., DeLuca, L., and Ritchie, A. (1993) J. Immunol. 150, 5114–5123
27. Johnson, D., Gautsch, J., Sprotsman, J., and Elder, J. (1984) Gene Anal. Tech. 1, 3–8
28. Tsomides, T., Walker, B., and Eisen, H. (1991) Proc. Natl. Acad. Sci. U.S.A. 88, 11276–11280
29. Hattori, R., Hamilton, K., Fugate, R., McEver, R., and Sims, P. (1989) J. Biol. Chem. 264, 7768–7771
30. Grynkiewicz, G., Pienie, M., and Tsien, R. (1985) J. Biol. Chem. 260, 3440–3450
31. Regehr, W., and Tank, D. (1992) J. Neuroaci. 12, 4202–4223
32. Greeberg, S., DiVirgilio, F., Steinberg, T., and Silverstein, S. (1988) J. Biol. Chem. 263, 10337–10343
33. DiVirgilio, F., Meyer, B., Greenberg, S., and Silverstein, S. (1986) J. Cell biol. 106, 657–666
34. DiVirgilio, F., Steinberg, T., and Silverstein, S. (1990) Cell Calcium 11, 57–62
35. Harvath, L., Falk, Wl, and Leonard, E. (1980) J. Immunol Methods 37, 39–45
36. Menegazzi, R., Zabucchi, G., Knowles, A., Cramer, R., and Patriarca, P. (1992) J. Leuk. Biol. 52, 619–624

37. Goldblum, S., Wu, K., and Jay, M. (1985) J. Appl. Phusiol. 59, 1978–1985
38. Koga, S., Orawa, S., Kuwabara, K., Brett, J., Leavy, J., Ryan, J., Koga, Y., Plocinski, J., Benjamin, W., Burns, D., and Stern, D. (1992) J. Clin. Invest. 90, 1007–1015
39. Karakurum, M., Shreeniwas, R., Chen, J., Sunouchi, J., Hamilton, T., Anderson, M., Kuwabara, K., Rot, A., Nowygrod, R., and Stern, D. (1994) J. Clin. Invest. 93, 1564–1570
40. Carre, P. Mortenson, R., King, T., Noble, P., Sable, C., and Riches, D. (1991) J. Clin. Invest. 88, 1802–1810
41. Brett, J., Schmidt, A-M., Zou, Y-S., Yan, S-D., Weidman, E., Pinsky, D., Neeper, M., Przysiecki, M., Shaw, A., Migheli, A., and Stern, D. (1993) Am J. Pathol. 143, 1699–1712
42. Lo, S., Everitt, J., Gu, J., and Malik, A. (1992) J. Clin. Invest. 89, 981–988
43. Weast, R. C. (1966) Handbook of Chemistry and Physics, The Chemical Rubber Company, Cleveland, Ohio
44. Vaage, J., and Pepin, K. (1985) Cancer Res. 45, 659–666
45. Twentyman, P., Brown, J., Gray, J., Franko, A., Scoles, M., and Kallman, R. (1980) J. Natl Cancer Inst. 64, 595–604
46. Branuaschweiger, P., Kumar, N., Constantinidis, I., Wehrle, J., Glickson, J., Johnson, C., and Furmanski, P. (1990) Cancer Res. 50, 4709–4717
47. Kizak, M. (1989) J. Cell Biol. 108, 229–241
48. March, C., Mosley, B., Larsen, A., Cerretti, D., Braedt, G., Price, V., Gillis, Sl, Henney, C., Kronheim, S., Grabstein, K., Conlon, P., Hopp, T., and Cosman, D. (1985) Nature 315, 641–647
49. Mosley, B., Urdal, D., Prickett, K., Larsen, A., Cosman, D., Conlon, P., Gillis, S., and Dower, S. (1987) J. Biol. Chem. 262, 2941–2944
50. Black, R., Kronheim, S., and Sleath, P. (1989) FEBS Lett. 247, 386–390
51. Thornberry, N., Bull, H., Calaycay, J., Chapman, K., Howard, A., Kostura, A., Miller, D., Molineaux, S., Weidner, J., Aunins, J., Elliston, K., Ayala, J., Casano, F., Chin, J., Ding, G., Egger, L., Gaffney, E., Limjuco, G., Palyha, O., Raju, S., Rolando, jA., Salley, J., Yamin, T., Lee, T., Shively, J., MacCross, M., Mumford, R., Schmidt, J., and Tocci, M. (1992) Nature 356, 768–774
52. Cerretti, D., Kozlosky, C., Mosley, B., Nelson, N., Van Ness, K., Greenstreet, T., March, C., Kronheim, S., Druck, T., Cannizzaro, L., Huebner, K., and Black, R. (1992) Science 256, 97–100
53. Schmidt, J., and Tocci, M. (1990) in Peptide Growth Factors and Teir Receptors (Sporn, M., and Roberts, A., eds) pp. 473–521, Springer, Berlin
54. Matsushima, K., Morishita, K., Yoshimura, T., Lavu, S., Kobaysshi, Y., Lew, W., Appella, E., Kung, H., Leonard, E., and Oppenheim J. (1988) J. Exp. Med. 167, 1883–1893
55. Lindley, I., Aschauer, H., Seifer, J-M., Lam, C., Brunowsky, W., Kownatzki, E., Thelen, M., Peveri, P., Dewald, B., von Tsharner, V., Walz, A., and Baggiolini, M. (1988) Proc. Natl. Acad. Sci. U.S.A. 85, 9199–9203
56. Scott, J., and Montgomery, R. (1981) Blood 58, 1075–1080
57. Wagner, D., and Bonfanti, R. (1991) Mayo Clin. Proc. 66, 621–627
58. Sauder, D., Mounessa, N., Katz, S., Dinarello, C., and Gallin, J. (1984) J. Immunol. 132, 828–833
59. Bonthron, D., Handin, R., Kaufman, R., Wasley, L., Orr, E., Mitsock, L., Ewenstein, B., Loscalzo, J., Ginsburg, D., and Orkin, S. (1986) Nature 324, 270–273
60. Fay, P., Kawai, Y., Wagner, D., Ginsburg, D., Bonthron, D., Ohlsson-Wilhelm, B., Chavin, S., Abraham, G., Handin, R., Orkin, S., Montgomery, R., and Marder, V. (1966) Science 232, 995–998
61. Yoshimura, T., Matsuschima, K., Tanada, S., Robinson, E., Apella, E., Oppenheim, J., and Leonard, E. (1987) Proc. Natl. Acad. Sci. U.S.A. 84, 9233–9237
62. Tijburg, P., Kao, J., Yan, S-D., van Mourik, J., and Stern, D. (1992) Circulation 86, (Suppl II), 1626
63. Outzen, H., Corrow, D., and Shultz, L. (1985) J. Natl. Cancer Inst. 75, 917–923
64. Herbert, C., Vitangcol, R., and Baker, J. (1991) J. Biol. Chem. 266, 18989–18994
65. Retrosen, D., and Gallin, J. (1986) J. Cell Biol 103, 2379–2387
66. Birch, K., Pober, J., Zavioco, G., Means, A., and Ewenstein, B. (1992) J. Cell Biol. 118, 1501–1510
67. Pober, J., and Cotran, R. (1990) Phusiol. Revs. 70, 427–451
68. Oppenheim, J., Zacharise, C., Mukaida, N., and Matsushima, K. 1991) Annu. Rev. Immunol. 9, 617–648
69. Chensue, S., Terebuh, P., Remick, D., Scales, W., and Kunkel, S. (1991) Am. J. Pathol. 138, 395–402
70. Brozna, J. (1990) Semin. Thromb. Hemostasis 16, 326–332
71. Movat, H., Burrowes, C., Cybulsky, M., and Dinarello, C. (1987) Am J. Pathol. 129, 463–476
72. Strietar, R., Kunkel, S., Elner, V., Martonyi, C., Koch, A., Polverini, P., and Elner, S. (1992) Am. J. Pathol. 141, 1279–1284
73. Koch, A., Polverini, P., Kunkel, S., Harlow, L., DiPietro, L., Elner, V., Elner, S., and Strieter, R. (1992) Science 258, 1798–1801
74. Kyte, J., and Doolittle, R. (1982) J. Mol. Biol. 157, 105–132

---

What is claimed is:

1. A purified endothelial monocyte activating polypeptide II selected from the group consisting of the polypeptides having amino acid sequences shown in SEQ ID NOs. 11, 35 and 36.

2. The endothelial monocyte activating polypeptide II of claim 1 having an apparent molecular weight of about 20,000 Daltons.

3. Endothelial monocyte activating polypeptide II of claim 1 wherein the endothelial monocyte activating polypeptide II is murine endothelial monocyte activating polypeptide II.

4. A polypeptide comprising a chain of amino acids, the sequence of which is:

Gly-Lys-Pro-Ile-Asp-Ala-Ser-Arg-Leu-Asp-Leu-Arg-Ile-Gly-Xaa-Ile-Val-Thr-Ala-Lys (SEQ ID No. 1).

5. A method of obtaining the purified polypeptide of claim 1 comprising:
   a) obtaining conditioned medium containing Meth A cells;
   b) purifying the medium from Meth A cells;
   c) applying the purified medium to a cation exchange resin;
   d) step-eluting from the cation exchange resin and pooling fractions with $OD_{280}>0.05$;
   e) applying the pooled fractions to an FPLC column; and
   f) eluting with an ascending salt gradient, thereby obtaining the is purified polypeptide of claim 1.

6. A method of inducing inflammation in a subject comprising injecting an inflammation-inducing effective amount of the polypeptide of claim 1 into the footpad of the subject.

7. The method of claim 6 wherein the subject is a mouse.

8. A method of treating a tumor in a subject comprising administering an effective dose of the endothelial monocyte activating polypeptide II of claim 1.

9. The method of claim 8 for inducing hemorrhage in the tumor.

10. The method of claim 8 for reducing the volume of the tumor.

11. The method of claim 10 wherein the volume of the tumor is reduced by at least twenty-five percent.

12. The method of claim 8 wherein the tumor is a methylcholanthrene A-induced fibrosarcoma.

13. The method of claim 8 wherein the subject is a mammal.

14. The method of claim 13 wherein the mammal is a mouse.

15. The method of claim 8 wherein the effective dose is between about two micrograms and about fifty micrograms.

16. The method of claim 8 wherein the effective dose is between about six and about one hundred fifty micrograms.

17. The method of claim 8 wherein the endothelial monocyte activating polypeptide II is in a pharmaceutically acceptable carrier.

18. The method of claim 8 wherein the administering comprises injecting intratumorally.

19. The method of claim 18 wherein the administering further comprises administering systemically.

20. The method of claim 8 wherein the tumor comprises carcinoma cells.

21. The method of claim 20 wherein the carcinoma cells are mouse mammary carcinoma cells.

22. The method of claim 8 which further comprises administering an effective dose of tumor necrosis factor.

23. The method of claim 22 wherein the effective dose of tumor necrosis factor is administered systemically.

24. The method of claim 22 wherein the effective dose is between about five hundred nanograms and about twelve micrograms.

25. The method of claim 24 wherein the endothelial monocyte activating polypeptide II comprises:

SKPIDASRLDLRIGCIVTAKKHPDADSLYVEEVD-
VGEAAPRTVVSGLVNHVPLEQMQNRMVVLLC-
NLKPAKMRGVLSQAMVMCASSPEKVEILAPPN-
GSVPGDRITFDAFPGEPDKELNPKKKIWEQIQP-
DLHTNAECVATYKGAPFEVKGKGVCRAQTMA-
NSGIK (SEQ ID NO. 11).

26. The method of claim 22 wherein the tumor comprises carcinoma cells.

27. The method of claim 26 wherein the carcinoma cells are mouse mammary carcinoma cells.

28. The method of claim 8 wherein the endothelial monocyte activating polypeptide II is recombinant endothelial monocyte activating polypeptide II.

29. A pharmaceutical composition comprising an effective amount of the endothelial monocyte activating polypeptide II of claim 1 in a pharmaceutically acceptable carrier.

30. A purified human endothelial monocyte activating polypeptide II having an amino acid sequence identical to the amino acid sequence shown in SEQ ID NO. 36.

31. A purified murine endothelial monocyte activating polypeptide II having an amino acid sequence identical to the amino acid sequence shown in SEQ ID NO. 35.

* * * * *

SEQUENCE LISTING (1) GENERAL INFORMATION:

(iii) NUMBER OF SEQUENCES: 42

(2) INFORMATION FOR SEQ ID NO:1:

(i) SEQUENCE CHARACTERISTICS:
      (A) LENGTH: 20 amino acids
      (B) TYPE: amino acid
      (C) STRANDEDNESS: single
      (D) TOPOLOGY: linear (ii) MOLECULE TYPE: Peptide (iii) SEQUENCE DESCRIPTION: SEQ ID NO:1:

Gly Lys Pro Ile Asp Ala Ser Arg Leu Asp Leu Arg Ile Gly Xaa Ile
1               5                   10                  15

Val Thr Ala Lys
            20

(2) INFORMATION FOR SEQ ID NO:2:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: Peptide (iii) SEQUENCE DESCRIPTION: SEQ ID NO:2:

Gly Lys Pro Ile Asp Ala Ser Arg Leu Asp Leu Arg Ile Gly Cys Ile
1               5                   10                  15

Val Thr Ala Lys
            20

(2) INFORMATION FOR SEQ ID NO:3:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: Peptide (iii) SEQUENCE DESCRIPTION: SEQ ID NO:3:

Arg Ile Gly Arg Ile Val Thr
1               5

(2) INFORMATION FOR SEQ ID NO:4:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: Peptide (iii) SEQUENCE DESCRIPTION: SEQ ID NO:4:

Arg Ile Gly Arg Ile Val Thr Ala Lys Tyr
1               5                   10

(2) INFORMATION FOR SEQ ID NO:5:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: Peptide
        (A) DESCRIPTION: Cys at position 10 is carboxymethylated.

(iii) SEQUENCE DESCRIPTION: SEQ ID NO:5:

Ala Ser Arg Leu Asp Leu Arg Ile Gly Cys Ile Val Thr Ala Lys
1               5                   10                  15

(2) INFORMATION FOR SEQ ID NO:6:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: Peptide (iii) SEQUENCE DESCRIPTION: SEQ ID NO:6:

```
Ala Ser Arg Leu Asp Leu Arg Ile Gly Arg Ile Val Thr Ala Lys Tyr
1               5                   10                  15
```

(2) INFORMATION FOR SEQ ID NO:7:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: Peptide (iii) SEQUENCE DESCRIPTION: SEQ ID NO:7:

```
Ala Ser Arg Leu Asp Leu Arg Ile Gly Arg Ile Val Thr Ala Lys
1               5                   10                  15
```

(2) INFORMATION FOR SEQ ID NO:8:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: Peptide (iii) SEQUENCE DESCRIPTION: SEQ ID NO:8:

```
Leu Arg Ile Gly Arg Ile Val Thr Ala Lys Tyr
1               5                   10
```

(2) INFORMATION FOR SEQ ID NO:9:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: Peptide (iii) SEQUENCE DESCRIPTION: SEQ ID NO:9:

```
Arg Ile Gly Arg Ile Ile Thr
1               5
```

(2) INFORMATION FOR SEQ ID NO:10:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: Peptide (iii) SEQUENCE DESCRIPTION: SEQ ID NO:10:

```
Ala Ile Gly Arg Ile Val Thr
1               5
```

(2) INFORMATION FOR SEQ ID NO:11:

(i) SEQUENCE CHARACTERISTICS:
        (A) LENGTH: 166 amino acids
        (B) TYPE: amino acid
        (C) STRANDEDNESS: single
        (D) TOPOLOGY: linear (ii) MOLECULE TYPE: Peptide (iii) SEQUENCE DESCRIPTION: SEQ ID NO:11:

```
Ser Lys Pro Ile Asp Ala Ser Arg Leu Asp Leu Arg Ile Gly Cys Ile
1               5                   10                  15

Val Thr Ala Lys Lys His Pro Asp Ala Asp Ser Leu Tyr Val Glu Glu
            20                  25                  30

Val Asp Val Gly Glu Ala Ala Pro Arg Thr Val Val Ser Gly Leu Val
        35                  40                  45

Asn His Val Pro Leu Glu Gln Met Gln Asn Arg Met Val Val Leu Leu
    50                  55                  60

Cys Asn Leu Lys Pro Ala Lys Met Arg Gly Val Leu Ser Gln Ala Met
65                  70                  75                  80

Val Met Cys Ala Ser Ser Pro Asp Lys Val Glu Ile Leu Ala Pro Pro
                85                  90                  95

Asn Gly Ser Val Pro Gly Asp Arg Ile Thr Phe Asp Ala Phe Pro Gly
                100                 105                 110

Glu Pro Asp Lys Glu Leu Asn Pro Lys Lys Ile Trp Glu Gln Ile
            115                 120                 125

Gln Pro Asp Leu His Thr Asn Ala Glu Cys Val Ala Thr Tyr Lys Gly
        130                 135                 140

Ala Pro Phe Glu Val Lys Gly Lys Gly Val Cys Arg Ala Gln Thr Met
145                 150                 155                 160

Ala Asn Ser Gly Ile Lys
                165
```

(2) INFORMATION FOR SEQ ID NO:12:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: Peptide (iii) SEQUENCE DESCRIPTION: SEQ ID NO:12:

```
Ala Ile Leu Arg Gln Val Thr
1               5
```

(2) INFORMATION FOR SEQ ID NO:13:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: Peptide (iii) SEQUENCE DESCRIPTION: SEQ ID NO:13:

```
Leu Ala Ile Leu Arg Gln Val Thr
1               5
```

(2) INFORMATION FOR SEQ ID NO:14:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: Peptide (iii) SEQUENCE DESCRIPTION: SEQ ID NO:14:

Asp Leu Arg Ile Gln Arg Thr Val Thr Ala Ser
1               5                   10

(2) INFORMATION FOR SEQ ID NO:15:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: Peptide (iii) SEQUENCE DESCRIPTION: SEQ ID NO:15:

Cys Arg Ala Gln Thr Met Ala Asn Ser Gly Ile Lys
1               5                   10

(2) INFORMATION FOR SEQ ID NO:16:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: Peptide (iii) SEQUENCE DESCRIPTION: SEQ ID NO:16:

Ala Val Leu Pro Arg Ser Ala Lys Glu Leu Arg Leu
1               5                   10

(2) INFORMATION FOR SEQ ID NO:17:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: Peptide (iii) SEQUENCE DESCRIPTION: SEQ ID NO:17:

Ile Arg Lys Asp Met Asp Lys Val Glu Thr Phe Leu Arg Ile Val Gln
1               5                   10                  15

(2) INFORMATION FOR SEQ ID NO:18:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: Peptide (iii) SEQUENCE DESCRIPTION: SEQ ID NO:18:

Ala Ser Arg Leu Asp Leu
1               5

(2) INFORMATION FOR SEQ ID NO:19:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: Peptide (iii) SEQUENCE DESCRIPTION: SEQ ID NO:19:

```
Arg Ile Gly Arg Ala Val Thr
1               5
```

(2) INFORMATION FOR SEQ ID NO:20:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: Peptide (iii) SEQUENCE DESCRIPTION: SEQ ID NO:20:

```
Ala Ser Arg Leu Asp Leu Arg Ile Gly Arg Ile Val Thr
1               5                   10
```

(2) INFORMATION FOR SEQ ID NO:21:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: Peptide (iii) SEQUENCE DESCRIPTION: SEQ ID NO:21:

```
Xaa Ile Gly Xaa Ile Val Thr
1               5
```

(2) INFORMATION FOR SEQ ID NO:22:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: Peptide (iii) SEQUENCE DESCRIPTION: SEQ ID NO:22:

```
Xaa Ile Gly Xaa Ile Ile Thr
1               5
```

(2) INFORMATION FOR SEQ ID NO:23:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: Peptide (iii) SEQUENCE DESCRIPTION: SEQ ID NO:23:

```
Ala Ala Arg Cys Cys Asn Ala Thr His Gly Ala Tyr Gly Cys
1               5                   10
```

(2) INFORMATION FOR SEQ ID NO:24:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: Peptide (iii) SEQUENCE DESCRIPTION: SEQ ID NO:24:

```
Tyr Thr Thr Asn Gly Cys Asn Gly Thr Asn Ala Cys Asp Ala Thr
1               5                   10                  15
```

(2) INFORMATION FOR SEQ ID NO:25:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (genomic)

(iii) ANTI-SENSE: N (iv) SEQUENCE DESCRIPTION: SEQ ID NO:25:

AAGCCCATTG ATGCCTCCCG GCTGGACCTG CGGATTGGCT GCATTGTGAC AGCCAAG       57

(2) INFORMATION FOR SEQ ID NO:26:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) SEQUENCE DESCRIPTION: SEQ ID NO:26:

ATTTTGCATC TGTTCTAG       18

(2) INFORMATION FOR SEQ ID NO:27:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: Peptide (iii) SEQUENCE DESCRIPTION: SEQ ID NO:27:

```
Lys Pro Ile Asp Ala Ser Arg Leu Glu Leu
1               5                   10
```

(2) INFORMATION FOR SEQ ID NO:28:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(iii) SEQUENCE DESCRIPTION: SEQ ID NO:28:

TATGAAACCA ATCGATGCAT CTCGTCTGGA TCTT       34

(2) INFORMATION FOR SEQ ID NO:29:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(iii) SEQUENCE DESCRIPTION: SEQ ID NO:29:

CGAAGATCCA GACGAGATGC ATCGATTGGT TTCA                                    34

(2) INFORMATION FOR SEQ ID NO:30:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) SEQUENCE DESCRIPTION: SEQ ID NO:30:

CCACCCATGG CAAATTCCAT GGCA                                            24

(2) INFORMATION FOR SEQ ID NO:31:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) SEQUENCE DESCRIPTION: SEQ ID NO:31:

TCTAGACGGC AGGTCAGGTC CACC                                            24

(2) INFORMATION FOR SEQ ID NO:32:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:32:

GGCGAATTCA ANCCNATNGA NGC                                             23

(2) INFORMATION FOR SEQ ID NO:33:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:33:

GGCGAATTCN TTNGCNGTNA CNAT                                            24

(2) INFORMATION FOR SEQ ID NO:34:

(i) SEQUENCE CHARACTERISTICS:
        (A) LENGTH: 1086 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:34:

```
GAGGCTGCTC AAGAGCTGCG GTTGGGTCAC CGCTTCATGT TTCTCTGCCG ATTCTGGGGA      60
AAGATGGCAA CGAATGATGC TGTTCTGAAG AGGCTGGACC AGAAGGGTGC AGAGGCGGAT     120
CAGATCATCG AATATCTCAA GCAGCAGGTT GCTCTTCTTA AGGAGAAAGC AATTTTGCAG     180
GCAACAATGA GAGAAGAAAA GAAACTTCGA GTTGAAAATG CTAAACTGAA AAAAGAAATA     240
GAAGAGCTAA AGCAAGAGCT GATTCTGGCA GAAATTCATA ACGGAGTGGA GCAAGTGCGT     300
GTTCGATTGA GTACTCCACT GCAGACGAAC TGTACTGCTT CTGAAAGTGT GGTGCAGTCT     360
CCATCAGTAG CAACCACCGC CTCTCCTGCT ACAAAAGAGC AGATCAAAGC GGGAGAAGAA     420
AAGAAGGTGA AAGAGAAGAC TGAAAAGAAA GGAGAGAAAA AGGAGAAGCA GCAGTCGGCA     480
GCAGCAAGTA CTGACTCCAA GCCTATCGAC GCATCGCGTC TGGATCTTCG AATTGGTTGT     540
ATTGTTACTG CCAAGAAGCA CCCTGATGCA GATTCACTGT ATGTGGAGGA AGTAGATGTG     600
GGAGAAGCAG CCCCGCGCAC GGTCGTCAGC GGGCTGGTGA ATCATGTTCC TCTAGAACAG     660
ATGCAAAATC GTATGGTGGT TTTACTCTGT AATCTGAAGC TGCAAAGAT GCGGGGAGTT     720
CTGTCTCAAG CCATGGTGAT GTGTGCCAGT TCACCAGAGA AAGTGGAGAT TCTGGCCCCT     780
CCCAACGGGT CCGTTCCTGG GGACAGAATT ACTTTTGATG CTTTTCCTGG AGAGCCTGAC     840
AAGGAGCTAA ACCCTAAGAA GAAGATCTGG GAGCAGATCC AGCCTGACCT GCACACCAAT     900
GCTGAGTGTG TGGCCACATA CAAAGGAGCT CCCTTTGAGG TGAAGGGGAA GGGAGTTTGC     960
AGAGCCCAAA CCATGGCCAA TAGTGGAATT AAATAAGTGC TCTGTAACTG AAAGACATTG    1020
GCGAAAACTT AATAACAATA AGAGAAGTG TGTTTATCAC TTACATATAA AAAAAAAAA    1080
AAAAAA                                                               1086
```

(2) INFORMATION FOR SEQ ID NO:35:

(i) SEQUENCE CHARACTERISTICS:
        (A) LENGTH: 310 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:35:

```
Met Ala Thr Asn Asp Ala Val Leu Lys Arg Leu Glu Gln Lys Gly Ala
 1               5                  10                  15

Glu Ala Asp Gln Ile Ile Glu Tyr Leu Lys Gln Gln Val Ala Leu Leu
                20                  25                  30

Lys Glu Lys Ala Ile Leu Gln Ala Thr Met Arg Glu Lys Lys Leu
            35                  40                  45

Arg Val Glu Asn Ala Lys Leu Lys Lys Glu Ile Glu Glu Leu Lys Gln
        50                  55                  60

Glu Leu Ile Leu Ala Glu Ile His Asn Gly Val Glu Gln Val Arg Val
65                  70                  75                  80
```

-continued

```
Arg Leu Ser Thr Pro Leu Gln Thr Asn Cys Thr Ala Ser Glu Ser Val
                 85                  90                  95

Val Gln Ser Pro Ser Val Ala Thr Thr Ala Ser Pro Ala Thr Lys Glu
            100                 105                 110

Gln Ile Lys Ala Gly Glu Glu Lys Lys Val Lys Glu Lys Thr Glu Lys
        115                 120                 125

Lys Gly Glu Lys Lys Glu Lys Gln Gln Ser Ala Ala Ala Ser Thr Asp
    130                 135                 140

Ser Lys Pro Ile Asp Ala Ser Arg Leu Asp Leu Arg Ile Gly Cys Ile
145                 150                 155                 160

Val Thr Ala Lys Lys His Pro Asp Ala Asp Ser Leu Tyr Val Glu Glu
                165                 170                 175

Val Asp Val Gly Glu Ala Ala Pro Arg Thr Val Val Ser Gly Leu Val
            180                 185                 190

Asn His Val Pro Leu Glu Gln Met Gln Asn Arg Met Val Val Leu Leu
        195                 200                 205

Cys Asn Leu Lys Pro Ala Lys Met Arg Gly Val Leu Ser Gln Ala Met
    210                 215                 220

Val Met Cys Ala Ser Ser Pro Glu Lys Val Glu Ile Leu Ala Pro Pro
225                 230                 235                 240

Asn Gly Ser Val Pro Gly Asp Arg Ile Thr Phe Asp Ala Phe Pro Gly
                245                 250                 255

Glu Pro Asp Lys Glu Leu Asn Pro Lys Lys Lys Ile Trp Glu Gln Ile
            260                 265                 270

Gln Pro Asp Leu His Thr Asn Ala Glu Cys Val Ala Thr Tyr Lys Gly
        275                 280                 285

Ala Pro Phe Glu Val Lys Gly Lys Gly Val Cys Arg Ala Gln Thr Met
    290                 295                 300

Ala Asn Ser Gly Ile Lys
305                 310

(2) INFORMATION FOR SEQ ID NO:36:

(i) SEQUENCE CHARACTERISTICS:
        (A) LENGTH: 312 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:36:

Met Ala Asn Asn Asp Ala Val Leu Lys Arg Leu Glu Gln Lys Gly Ala
1               5                   10                  15

Glu Ala Asp Gln Ile Ile Glu Tyr Leu Lys Gln Gln Val Ser Leu Leu
            20                  25                  30

Lys Glu Lys Ala Ile Leu Gln Ala Thr Leu Arg Glu Glu Lys Lys Leu
        35                  40                  45

Arg Val Glu Asn Ala Lys Leu Lys Lys Glu Ile Glu Glu Leu Lys Gln
    50                  55                  60

Glu Leu Ile Gln Ala Glu Ile Gln Asn Gly Val Lys Gln Ile Pro Phe
65                  70                  75                  80

Pro Ser Gly Thr Pro Leu His Ala Asn Ser Met Val Ser Glu Asn Val
                85                  90                  95

Ile Gln Ser Thr Ala Val Thr Thr Val Ser Ser Gly Thr Lys Glu Gln
            100                 105                 110
```

```
Ile Lys Gly Gly Thr Gly Asp Glu Lys Ala Lys Glu Lys Ile Glu
            115                 120                 125
Lys Lys Gly Glu Lys Lys Glu Lys Lys Gln Gln Ser Ile Ala Gly Ser
130                 135                 140
Ala Asp Ser Lys Pro Ile Asp Val Ser Arg Leu Asp Leu Arg Ile Gly
145                 150                 155                 160
Cys Ile Ile Thr Ala Arg Lys His Pro Asp Ala Asp Ser Leu Tyr Val
                165                 170                 175
Glu Glu Val Asp Val Gly Glu Ile Ala Pro Arg Thr Val Val Ser Gly
            180                 185                 190
Leu Val Asn His Val Pro Leu Glu Gln Met Gln Asn Arg Met Val Ile
                195                 200                 205
Leu Leu Cys Asn Leu Lys Pro Ala Lys Met Arg Gly Val Leu Ser Gln
            210                 215                 220
Ala Met Val Met Cys Ala Ser Ser Pro Glu Lys Ile Glu Ile Leu Ala
225                 230                 235                 240
Pro Pro Asn Gly Ser Val Pro Gly Asp Arg Ile Thr Phe Asp Ala Phe
                245                 250                 255
Pro Gly Glu Pro Asp Lys Glu Leu Asn Pro Lys Lys Lys Ile Trp Glu
            260                 265                 270
Gln Ile Gln Pro Asp Leu His Thr Asn Asp Glu Cys Val Ala Thr Tyr
        275                 280                 285
Lys Gly Val Pro Phe Glu Val Lys Gly Lys Gly Val Cys Arg Ala Gln
            290                 295                 300
Thr Met Ser Asn Ser Gly Ile Lys
305                 310

(2) INFORMATION FOR SEQ ID NO:37:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:37:

Arg Gly Arg Ile Val Thr Ile
1               5

(2) INFORMATION FOR SEQ ID NO:38:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:38:

Arg Ile Gly Arg Ile Val Thr Ala Lys
1               5

(2) INFORMATION FOR SEQ ID NO:39:

(i) SEQUENCE CHARACTERISTICS:
            (A) LENGTH: 20 amino acids
            (B) TYPE: amino acid
            (C) STRANDEDNESS: single
            (D) TOPOLOGY: linear
```

-continued

```
        (ii) MOLECULE TYPE: peptide (xi) SEQUENCE DESCRIPTION: SEQ ID NO:39:

Lys Pro Ile Asp Val Ser Arg Leu Asp Leu Arg Ile Gly Cys Ile Ile
1               5                   10                  15

Thr Ala Lys Lys
            20

(2) INFORMATION FOR SEQ ID NO:40:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:40:

Val Gln Leu Pro Leu Leu Lys Gly Asp Leu Arg Ile Gln Arg Thr Val
1               5                   10                  15

Thr Ala Ser Val
            20

(2) INFORMATION FOR SEQ ID NO:41:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:41:

Ala Val Leu Pro Arg Ser Ala Lys Glu Leu Arg Cys Gln Cys Ile Lys
1               5                   10                  15

Thr Tyr Ser Lys
            20

(2) INFORMATION FOR SEQ ID NO:42:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:42:

Ala Pro Val Arg Ser Leu Asn Cys Thr Leu Arg Asp Ser Gln Gln Lys
1               5                   10                  15

Ser Leu Val Met
            20
```